United States Patent
Nakai et al.

(10) Patent No.: US 6,262,114 B1
(45) Date of Patent: Jul. 17, 2001

(54) LEUKOTRIENE B$_4$ ANTAGONIST COMPOUNDS AND METHOD FOR TREATMENT

(75) Inventors: Hisao Nakai; Koumei Kamiyasu, both of Mishima-gun (JP)

(73) Assignee: Ono Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 08/975,246

(22) Filed: Nov. 21, 1997

Related U.S. Application Data

(62) Division of application No. 08/530,587, filed on Sep. 19, 1995, now abandoned.

Foreign Application Priority Data

Sep. 20, 1994 (JP) .................................................. 6-250158

(51) Int. Cl.$^7$ ........................ A61K 31/216; C07C 279/18
(52) U.S. Cl. ..................... 514/533; 514/539; 560/41; 560/42; 560/49
(58) Field of Search ................ 560/42, 41, 49; 514/533, 539

(56) References Cited

U.S. PATENT DOCUMENTS

| | | | |
|---|---|---|---|
| 5,246,965 | 9/1993 | Main | 514/532 |
| 5,514,713 | * 5/1996 | Nakai | 514/533 |
| 5,614,555 | * 3/1997 | Nakai | 514/540 |

FOREIGN PATENT DOCUMENTS

| | | |
|---|---|---|
| 0516819 | 12/1992 | (EP) . |
| 0588655 | * 3/1994 | (EP) . |
| 0656349 | 6/1995 | (EP) . |
| 94 11341 | 5/1994 | (WO) . |

* cited by examiner

*Primary Examiner*—Robert Gerstl
(74) *Attorney, Agent, or Firm*—Stevens, Davis, Miller & Mosher, LLP

(57) ABSTRACT

Novel amidinophenol derivatives of formula (IB)

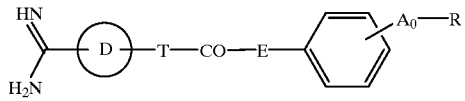

(IB)

and processes for the preparation thereof; compositions containing a compound of formula (IB) as active ingredient useful as antagonists of leukotine B$_4$ and inhibitors of phospholipase A$_2$ and/or trypsin; methods for preventing or treating diseases induced by phospholipase A$_2$ and/or trypsin comprising administering to a patient a compound of formula (IB); and methods for treating diseases induced by leukotine B$_4$ comprising administering to a patient a compound of formula (IB) or a known amidinophenol derivative of formula (IA)

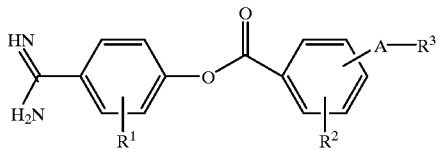

(IA)

17 Claims, No Drawings

LEUKOTRIENE B₄ ANTAGONIST COMPOUNDS AND METHOD FOR TREATMENT

This application is a Divisional of application Ser. No. 08/530,587, filed Sep. 19, 1995, now abandoned.

BACKGROUND OF THE INVENTION

1. Field of the Invention

The present invention relates to amidinophenol derivatives, processes for the preparation thereof and the use thereof as leukotriene $B_4$ ($LTB_4$)antagonists, phospholipase $A_2$ inhibitors, and trypsin inhibitors.

More particularly, it relates to $LTB_4$ antagonists containing an amidinophenol derivative of the formula (IA):

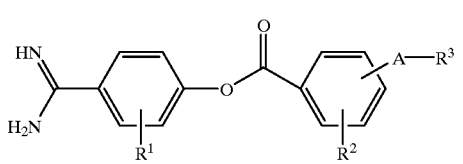

(wherein various symbols are the same meanings as hereafter described), as the active ingredient; to amidinophenol derivatives of the formula (IB):

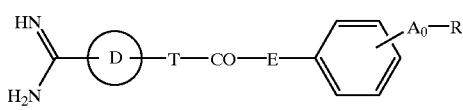

(wherein various symbols are the same meanings as hereafter described) and processes for the preparation thereof; and to $LTB_4$ antagonists, phospholipase$A_2$ inhibitors and trypsin inhibitors containing a compound of formula (IB) as the active ingredient.

2. Description of Related Art

The metabolic pathways by which various compounds are biosynthesized, in vivo, from arachidonic acid as a common starting material are called the arachidonic acid cascade.

Lipoxygenase, for example, 5-lipoxygenase, 12-lipoxygenase or 15-lipoxygenase, respectively, acts on arachidonic acid to produce 5-HPETE, 12-HPETE or 15-HPETE from arachidonic acid.

The above mentioned HPETEs are converted into 5-HETE, 12-HETE or 15-HETE, by converting a peroxy group into a hydroxy group by the action of peroxidase, and 5-HPETE is also converted into $LTA_4$.

$LTA_4$ is converted into $LTB_4$ or $LTC_4$ by enzymatic reaction (see Biochem. Biophys. Res. Commun., 91, 1266 (1979), Prostaglandins, 19(5), 645).

Recently a number of properties of $LTB_4$ have been revealed.

It is understood that $LTB_4$ has strong chemotactic and adhesive activity and degranulation activity on leukocytes (see Nature, 286, 264 (1980), Proc. Nat. Acad. Sci. USA, 78, 3887 (1981)).

$LTB_4$ also has strong calcium ionophore action, and attacks various cells, and it is considered to accelerate release of metabolites of arachidonic acid from these cells (see J. Biol. Chem, 257, 4746 (1982)).

High levels of $LTB_4$ have also been found at sites of various inflammations, for example, rheumatism, spondyl arthritis, gout, psoriasis, ulcerative colitis and respiratory tract diseases, thereby demonstrating that $LTB_4$ is closely associated with various inflammations (see J. Clin. Invest., 66, 1166 (1980); Lancet II 1122–1123 (1982); J. Invest. Dermatol., 82, 477–479 (1984); Gastroenterology 86, 453–460 (1984)).

It is therefore considered that $LTB_4$ antagonists are useful as anti-inflammatory agents or anti-allergic agents.

It is known that $LTB_4$ antagonists are also useful for the treatment of rheumatoid arthritis, inflammatory bowel diseases, psoriasis, nonsteroidal anti-inflammatory agent-induced stomach diseases, adult respiratory distress syndrome, cardiac infarction, allergic rhinitis, hemodialysis-induced neutropenia, anaphase asthma (see the specification of the Japanese Patent Kokai No. 5-239008).

Phospholipase $A_2$ ($PLA_2$) is an enzyme which acts on phospholipids existing in cell membranes. It hydrolyzes an ester bond at the second position of the phospholipids. There are two known kinds of $PLA_2$, membrane-associated $PLA_2$ and pancreatic $PLA_2$.

Membrane-associated $PLA_2$ acts on phospholipids to release arachidonic acid (AA) from the phospholipids. The AA is converted into prostaglandins, thromboxanes and leukotrienes, which are physiologically active substances inducing various inflammatory diseases and allergic diseases.

On the other hand, pancreatic $PLA_2$ degrades phospholipids and destroys cell membranes, thereby producing lysolecithin having strong cytotoxicity. Recently, much importance has been attached to pancreatitis, severity in pancreatitis and multiple organ failure induced by this destructive activity on cell membranes.

It is also reported that membrane-associated $PLA_2$ is also concerned with these diseases.

Accordingly, the inhibition of $PLA_2$ leads to the suppression of the release of AA, a precursor of various physiologically active substances, and therefore, it is considered to be useful for the prevention and/or the treatment of various inflammatory and allergic diseases. Furthermore, it is considered to be useful for the prevention and/or the treatment of pancreatitis, severity in pancreatitis and multiple organ failure due to the inhibition of the destructive activity on cell membranes.

It is also known that the inhibition of various proteases such as trypsin, plasmin, thrombin, kallilrein, especially trypsin is useful for the prevention and/or the treatment of disseminated intravascular coagulation, pancreatitis, severity in pancreatitis and multiple organ failure.

In the specifications of EP-A-588655 and 656349, it is disclosed that cetain amidinophenol compounds of the formula (IA) depicted hereinafter have an inhibitory activity on $PLA_2$ and an inhibitory activity on trypsin and are useful for the prevention and/or the treatment of various inflammatory or allergic diseases, disseminated intravascular coagulation, pancreatitis, severity in pancreatitis and multiple organ failure.

Several amidinophenol derivatives are known to be $LTB_4$ antagonists. They are disclosed in WO 94/11341, the specification of Japanese Patent Kokai No. 5-239008 and EP-518819. In these applications, it is disclosed that amidinophenyloxy (thio) alkyloxy (thio) benzamide is useful as an $LTB_4$ antagonist.

For example, it is described in the specification of EP-518819 that compounds of the formula (A):

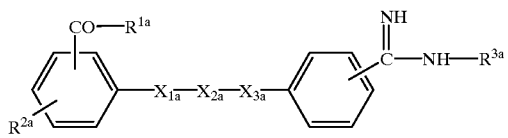

(A)

wherein
- $R^{1a}$ is amino which is mono- or disubstituted by a substituent selected from an aliphatic hydrocarbon radical, an araliphatic hydrocarbon radical, an aromatic radical, and a cycloaliphatic hydrocarbon radical or is amino which is disubstituted by a divalent aliphatic hydrocarbon radical;
- $R^{2a}$ is hydrogen, halogen, trifluoromethyl, an aliphatic hydrocarbon radical, or is hydroxy which is etherified by an aliphatic alcohol, araliphatic alcohol, or aromatic alcohol or which is esterified by an aliphatic or araliphatic carboxylic acid;
- $R^{3a}$ is hydrogen or an acyl radical which is derived from an organic carbonic acid, an organic carboxylic acid, a sulfonic acid, or a carbamic acid; $X_{1a}$ and $X_{3a}$, independently of one another, are oxygen (—O—) or sulphur (—S—);
- $X_{2a}$ is a divalent aliphatic hydrocarbon radical which may be interrupted by an aromatic radical;
- wherein the phenyl rings of formula (A) may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;
- wherein aryl moieties in the above definitions may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid; and
- wherein a cycloaliphatic hydrocarbon radical may be substituted by an aliphatic radical;

and pharmaceutically acceptable salts thereof are useful as $LTB_4$ antagonist.

3. Comparison with the Related Arts

In the amidinophenyloxy(thio)alkoxy(thio)benzamide compounds represented by EP-518819 as prior art, it can be seen that $-X_{1a}-X_{2a}-X_{3a}-$ must be —O(or S)-alkylene-O(or S)—, with the proviso that the alkylene may be interrupted by an aromatic group.

It has now been discovered that compounds in which it is essential that the amidinophenyl group is bonded to the phenyl group via an ester or amide group possess useful properties as $LTB_4$ antagonists and as inhibitors of phospholipase $A_2$ and/or trypsin.

SUMMARY OF THE INVENTION

The present invention relates to the discovery that amidinophenol derivatives defined by formulas (IA) and (IB) have a strong antagonistic activity on $LTB_4$ and thus are useful for the prevention or treatment of diseases induced by $LTB_4$.

The present invention also relates to the discovery that compounds of formula (IB) have an inhibitory activity on phospholipase $A_2$ and an inhibitory activity on trypsin and thus are useful in preventing or treating conditions associated with the activity of these enzymes, such as various inflammatory and allergic diseases, disseminated intravascular coagulation, pancreatitis, severity in pancreatitits and multiple organ failure.

Compunds of formula (IA) and processes for the preparation thereof are known and disclosed in EP-A-588655 and EP-A-656349. Compounds of formula (IB) are novel and described below.

DESCRIPTION OF THE INVENTION

The present invention relates to:
1) a new amidinophenol derivative of the formula (IB):

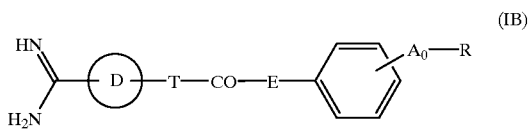

(IB)

wherein:

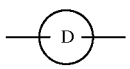

is a group of the formula:

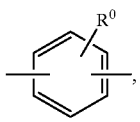

(i)

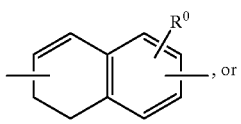

(ii)

, or

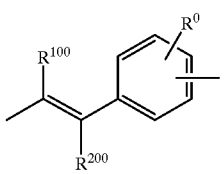

(iii)

wherein
- $R^0$ is hydrogen, C1–4 alkyl, or C1–4 alkoxy,
- T is NH or oxygen,
- E is a single bond, or a group of the formula:

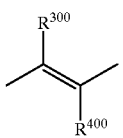

$A_0$ is selected from the group consisting of a single bond, C1–4 alkylene, -oxy-(C1–4)alkylene-, -thio-(C1–4) alkylene-, C2–8 alkenylene, and C2–8 alkenylene substituted by carboxy or C1–4 alkoxycarbonyl, $R^{100}$, $R^{200}$, $R^{300}$ and $R^{400}$ each independently, is hydrogen or C1–4 alkyl, R is a group of the formula:

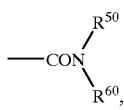 (i)

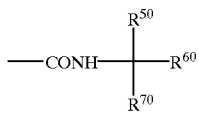 (ii)

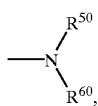 (iii)

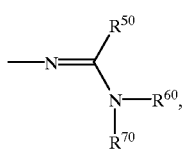 (iv)

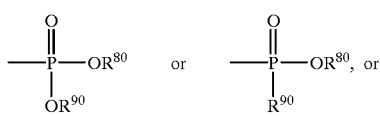 (v)

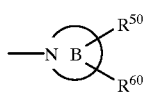 (vi)

wherein the group:

is a 4–10 membered hetero ring containing one or two nitrogen atoms, $R^{50}$, $R^{60}$ and $R^{70}$ each independently, is,
(i) hydrogen,
(ii) C1–8 alkyl,
(iii) C2–8 alkenyl
(iv) —COOR$^{110}$, wherein $R^{110}$ is hydrogen, C1–4 alkyl, or C1–4 alkyl substituted by phenyl,
(v) —(C1–8 alkylene)-COOR$^{110}$, wherein $R^{110}$ has the same meaning as defined above,
(vi) —(C2–8 alkenylene)-COOR$^{110}$, wherein $R^{110}$ has the same meaning as defined above,
(vii) C4–7 cycloalkyl,
(viii) —(C1–4 alkylene)-(4–7 membered hetero ring containing one oxygen),
(ix) —(C1–4 alkylene)-(4–7 membered hetero ring containing one nitrogen),
(x) phenyl,
(xi) C1–8 alkyl substituted by one or two phenyl,
(xii) —(C1–4 alkylene)-O-benzoyl,
(xiii) —(C1–4 alkylene)-CONH—(C1–4 alkylene)-NR$^{120}$R$^{130}$,
(xiv) —(C1–4 alkylene)-COO—(C1–4 alkylene)-NR$^{120}$R$^{130}$,
(xv) —(C1–4 alkylene)-COO-amidinophenyl,
(xvi) —(C1–4 alkylene)-CONH—(C1–4 alkyl substituted by one or two COOR$^{110}$), wherein $R^{110}$ has the same meaning as defined above,
(xvii) —(C1–4 alkylene)-CONR$^{120}$R$^{130}$, or
(xviii) (C1–4) alkoxy (C1–4) alkyl, $R^{80}$ and $R^{90}$ each independently, is C1–4 alkyl or —(C1–4 alkylene)-phenyl, $R^{120}$ and $R^{130}$ each independently, is hydrogen, C1–4 alkyl, or C2–8 alkenyl, with the provisos that:

(1) $R^{50}$ and $R^{60}$ in the formulae (i) and (iii), and $R^{50}$, $R^{60}$ and $R^{70}$ in the formulae (ii) and (iv), do not represent hydrogen at the same time, (2) when at least one substituent in $R^{50}$, $R^{60}$, $R^{70}$ and $A_0$ represents a substituent containing —COO-t-Bu, the other groups do not represent groups containing carboxy, (3) $R^{120}$ and $R^{130}$ do not represent hydrogen at the same time, (4) when
T is oxygen, the group:

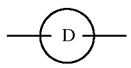

is the formula (i) as hereinbefore described,
E is a single bond,
$A_0$ is a single bond, C1–4 alkylene or vinylene which is optionally substituted by one or two C1–4 alkyl, and
R is the formula (i) as described above, then at least one group in $R^{50}$, $R^{60}$ and $R^{70}$ is
(viii) —(C1–4 alkylene)-(4–7 membered hetero ring containing one oxygen),
(ix) —(C1–4 alkylene)-(4–7 membered hetero ring containing one nitrogen),
(x) phenyl,
(xi) C1–8 alkyl which is substituted by one or two phenyl,
(xii) —(C1–4 alkylene)-O-benzoyl,
(xiii) —(C1–4 alkylene)-CONH—(C1–4 alkylene)-NR$^{120}$R$^{130}$,
(xiv) —(C1–4 alkylene)-COO—(C1–4 alkylene)-NR$^{120}$R$^{130}$,
(xv) —(C1–4 alkylene)-COO-amidinophenyl,
(xvi) —(C1–4 alkylene)-CONH—(C1–4 alkyl substituted by one or two COOR$^{110}$), wherein $R^{110}$ has the same meaning as defined above,
(xvii) —(C1–4 alkylene)-CONR$^{120}$R$^{130}$, or
(xviii) (C1–4) alkoxy (C1–4) alkyl;

(5) when
T is oxygen, the group

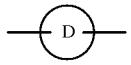

is the formula (i) as hereinbefore defined,
E is a single bond,
$A_0$ is a single bond, C1–4 alkylene or vinylene optionally substituted by one or two C1–4 alkyl, and
R is the formula (ii) as defined above,
then $R^{50}$, $R^{60}$ and $R^{70}$ do not represent hydrogen;
and non-toxic salts thereof or non-toxic acid addition salts thereof, 2) a method for the prevention and/or treatment of diseases induced by leukotriene B$_4$, which comprises the administration to a patient of an effective amount of a compound of the formula (IA):

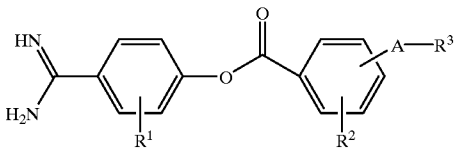

wherein
R$^1$ and R$^2$ each independently, is:
(i) hydrogen, or
(ii) —COOR$^4$ wherein R$^{14}$ is C1–3 alkyl;
A is
(i) a single bond,
(ii) C1–4 alkylene, or
(iii) —C(R$^5$)=C(R$^6$)—, wherein R$^5$ and R$^6$ each independently, is hydrogen or C1–4 alkyl;
R$^3$ is
(i) —CON(R$^7$)R$^8$,
(ii) —CONR$^9$—CH(R$^7$)R$^8$, or
(iii)

wherein R$^7$ and R$^8$ each independently, is
(1) hydrogen,
(2) phenyl,
(3) —(C1–4 alkylene)-phenyl,
(4) —(C1–4 alkylene)-phenyl is substituted by one or two —R$^{11}$—COOR$^{12}$, wherein R$^{11}$ is a single bond or C1–8 alkylene, and R$^{12}$ is hydrogen or C1–4 alkyl,
(5) C1–5 alkyl,
(6) C2–10 alkenyl containing one to three double bonds,
(7) —R$^{11a}$—COOR$^{12}$,
  wherein R$^{11a}$ is
  (a) a single bond,
  (b) C1–8 alkylene,
  (c) C2–8 alkenylene, or
  (d) C4–8 alkenylene in which one or two carbon atoms in the main chain are replaced by sulfur, and R$^{12}$ has the same meaning as defined above, or
(8) C3–7 cycloalkyl;
R$^9$ is
(1) hydrogen,
(2) —R$^{11}$—COOR$^{12}$, wherein R$^{11}$ and R$^{12}$ have the same meanings as defined above, or
(3) C2–6 alkoxyalkyl;
the group:

is a 4–7 membered mono hetero ring contain one or two nitrogen;
R$^{10}$ is
(1) hydrogen, or
(2) —(C1–4 alkylene)-phenyl, with the proviso that:
  (1) both R$^7$ and R$^8$ do not represent hydrogen at the same time,
  (2) when at least one group in R$^7$, R$^8$, and R$^9$ represent the group containing —COO-t-Bu, the other groups do not represent the groups containing carboxy;
or non-toxic salts thereof and non-toxic acid-addition salts thereof,
3) processes for the preparation of the compound of the formula (IB),
4) LTB$_4$ antagonists containing a compound of the formula (IB) and non-toxic salts thereof or non-toxic acid addition salts thereof, as the active ingredient, and
5) phospholipaseA$_2$ and trypsin inhibitors containing a compound of the formula (IB) and non-toxic salts thereof or non-toxic acid addition salts thereof, as the active ingredient.

The compounds of the invention may form hydrates; it is to be understood that such hydrates form part of the present invention and that references to the compounds in this specification, including the accompanying claims, are to be understood as embracing the hydrates.

It will be understood that formulae (i) and (ii) for the symbol R may overlap: formula (ii) should be construed as excluding those groupings already embraced by formula (i).

Throughout the specification, it will be understood by those skilled in the art that all isomers are included in the present invention. For example, the alkyl, alkoxy, alkylene, alkenylene and alkynylene groups include straight-chain and also branched-chain ones, and the double bonds in the alkenylene group include E, Z and EZ mixtures. Accordingly, all isomers produced by the existence of asymmetric carbon atoms are included in the present invention when branched-chain alkyl, alkoxy, alkylene, alkenylene and alkynylene are present.

Explanation of various symbols in the formula (IB) is given below.

The C1–3 alkyl group means methyl, ethyl, propyl and the isomers thereof. C1–4 alkyl group means methyl, ethyl, propyl, butyl, and the isomers thereof. C1–5 alkyl group means methyl, ethyl, propyl, butyl, pentyl and the isomers thereof.

C1–4 alkylene group means methylene, ethylene, trimethylene, tetramethylene and the isomers thereof. C1–8 alkylene group means methylene, ethylene, trimethylene, tetramethylene, pentamethylene, hexamethylene, heptamethylene, octamethylene, and the isomers thereof.

C2–6 alkoxyalkyl group means ethylene, trimethylene, tetramethylene, pentamethylene, hexamethylene and the isomers thereof which are interrupted by oxygen except at their end. Representative of such alkoxyalkyl groups are: —CH$_2$—O—CH$_2$—, —CH$_2$—O—(CH$_2$)$_2$—, —(CH$_2$)$_2$—O—CH$_2$—, —CH$_2$—O—(CH$_2$)$_3$—, —(CH$_2$)$_2$—O—(CH$_2$)$_2$—, —(CH$_2$)$_3$—O—CH$_2$—, —CH$_2$—O—(CH$_2$)$_4$—, —(CH$_2$)$_2$—O—(CH$_2$)$_3$—, —(CH$_2$)$_3$—O—(CH$_2$)$_2$—, —(CH$_2$)$_4$—O—CH$_2$—, —CH$_2$—O—(CH$_2$)$_5$—, —(CH$_2$)$_2$—O—(CH$_2$)$_4$—, —(CH$_2$)$_3$—O—(CH$_2$)$_3$—, —(CH$_2$)$_4$—O—(CH$_2$)$_2$—, —(CH$_2$)$_5$—O—CH$_2$—.

C4–8 alkenylene group means tetramethylene, pentamethylene, hexamethylene, heptamethylene, octamethylene in which a —CH$_2$—CH$_2$— grouping (which is not at either end of the group) is replaced by a double bond.

C2–8 alkenylene group containing one to three double bonds means ethylene, trimethylene, tetramethylene, pentamethylene, hexamethylene, heptamethylene or octamethylene in which one to three groupings —CH$_2$—CH$_2$— (except those at each end of the group) are replaced by double bonds.

C3–7 cycloalkyl group means cyclopropyl, cyclobutyl, cyclopentyl, cyclohexyl and cycloheptyl.

The 4–7 membered hetero ring containing one or two nitrogen means, for example, pyrrolyl, pyrrolidinyl, imidazolyl, imidazolidinyl, pyridinyl, piperidinyl, pyrazinyl, piperazinyl or pyrimidinyl.

Further explanation of various symbols in the formula (IB) is given below.

In the formula (IB), C1–4 alkyl represented by $R^0$, $R^{100}$, $R^{200}$, $R^{300}$, $R^{400}$, $R^{50}$, $R^{60}$, $R^{70}$, $R^{80}$, $R^{90}$, $R^{120}$ and $R^{130}$, and that in $R^0$, $R^{100}$, $R^{200}$, $R^{300}$, $R^{400}$, $R^{50}$, $R^{60}$, $R^{70}$, $R^{80}$, $R^{90}$, $R^{120}$ and $R^{130}$, means methyl, ethyl, propyl, butyl and the isomers thereof.

In the formula (IB), C1–4 alkyl represented by $R^0$ and $A_O$, and that in $R^0$ and $A_O$ means methoxy, ethoxy, propoxy, butoxy and the isomers thereof.

In the formula (IB), C1–4 alkylene represented by $A_O$, and that in $A_O$, means methylene, ethylene, trimethylene, tetramethylene and the isomers thereof.

In the formula (IB), C2–8 alkenylene represented by $A_O$, and that in $A_O$, means ethylene, trimethylene, tetramethylene, pentamethylene, hexamethylene, heptamethylene, octamethylene and the isomers thereof, having one, two or three double bonds.

In the formula (IB), C1–8 alkyl represented by $R^{50}$, $R^{60}$ and $R^{70}$, and that in $R^{50}$, $R^{60}$ and $R^{70}$, means methyl, ethyl, propyl, butyl, pentyl, hexyl, heptyl, octyl and the isomers thereof.

In the formula (IB), C2–8 alkenyl represented by $R^{50}$, $R^{60}$ and $R^{70}$, and that in $R^{50}$, $R^{60}$ and $R^{70}$, mean methyl, ethyl, propyl, butyl, pentyl, hexyl, heptyl, octyl and the isomers thereof, having one, two or three double bonds.

In the formula (IB), 4–7 cycloalkyl represented by $R^{50}$, $R^{60}$ and $R^{70}$, and that in $R^{50}$, $R^{60}$ and $R^{70}$, mean cyclobutyl, cyclopentyl, cyclohexyl and cycloheptyl.

In the formula (IB), examples of the 4–7 membered hetero ring containing one oxygen (which may be partially or fully saturated) represented by $R^{50}$, $R^{60}$ and $R^{70}$, and that in $R^{50}$, $R^{60}$ and $R^{70}$, are furyl, pyranyl, dihydrofuryl, dihydropyranyl, tetrahydrofuryl and tetrahydropyranyl.

In the formula (IB), examples of the 4–7 membered hetero ring containing one nitrogen (which may be partially or fully saturated) represented by $R^{50}$, $R^{60}$ and $R^{70}$, and that in $R^{50}$, $R^{60}$ and $R^{70}$, are pyrrolyl, pyridinyl, piperidinyl, pyrrolinyl, pyrrolidinyl and dihydropyridinyl.

In the formula (IB), when R is the formula represented by (vi), examples of the 4–10 membered hetero ring containing one or two nitrogen, (which may be partially or fully saturated) are pyrrolyl, pyridinyl, pyrrolinyl, pyrrolidinyl, dihydropyridinyl, imidazolyl, piperidinyl, imidazolinyl, imidazolidinyl, pyrimidinyl, pyridazinyl, pyrazinyl, indolyl and tetrahydroindolyl.

Preferred Compound

Preferred formula (IB) compounds of the present invention are those described in the Examples and the following compounds.

TABLE 1

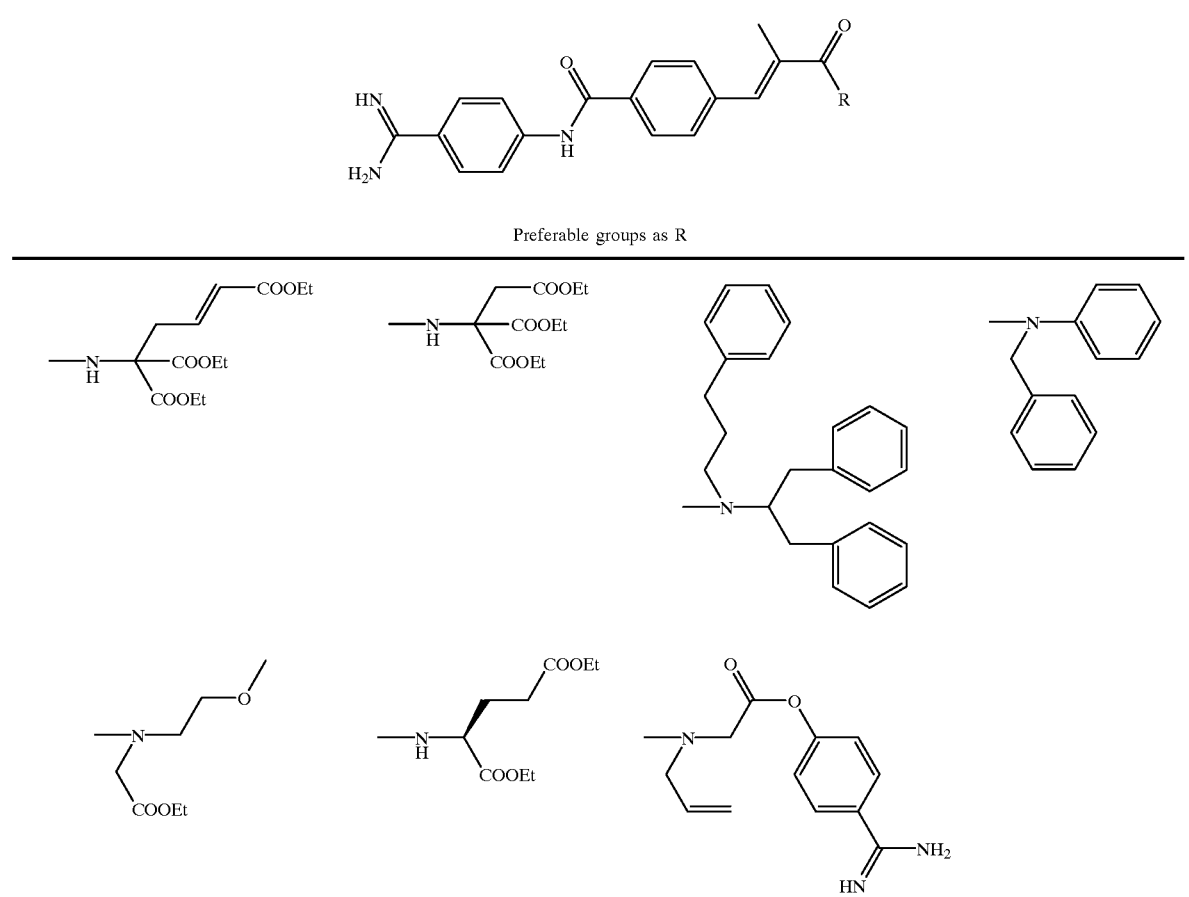

Preferable groups as R

TABLE 1-continued
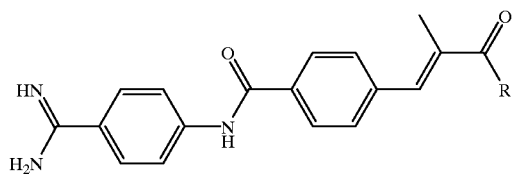
Preferable groups as R
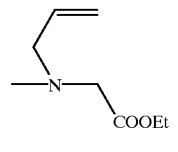 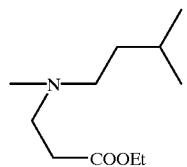
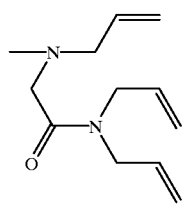 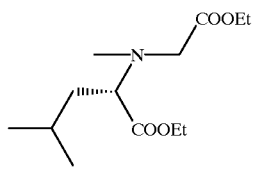
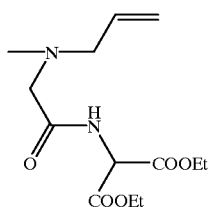
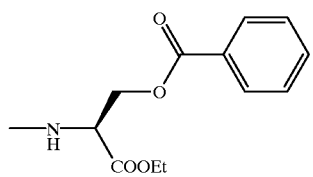 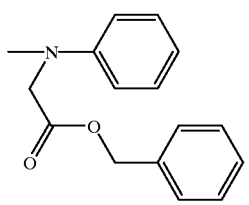 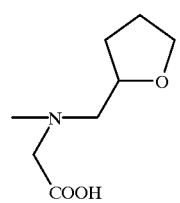 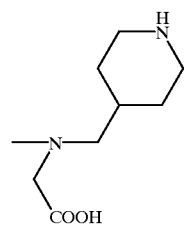
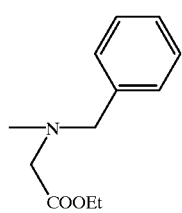 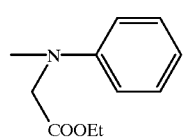 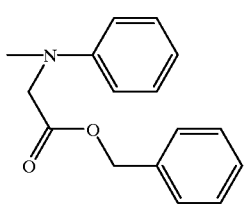
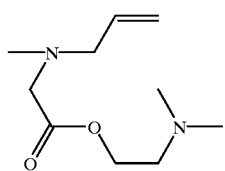 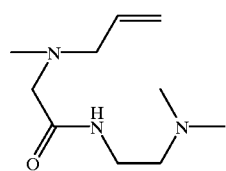

TABLE 2
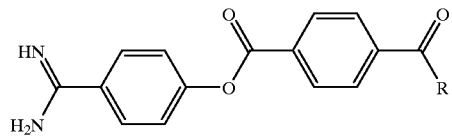
Preferable groups as R
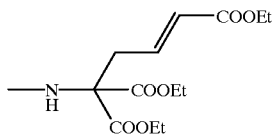 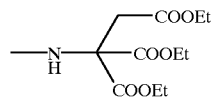 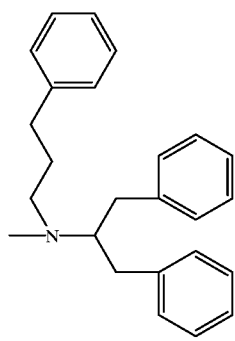 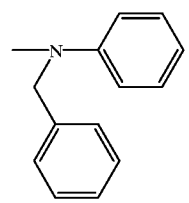
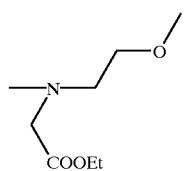 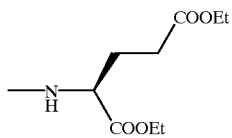 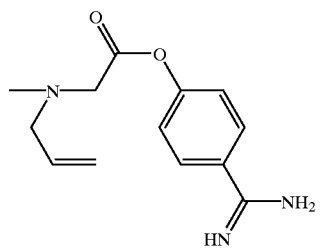
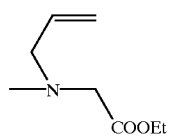 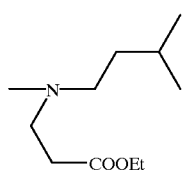
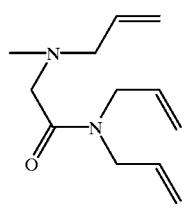 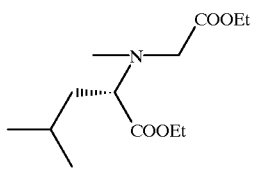
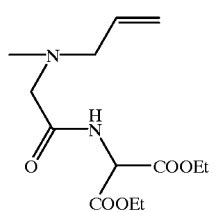

TABLE 2-continued
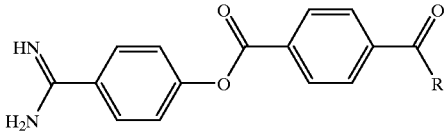
Preferable groups as R
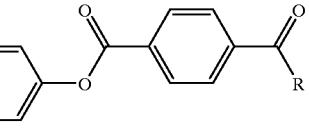
TABLE 3
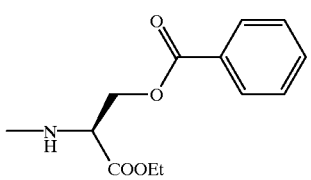
Preferable groups as R
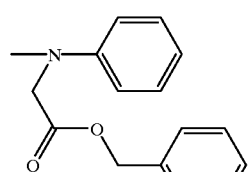

TABLE 3-continued
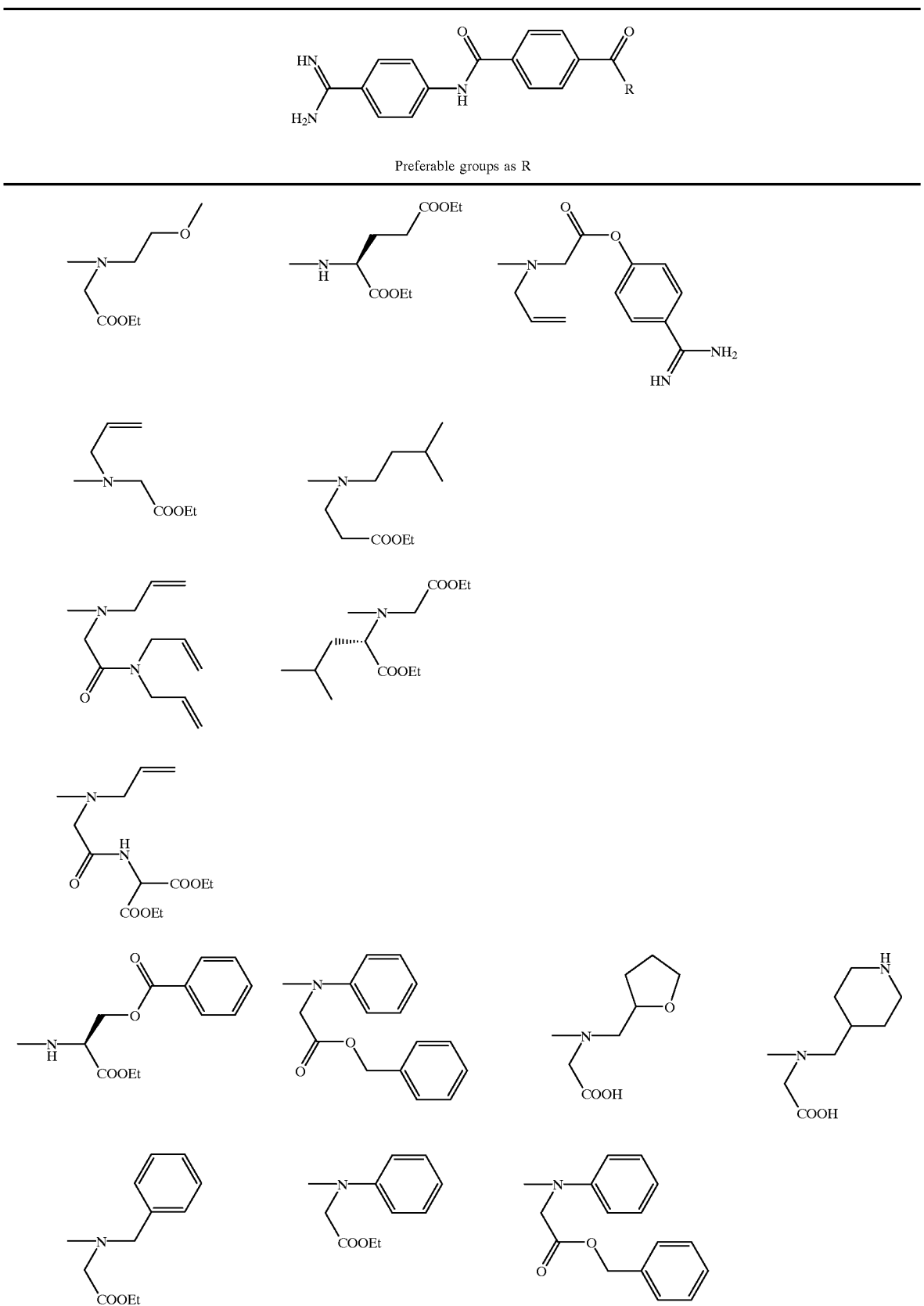

TABLE 3-continued
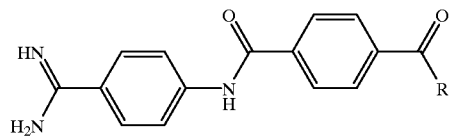
Preferable groups as R
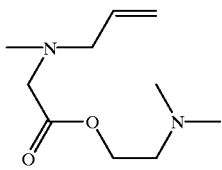 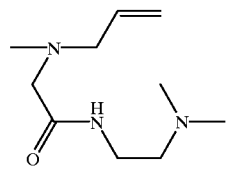
TABLE 4
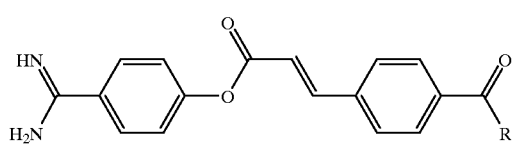
Preferable groups as R
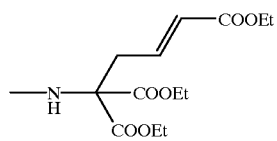 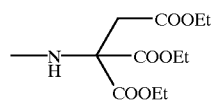 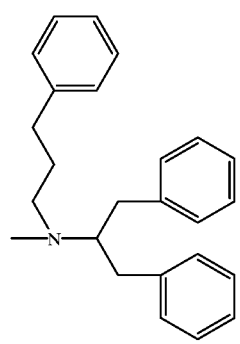 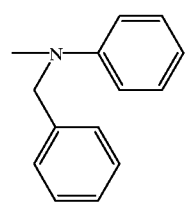
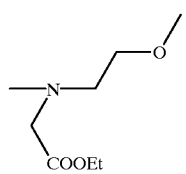 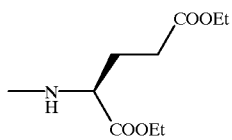 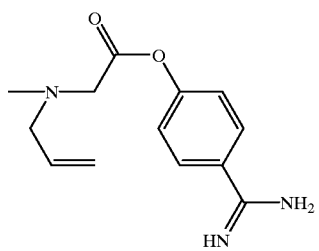
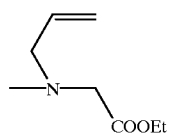 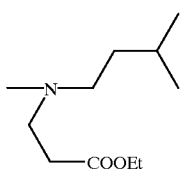

TABLE 4-continued
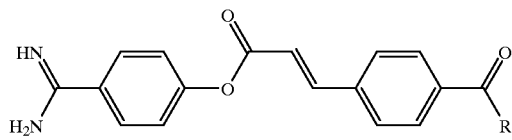
Preferable groups as R
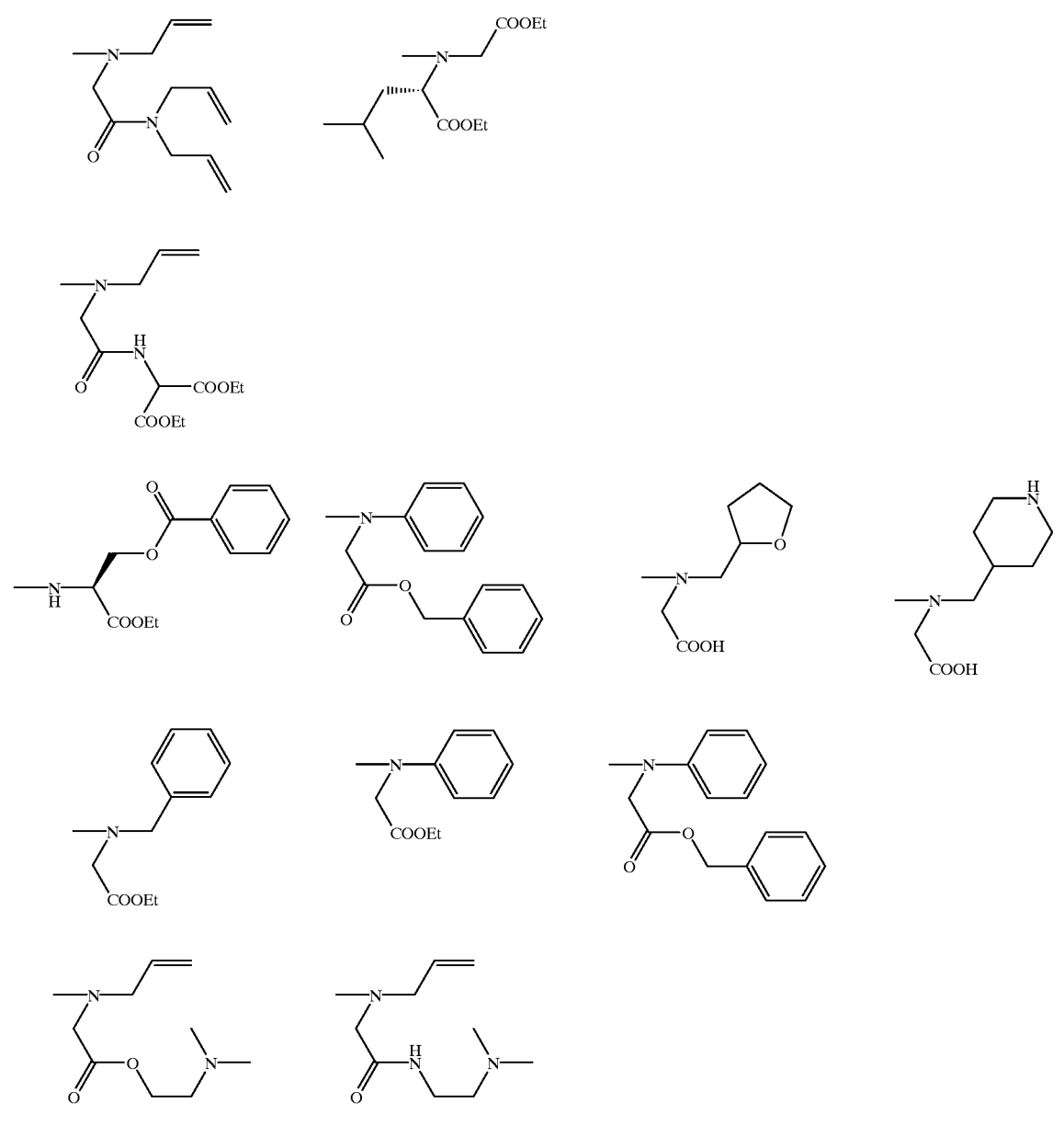

TABLE 5
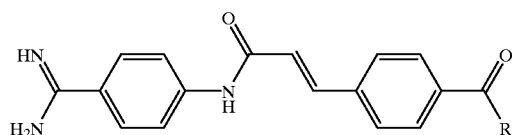
Preferable groups as R
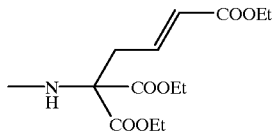 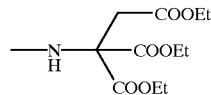 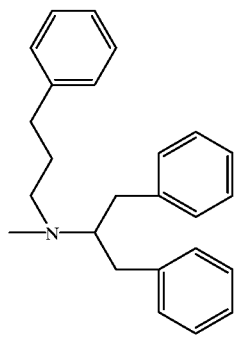 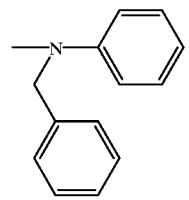
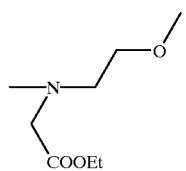 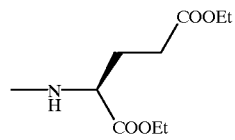 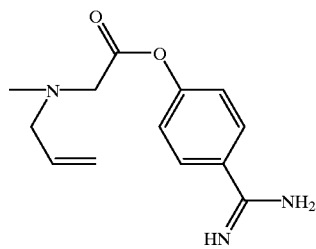
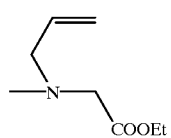 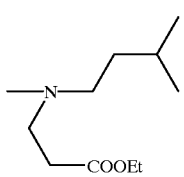
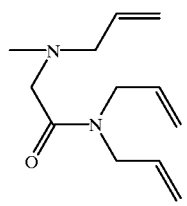 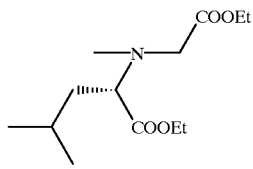
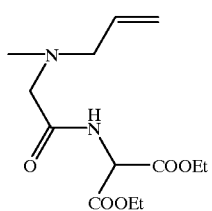

TABLE 5-continued
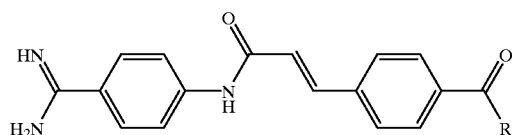
Preferable groups as R
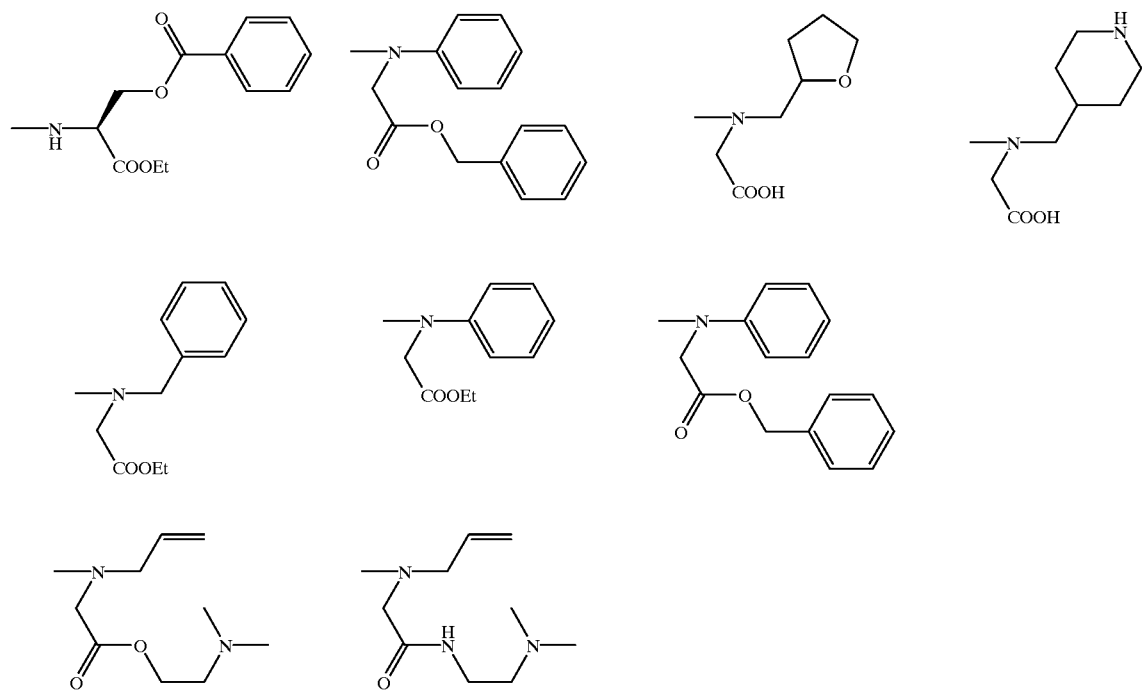
TABLE 6
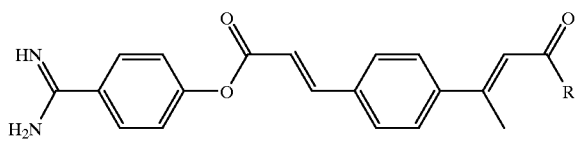
Preferable groups as R
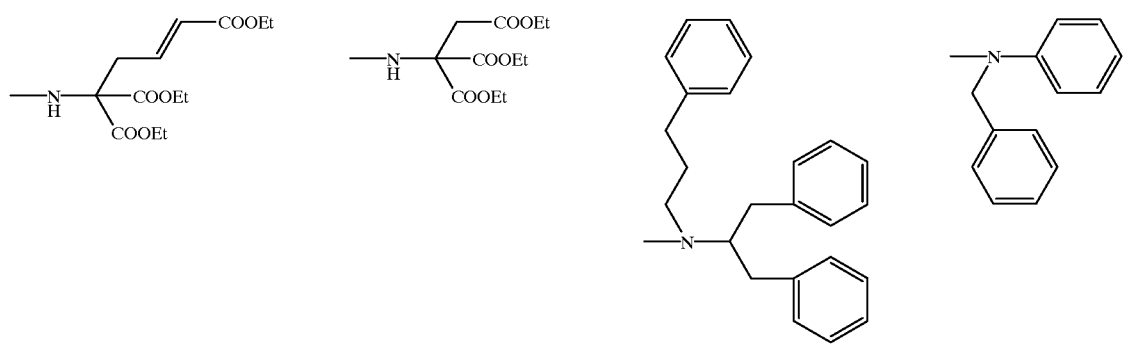

TABLE 6-continued
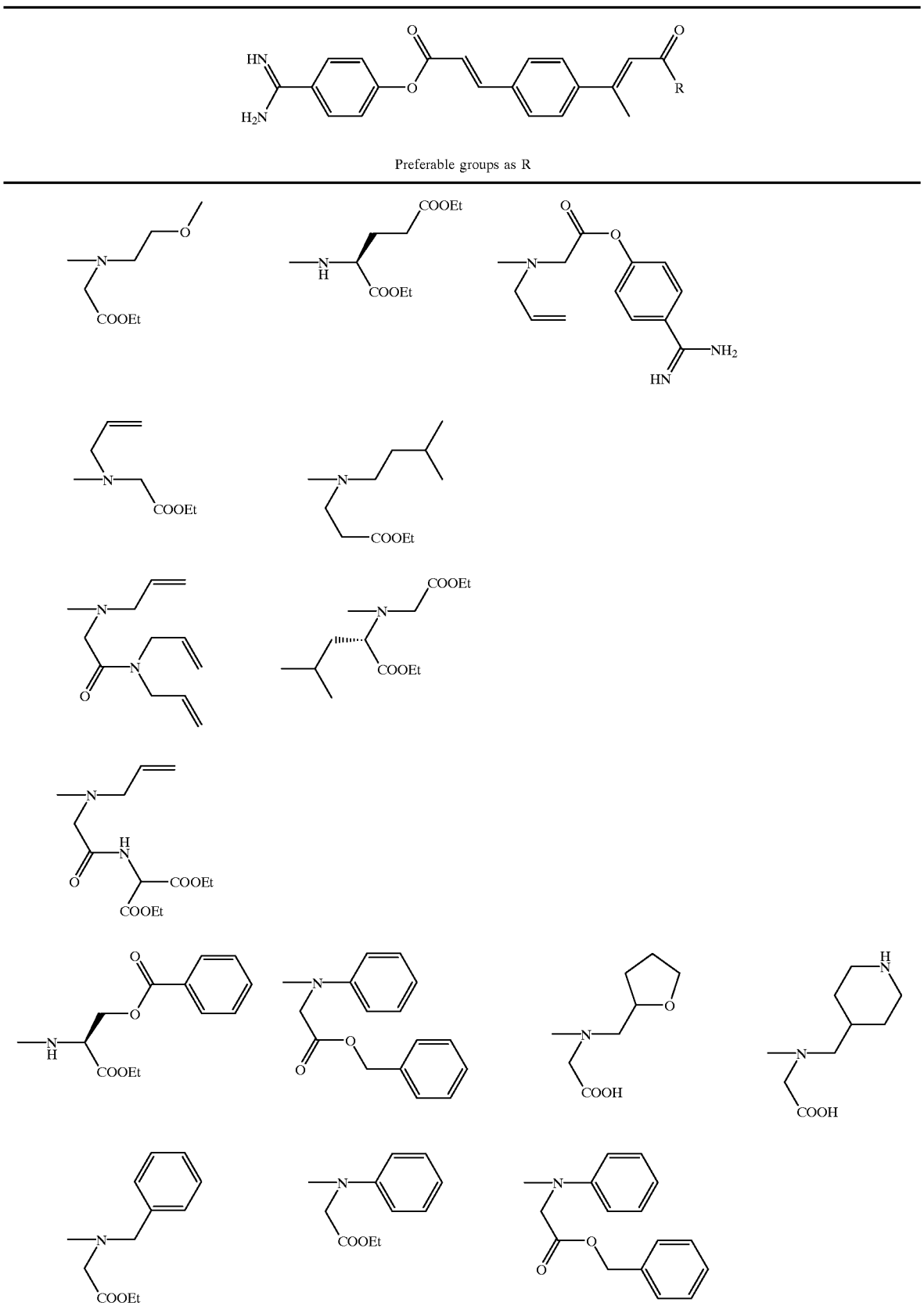
Preferable groups as R

TABLE 6-continued
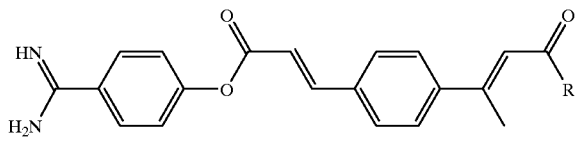
Preferable groups as R
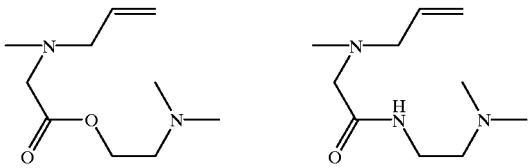
TABLE 7
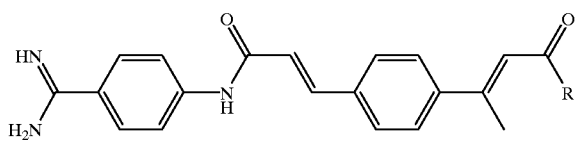
Preferable groups as R
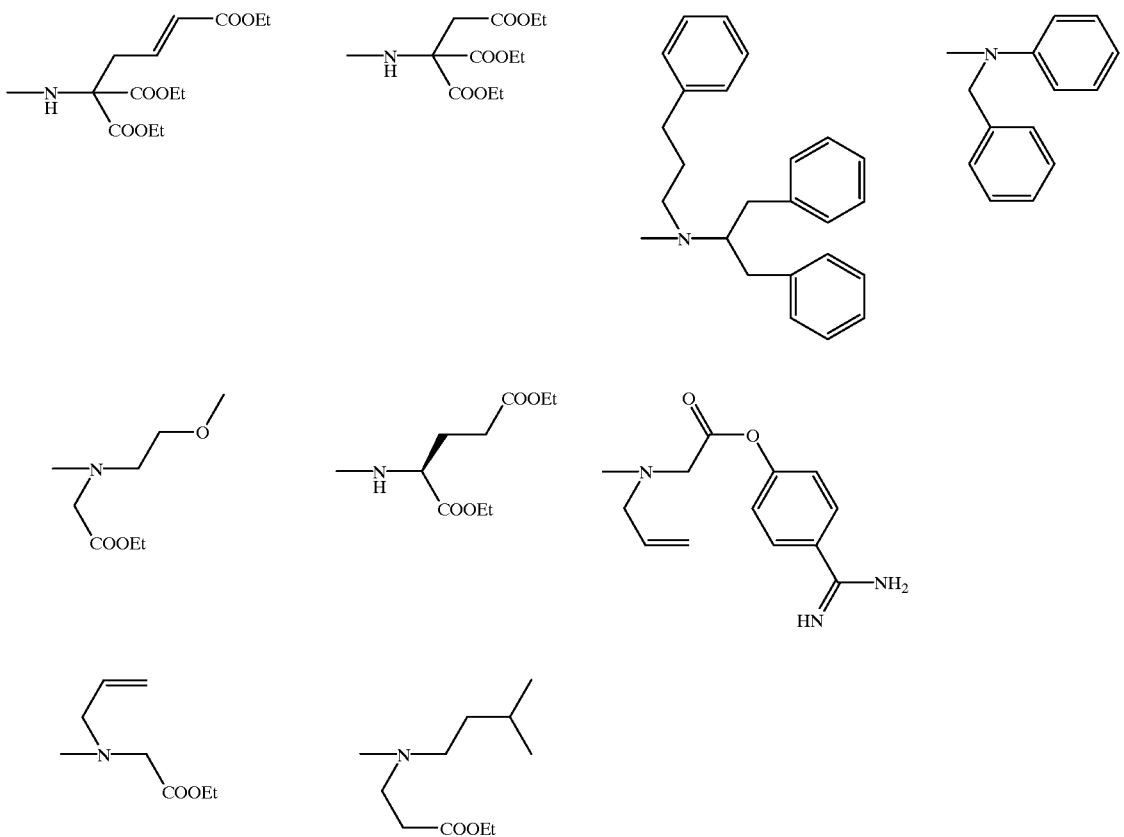

TABLE 7-continued
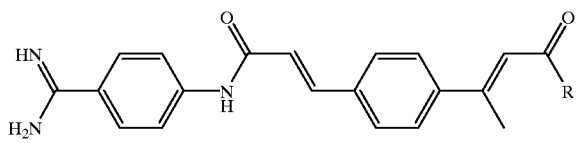
Preferable groups as R
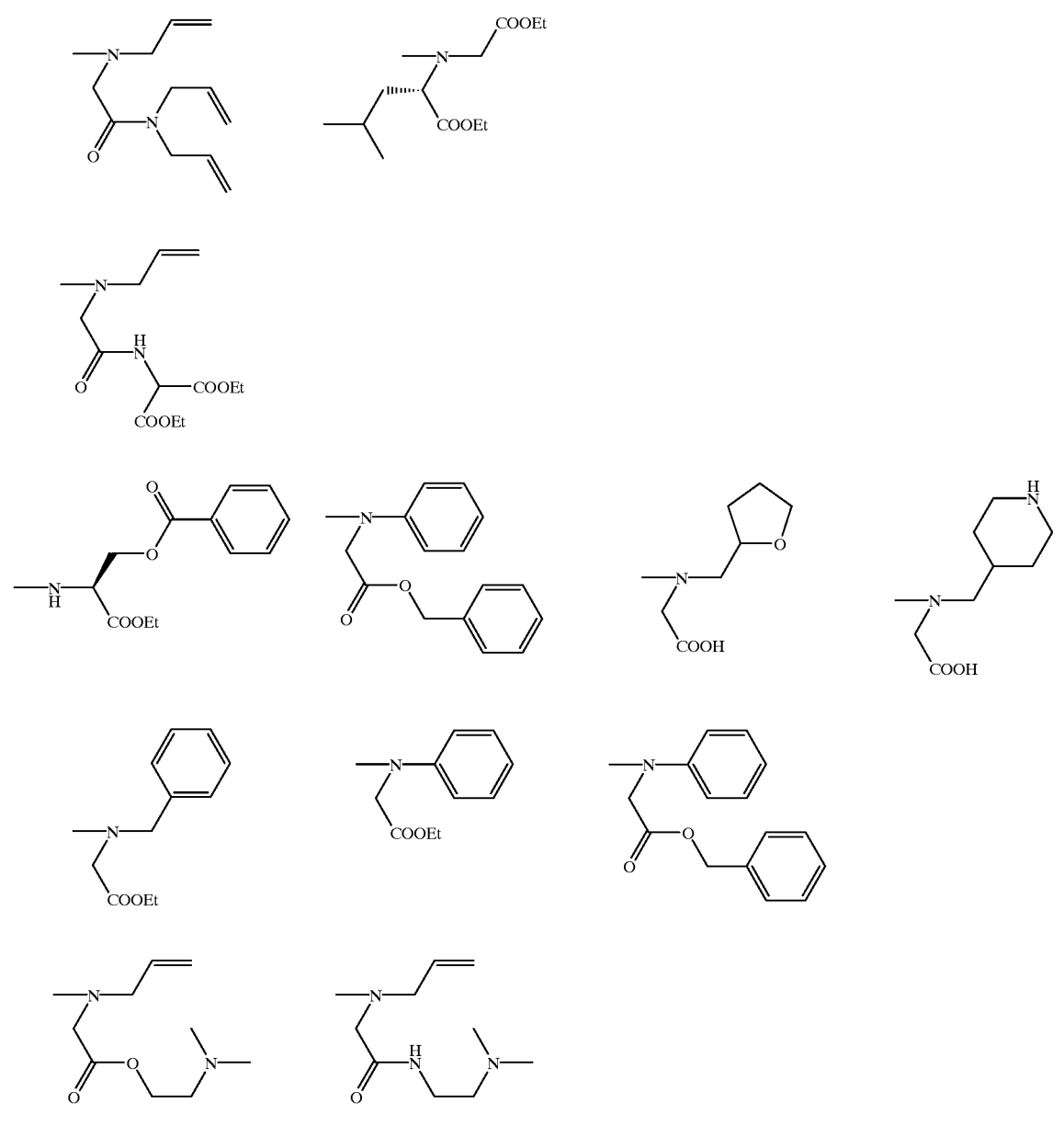

TABLE 8
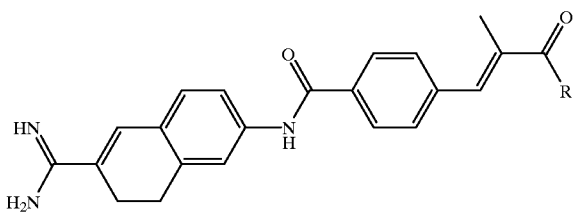
Preferable groups as R
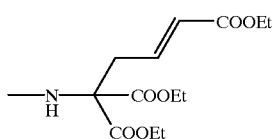 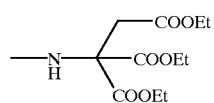 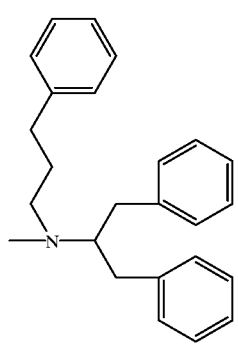 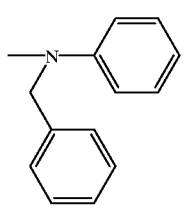
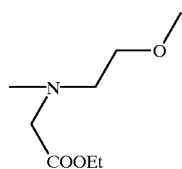 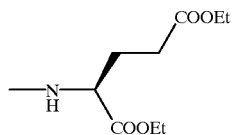 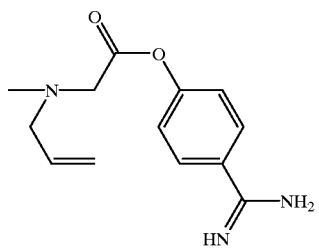
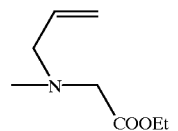 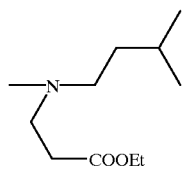
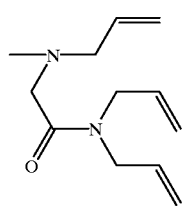 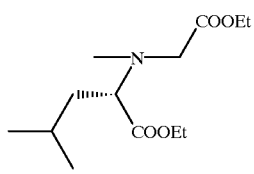
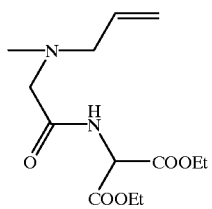

TABLE 8-continued
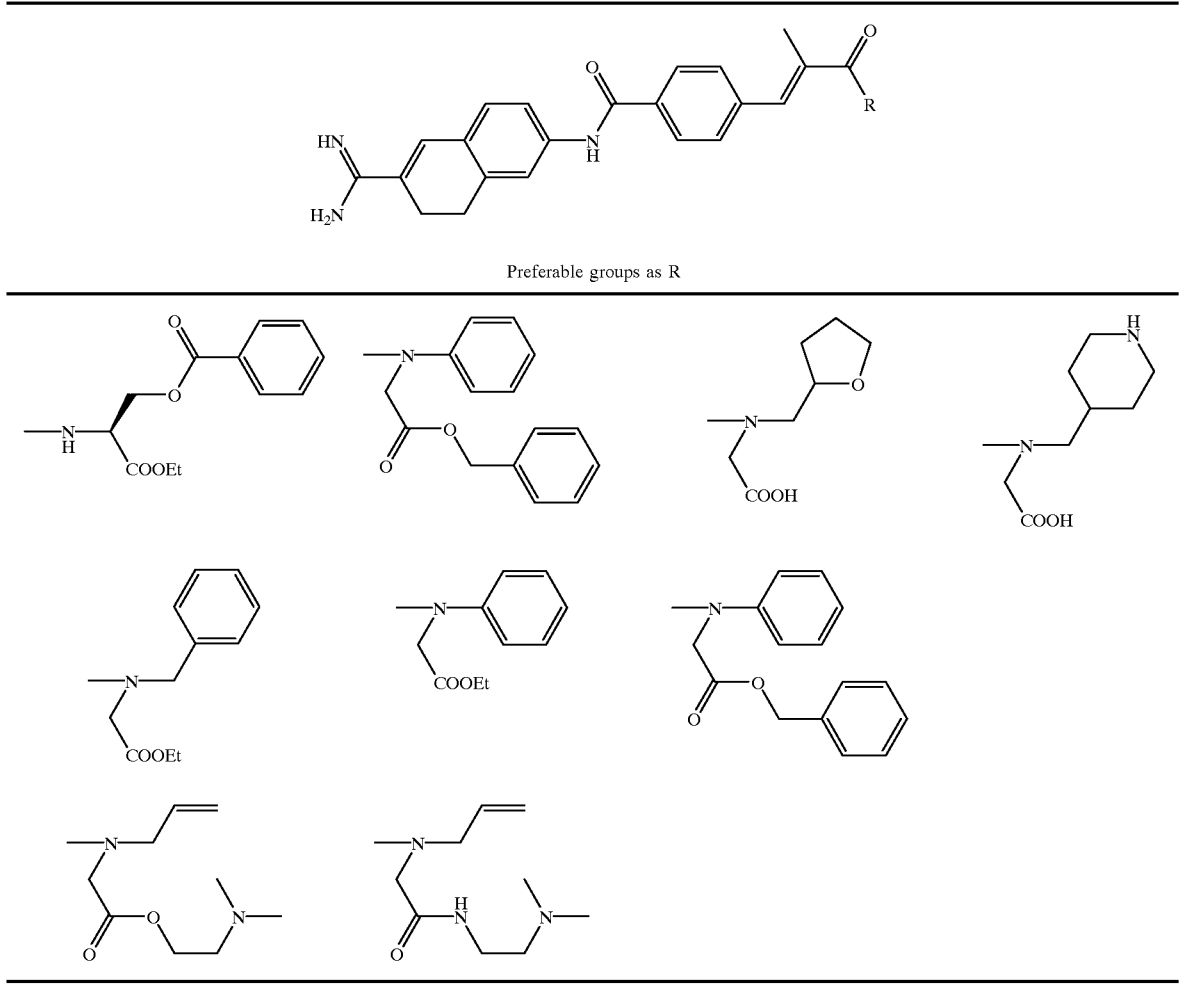
Preferable groups as R
TABLE 9
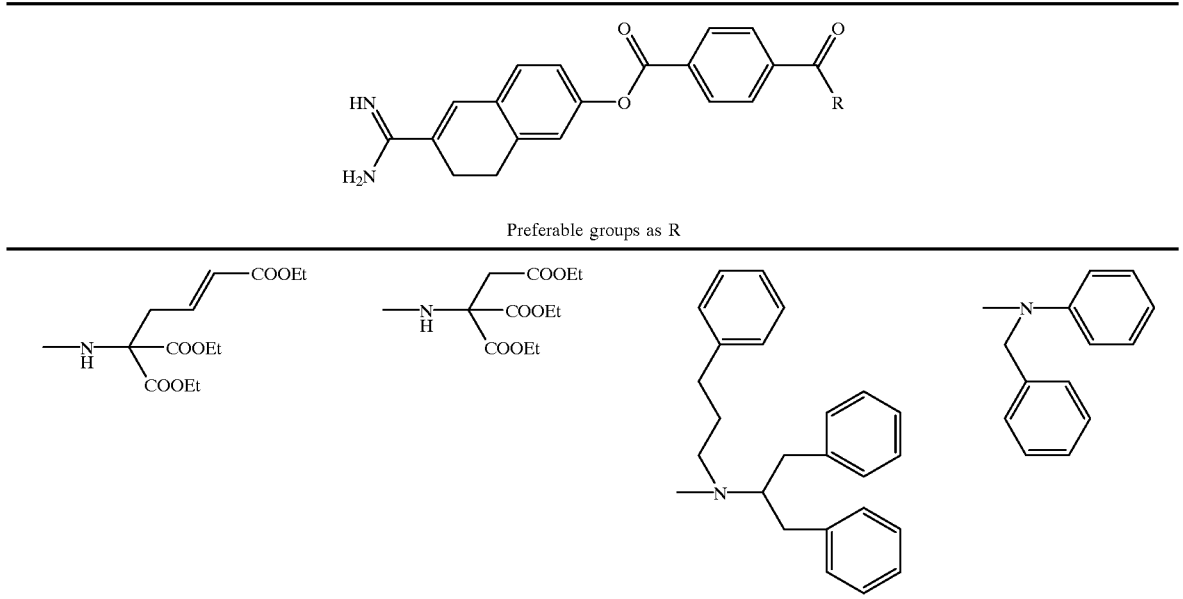
Preferable groups as R TABLE 9-continued
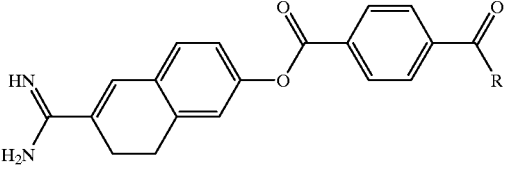
Preferable groups as R

TABLE 9-continued
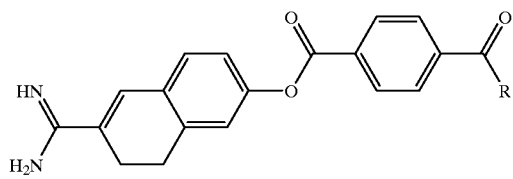
Preferable groups as R
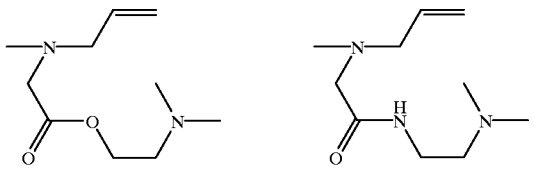
TABLE 10
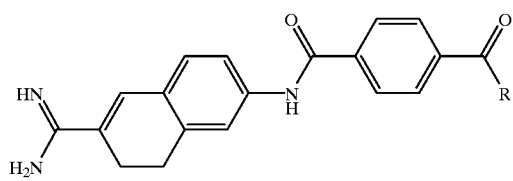
Preferable groups as R
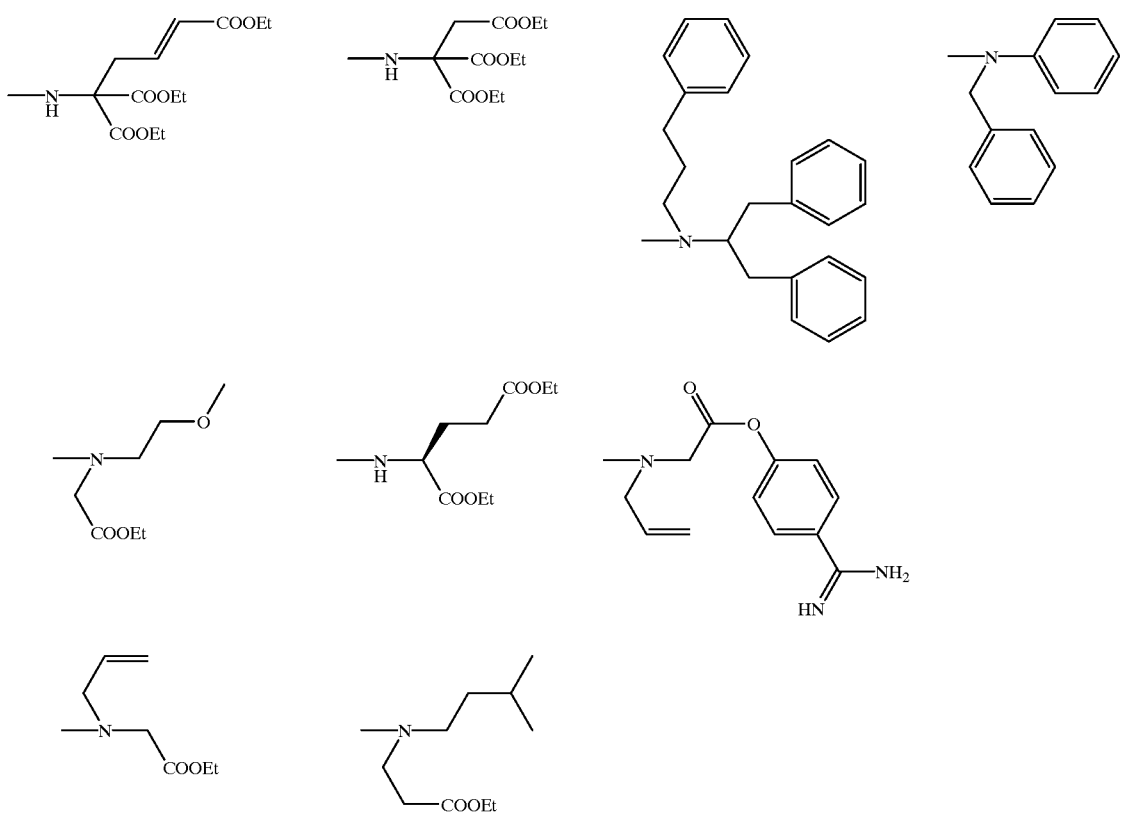

TABLE 10-continued
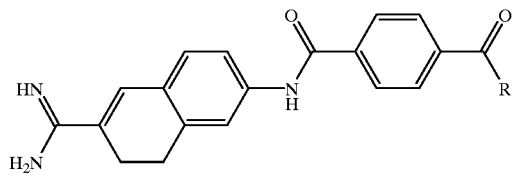
Preferable groups as R
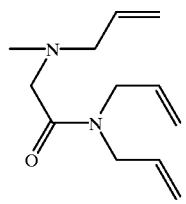 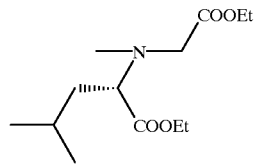
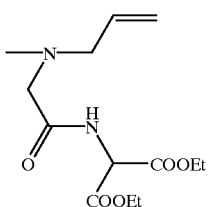
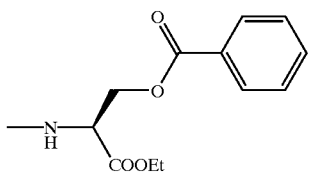 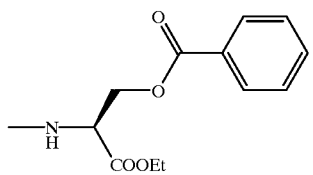 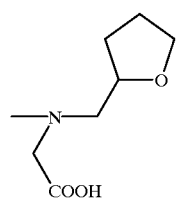 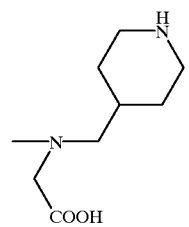
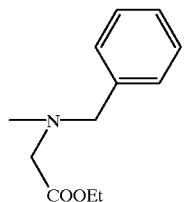 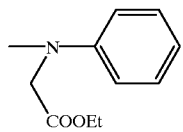 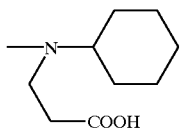
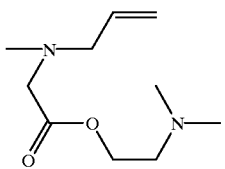 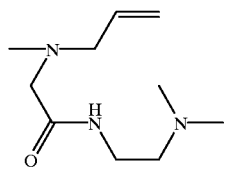

TABLE 11
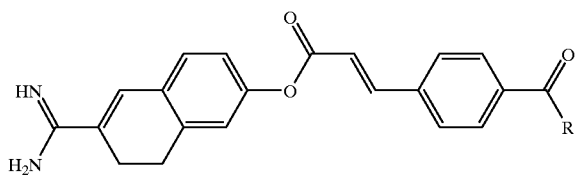
Preferable groups as R
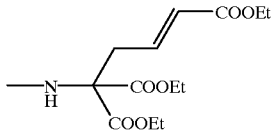 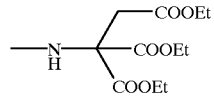 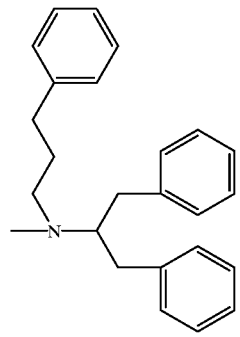 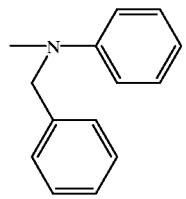
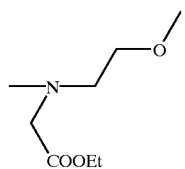 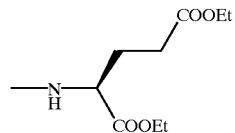 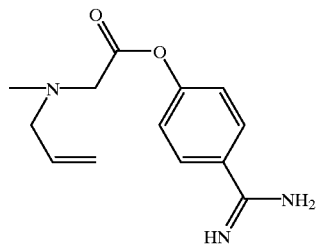
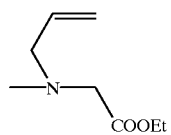 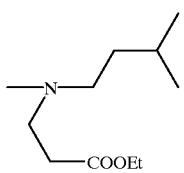
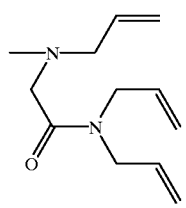 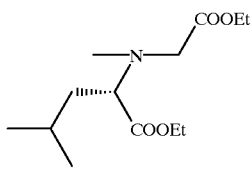
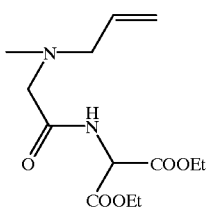

TABLE 11-continued
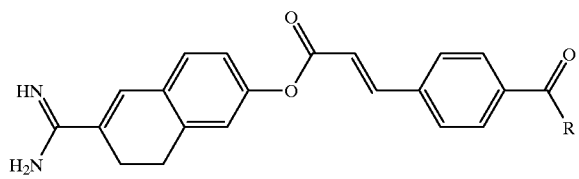
Preferable groups as R
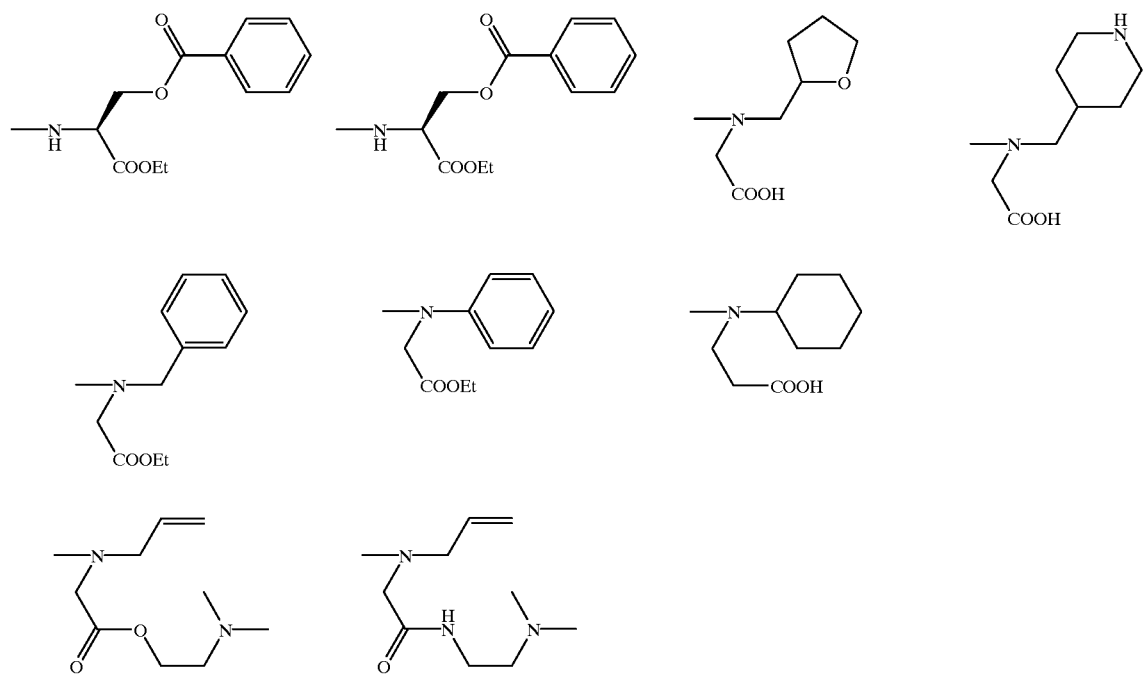
TABLE 12
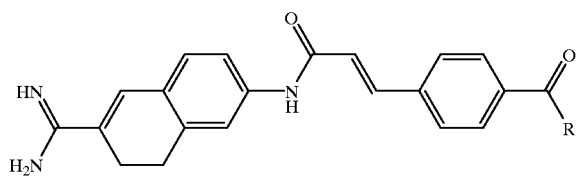
Preferable groups as R
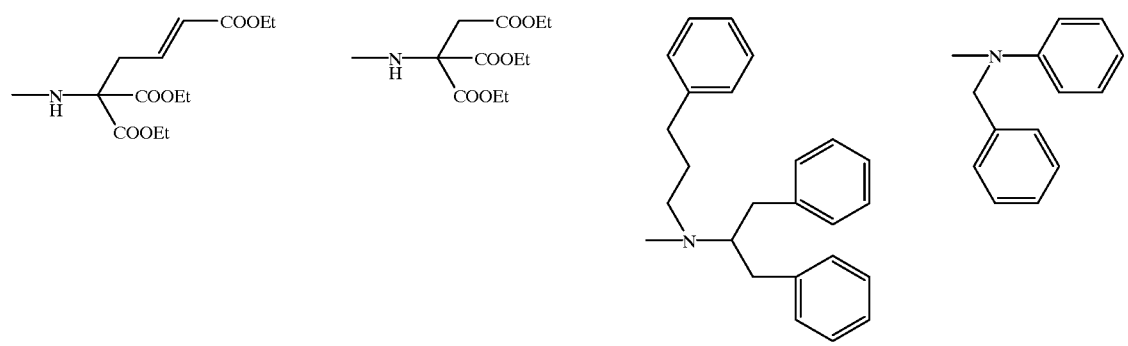

TABLE 12-continued
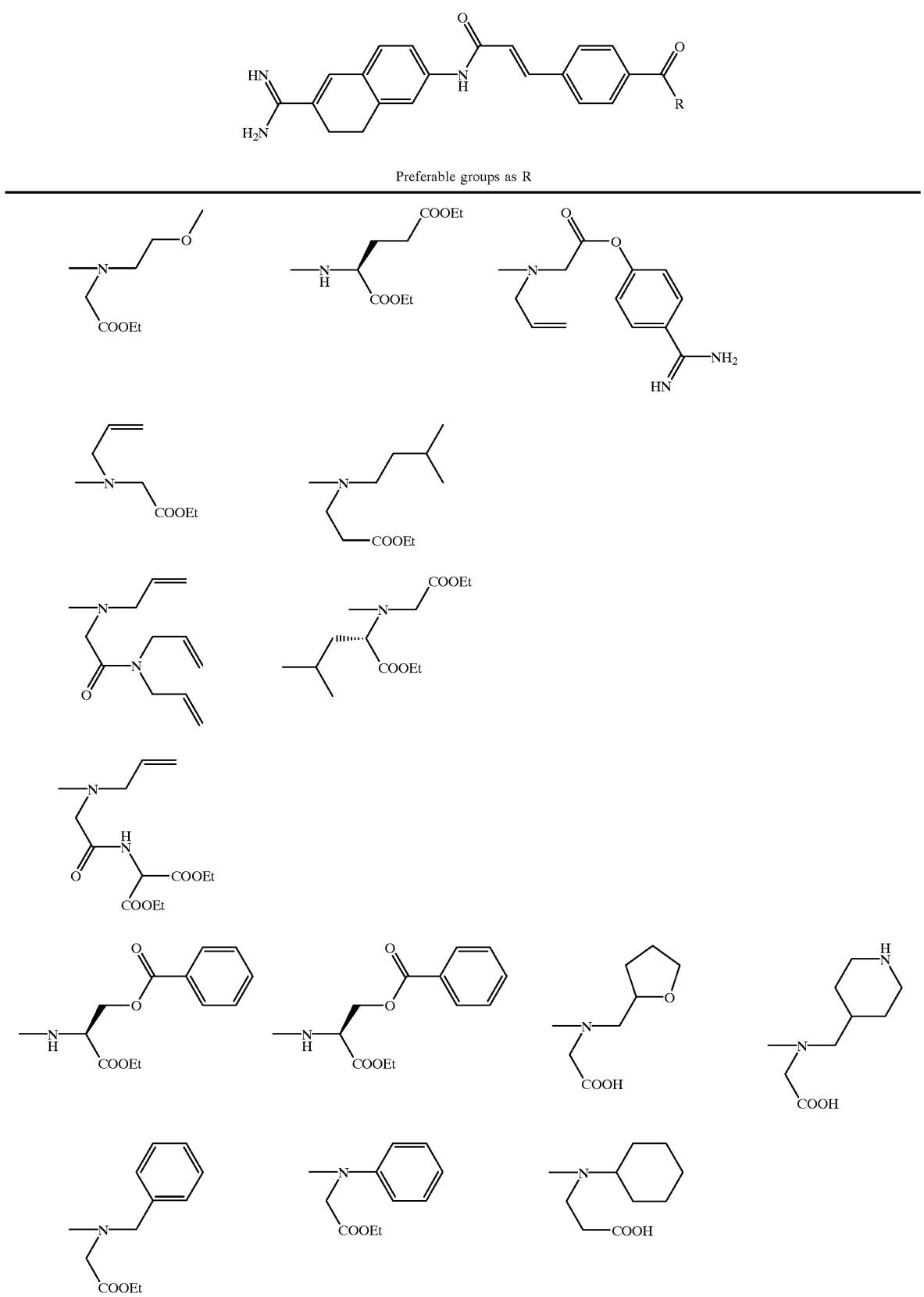
Preferable groups as R

TABLE 12-continued
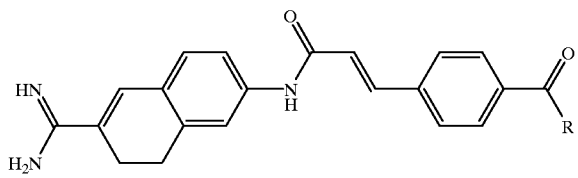
Preferable groups as R
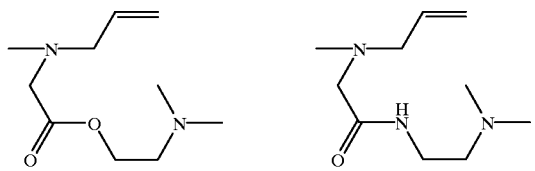
TABLE 13
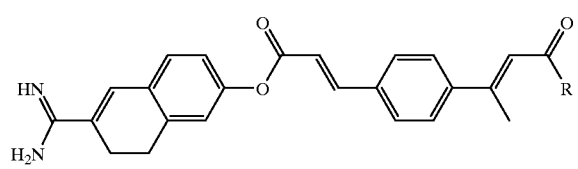
Preferable groups as R
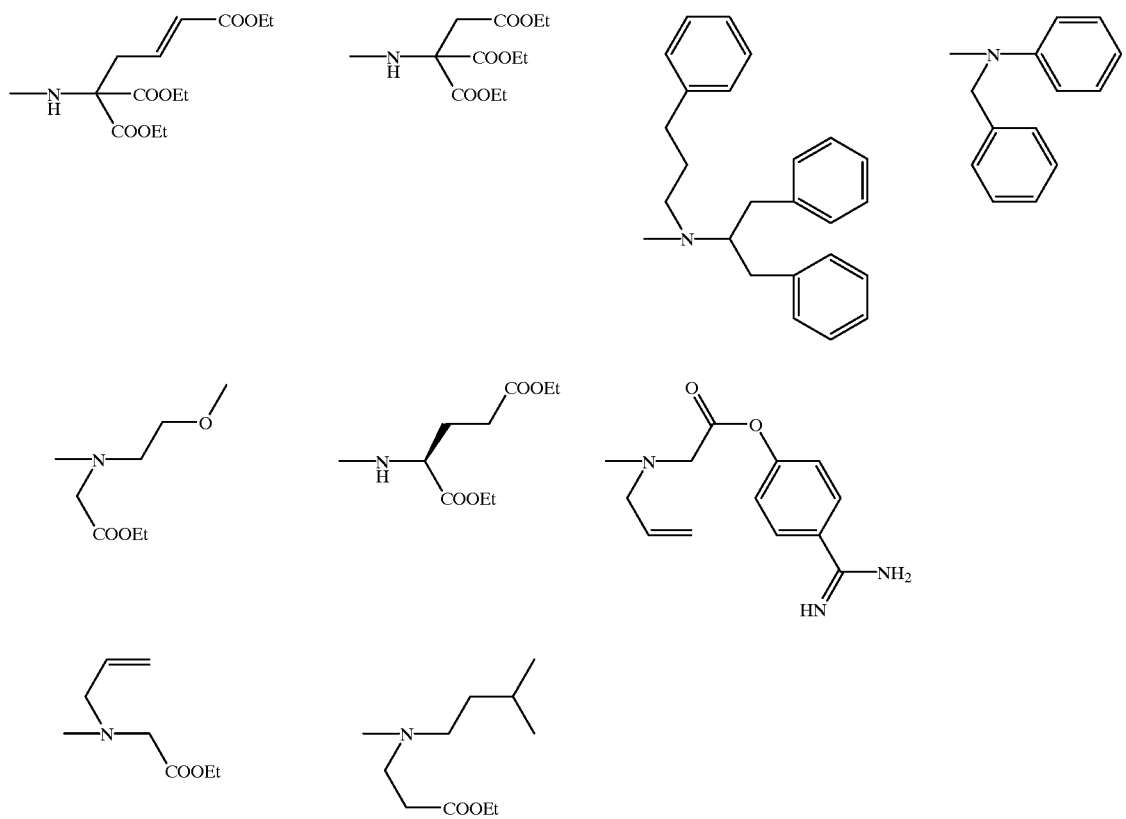

TABLE 13-continued
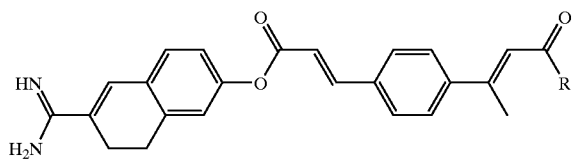
Preferable groups as R
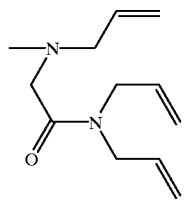 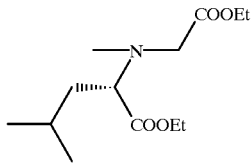
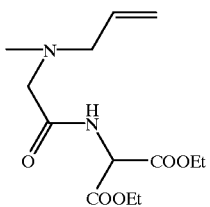
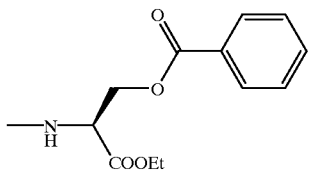 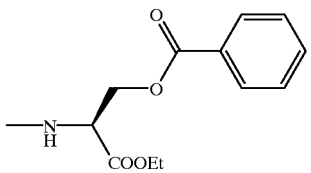 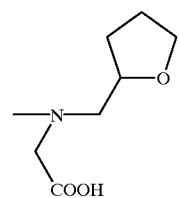 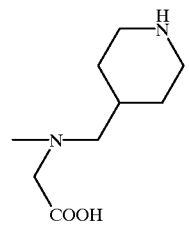
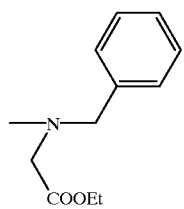 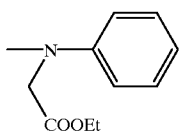 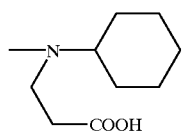
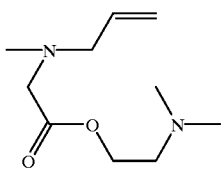 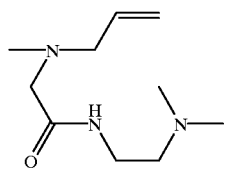

TABLE 14
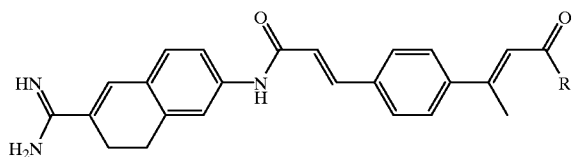
Preferable groups as R
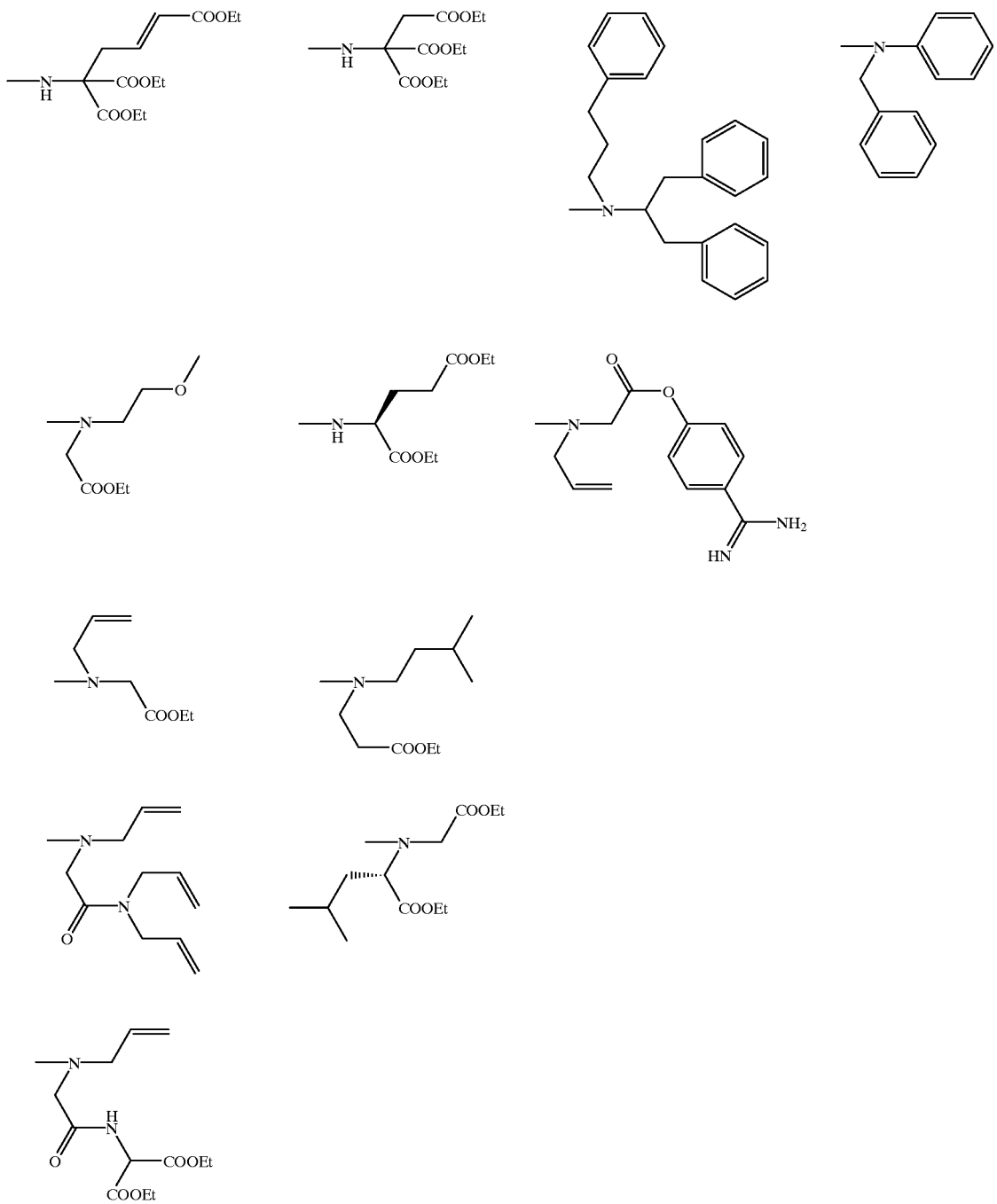

TABLE 14-continued
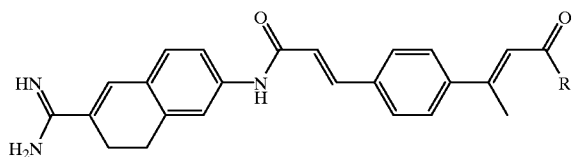
Preferable groups as R
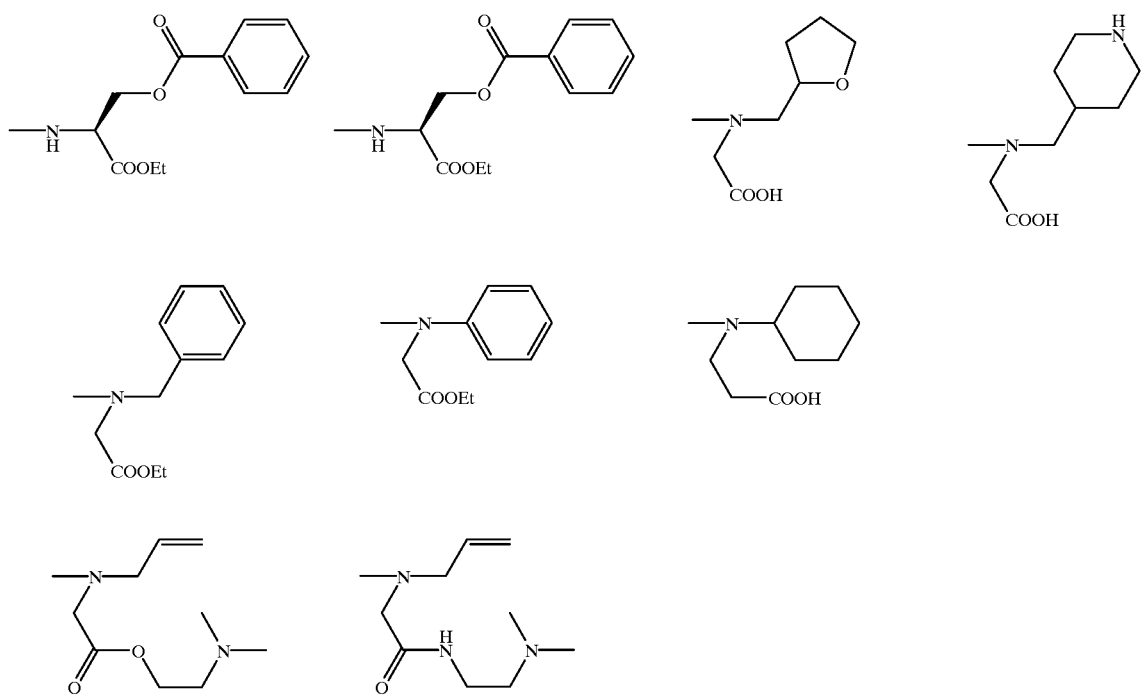
TABLE 15
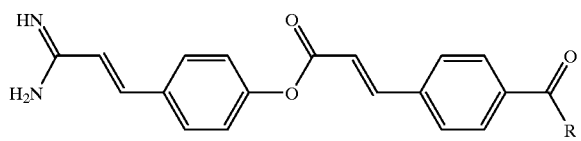
Preferable groups as R
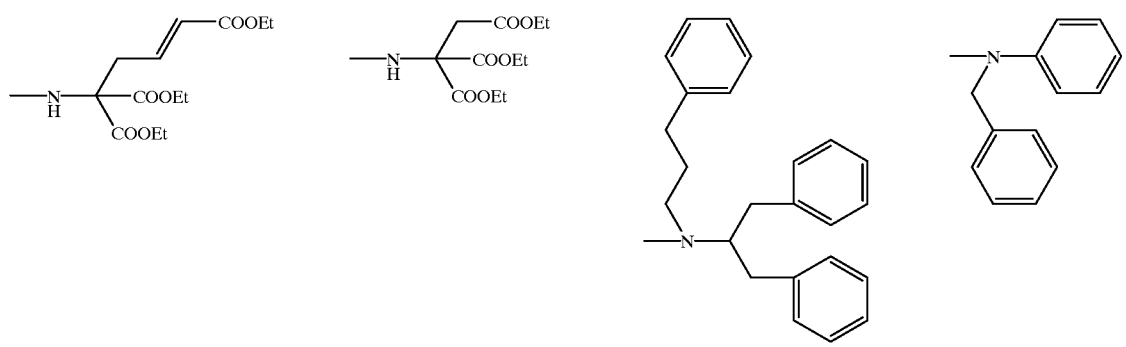

TABLE 15-continued
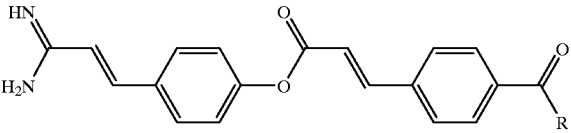
Preferable groups as R
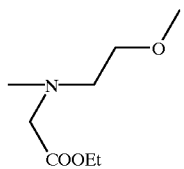

TABLE 15-continued
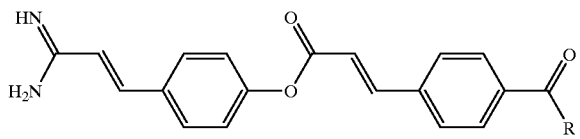
Preferable groups as R
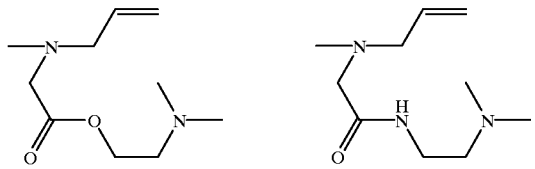
TABLE 16
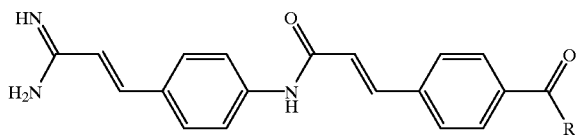
Preferable groups as R
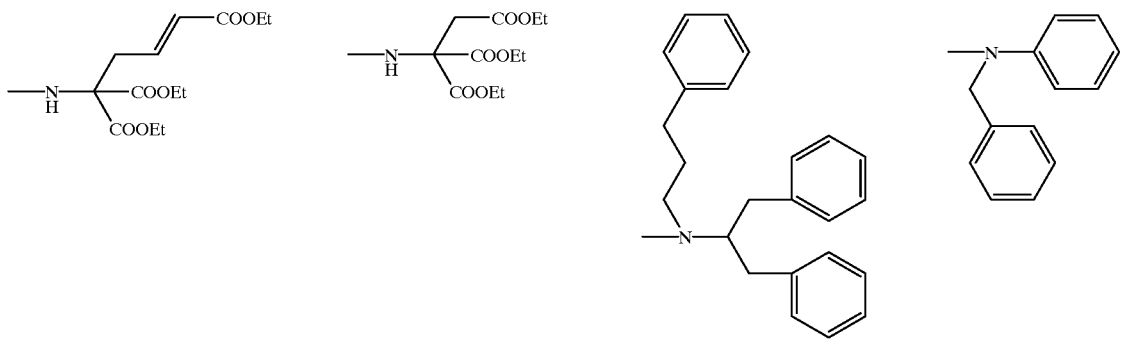
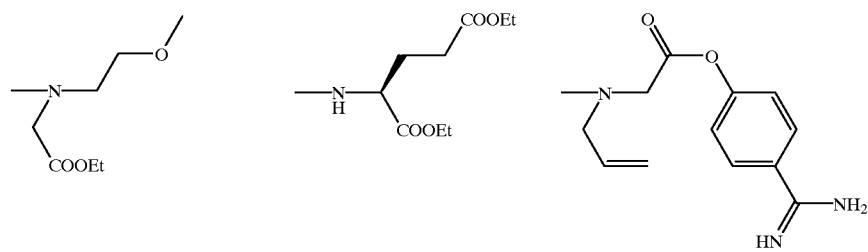
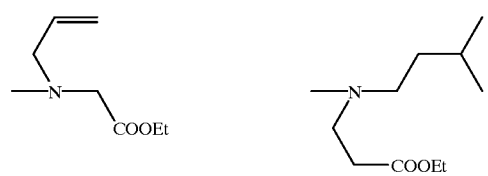

TABLE 16-continued

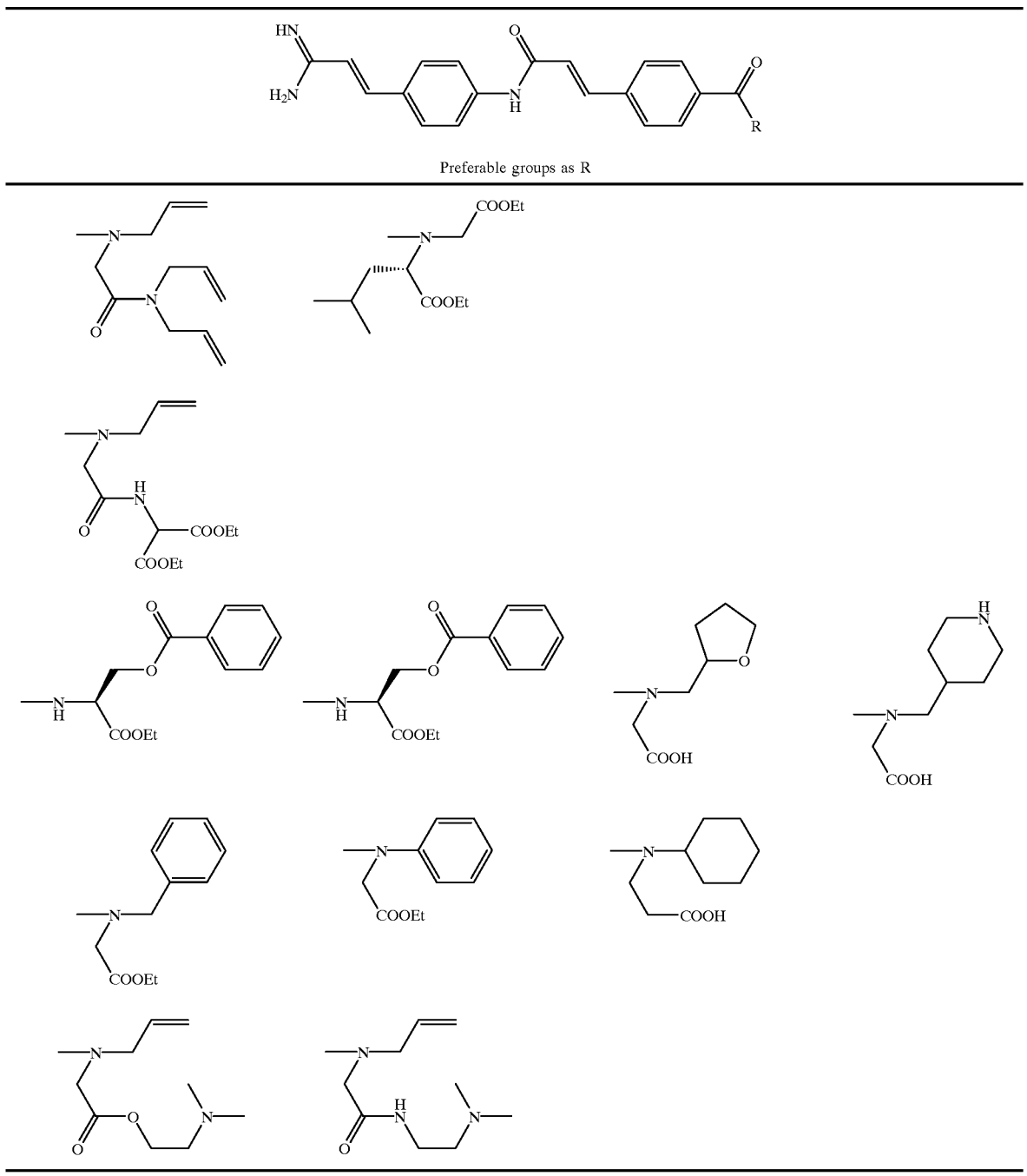

Pharmaceutical compositions of the present invention can be prepared using one active ingredient or two or more active ingredients.

Salts and Acid-addition Salts

Compounds of the formulae (IA) and (IB) of the present invention may be converted into the corresponding salts and acid-addition salts by known methods. Nontoxic and water-soluble salts are preferred.

Suitable salts include the salts of alkali metals (sodium, potassium etc.), alkaline-earth metal (calcium, magnesium etc.), ammonium salts, salts of pharmacoligically acceptable organic amines (tetramethyl ammonium, triethylamine, methylamine, dimethylamine, cyclopentylamine, benzylamine, phenetylamine, piperidine, monoethanolamine, diethanolamine, tris (hydroxymethyl) aminomethane, lysine, arginine, N-methyl-D-glucane etc).

Suitable acid-addition salts include the salts with inorganic acids such as hydrochloric acid, and the salts with organic acids such as acetic acid, trifluoroacetic acid, lactic acid, tartaric acid, oxalic acid, fumaric acid, maleic acid, citric acid, benzoic acid, methanesulfonic acid, ethanesulfonic acid, benzenesulfonic acid, toluenesulfonic acid, isethionic acid, glucuronic acid and gluconic acid. Preferred salts include the salts with acids such as hydrochloric acid, methanesulfonic acid, acetic acid and trifluoroacetic acid.

Preparation of Compounds

The compounds of the formula (IA) may be prepared by methods known per se, as defined in published applications EP-A-588655 and EP-A-656349. The formula (1B) compounds of the present invention may be prepared by forming an ester or amide bond between a compound of the formula (II):

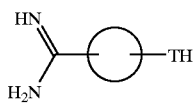

(II)

(wherein the various symbols have the same meanings as hereinbefore defined) with a compound of the formula (III):

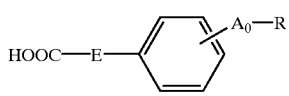

(III)

(wherein the various symbols have the same meanings as hereinbefore defined). The esterification reaction and the reaction to form an amide are known and can be carried out by known method, for example:
  (1) using an acid halide,
  (2) using a mixed acid anhydride or
  (3) using a condensing agent.
Esterification can be carried out, for example, as follows:
  (1) the method using an acid halide may be carried out, for example, by reacting a carboxylic acid with an acid halide (e. g., oxalyl chloride, thionyl chloride etc.) in an inert organic solvent (e.g., chloroform, methylene chloride, diethyl ether, tetrahydrofuran etc.) or without a solvent at from −20° C. to the reflux temperature of the solvent, and then by reacting the acid halide obtained with a corresponding alcohol in the presence of a tertiary amine (e. g., pyridine, triethylamine, diethylaniline, diethylaminopyridine etc.) in an inert organic solvent (e. g., chloroform, methylene chloride, diethyl ether, tetrahydrofuran etc.) at a temperature of from 0° C. to 40° C.;
  (2) the method using a mixed acid anhydride may be carried out, for example, by reacting a carboxylic acid and an acid halide (e. g., pivaloyl chloride, tosyl chloride, mesyl chloride etc.) or an acid derivative (e. g., ethyl chloroformate, isobutyl chloroformate etc.) in the presence of a tertiary amine (e. g., pyridine, triethyamine, dimethylaniline, dimethylaminopyridine etc.) in an inert organic solvent (e. g., chloroform, methylene chloride, diethyl ether, tetrahydrofuran etc.) or without a solvent at a temperature of from 0° C. to 40° C., and then by reacting the mixture of acid anhydride obtained with a corresponding alcohol in an inert organic solvent (e. g., chloroform, methylene chloride, diethyl ether, tetrahydrofuran etc.), at a temperature of from 0° C. to 40° C.; and
  (3) the method using a condensing agent (e. g., 1,3-dicyclohexylcarbodiimide (DCC), 1-ethyl-3-[(dimethylamino)propyl]carbodiimide (EDC), 2-chloro-1-methypyridinium iodide etc.) may be carried out, for example, by reacting a carboxylic acid with a corresponding alcohol using a condensing agent in the presence or absence of a tertiary amine (e. g., pyridine, triethylamine, dimethylaniline, dimethylaminopyridine etc.) in an inert organic solvent (e. g., chloroform, methylene chloride, dimethyl formamide, diethyl ether etc.) or without a solvent at a temperature of from 0° C. to 40° C.

The formation of an amide may be accomplished by the same reactions as described above, except the corresponding alcohol is replaced by a corresponding amine.

The reactions (1), (2) and (3) hereinbefore described may be preferably carried out in an atmosphere of inert gas (e. g., argon, nitrogen etc.) under anhydrous conditions.

The compounds of the formula (III) may be prepared by the series of reactions depicted in the following Scheme A.

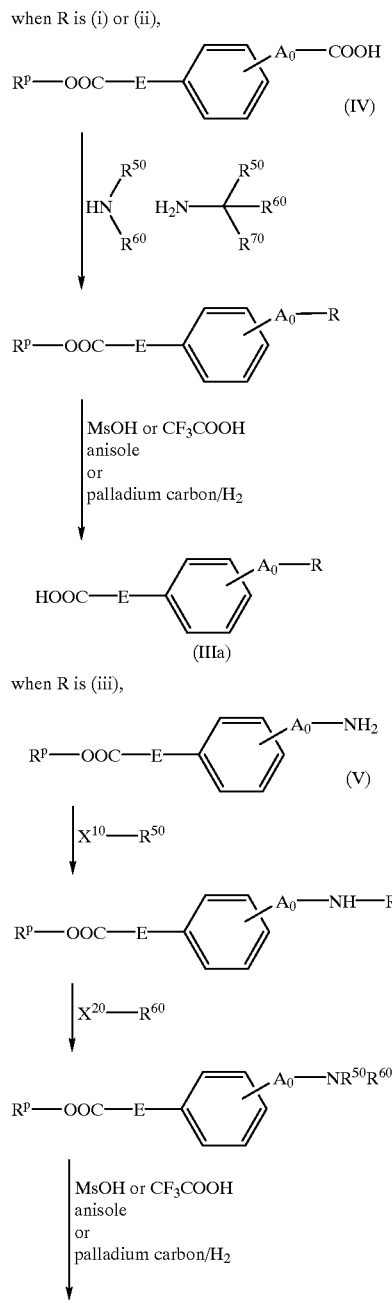

-continued

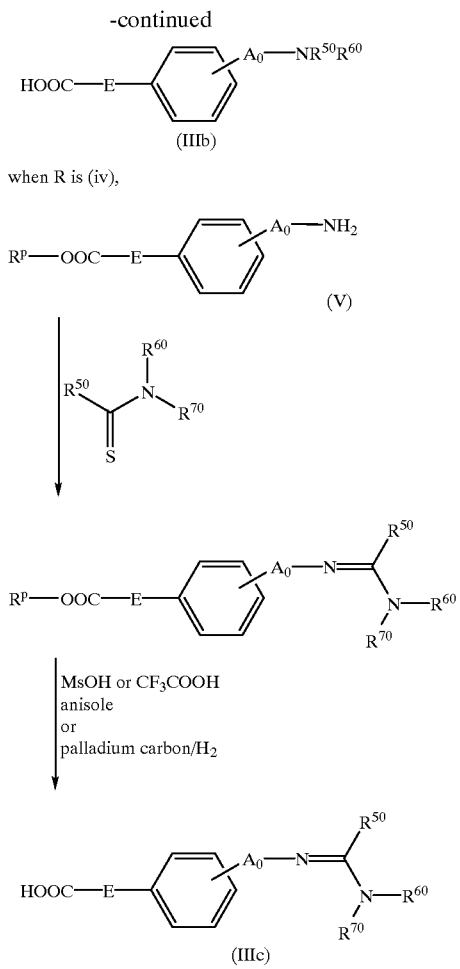

(IIIb)

when R is (iv),

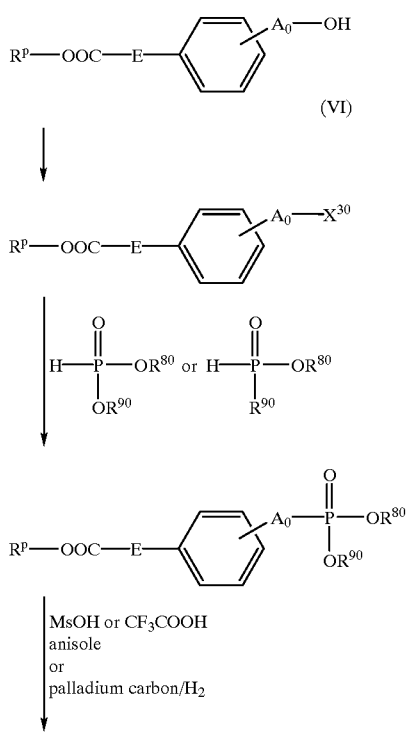

(IIIc)

when R is (v),

-continued

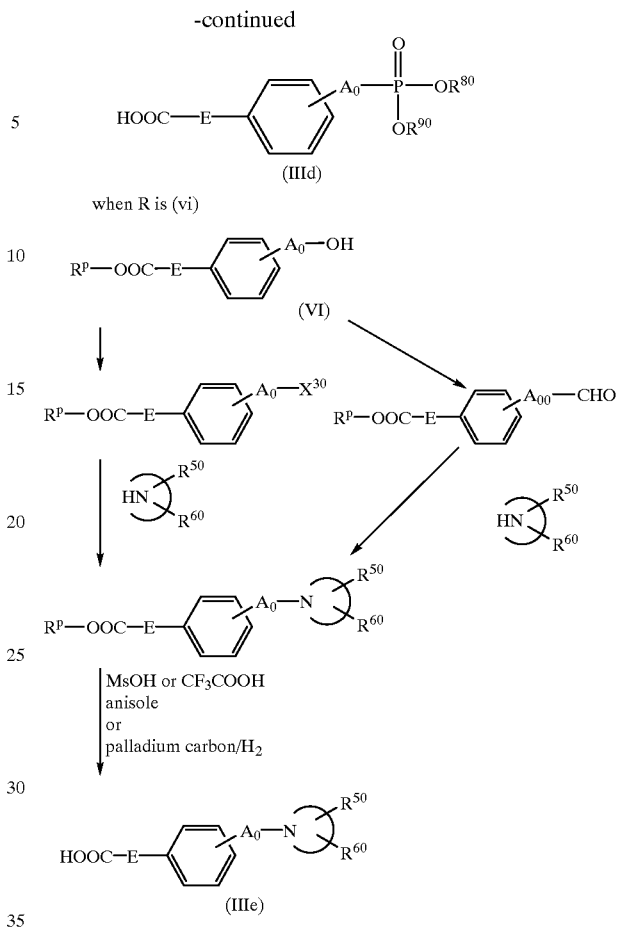

(IIId)

when R is (vi)

In the Scheme A, $R^P$ is t-butyl or benzyloxycarbonyl, $X^{10}$, $X^{20}$ and $X^{30}$ each independently, is halogen, Ms is methaneosulfonic acid, $A_{00}$ is bond, C1–3 alkylene, oxy-(C1–3) alkylene, thio-(C1–3)alkylene, C2–7 alkenylene, C2–7 alkenylene substituted by carboxy or C1–4 alkoxycarbonyl, and the other symbols have the same meaning as hereinbefore described.

The reactions in the scheme hereinbefore depicted may be carried out by methods known per se. The compounds of the formulae (II), (IV), (V) and (VI) used as starting materials in this scheme are known per se or may be easily prepared by methods known per se.

Other starting materials and each of the reagents are known per se or may be prepared by known methods.

In each reaction in the present specification, products may be purified in a conventional manner. For example, purification may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

Physiological Effects

As mentioned above, it is understood that $LTB_4$ antagonist is useful as an anti-inflammatory and anti-allergic agent.

Therefore, compounds of the present invention of formulas (IA) and (IB), having $LTB_4$ antagonistic activity, may be used for the treatment of an animal, preferably a human, as an anti-inflammatory and anti-allergic agent.

It is known that an LTB$_4$ antagonist is also useful for the prevention and/or treatment of various diseases in animals, including humans. These diseases include rheumatoid arthritis, inflammatory bowel diseases, psoriasis, nonsteroidal anti-inflammatory agent-induced stomach diseases, adult respiratory distress syndrome, cardiac infarction, allergic rhinitis, hemodialysis-induced neutropenia and anaphase asthma.

The compounds of the formula (IB) also have inhibitory activity on phospholipase and inhibitory activity on trypsin in animals, including humans. Therefore compounds of formula (IB) are useful for the prevention and/or the treatment of various inflammatory, allergic diseases, disseminated intravascular coagulation, pancreatitis, severity in pancreatitis and multiple organ failure in animals, preferably humans.

Toxicity

It is confirmed that the toxicity of the active ingredients and non-toxic salts thereof and non-toxic acid addition salts thereof in the present invention is very weak. For example, LD$_{50}$ of Compound 1 was 117 mg/kg when administered intravenously to male mice. Accordingly, the active substances in the present invention may be considered to be sufficiently safe and suitable for pharmaceutical use.

For the purpose hereinbefore described, the active ingredient in the present invention and non-toxic salts thereof and non-toxic acid addition salts thereof may be normally administered systemically or partially, usually by oral or parenteral administration.

The doses to be administered are determined depending upon age, weight, symptom, the desired therapeutic effect, the route of administration, and the duration of the treatment, etc. In the human adult, the doses per person per dose are generally between 1 mg and 1000 mg, by oral administration, up to several times per day, or between 100 μg and 100 mg, by parenteral administration (preferably, intravenously) up to several times per day. As mentioned above, the doses to be used depend upon various conditions. Therefore, there are cases in which doses lower than or greater than the ranges specified above may be used.

Compounds of the present invention are administered in the form of solid compositions, liquid compositions or other compositions for oral administration, and as injections, liniments or suppositories, etc., for parenteral administration.

Solid compositions for oral administration include compressed tablets, pills, capsules, dispersible powders, and granules.

In such compositions, at least one of the active compounds is admixed with at least one inert diluent (such as lactose, mannitol, glucose, hydroxypropyl cellulose, microcrystalline cellulose, starch, polyvinylpyrrolidone, magnesium metasilicate aluminate, etc.).

These compositions may also comprise, as in normal practice, additional substances other than inert diluents: e.g., lubricating agents (such as magnesium stearate, etc.), disintegrating agents (such as cellulose calcium glycolate, etc.), assisting agents for dissolving (such as arginine, glutamic acid, asparaginic acid, etc.) and stabilizers (human serum albumin, lactose, etc.).

The tablets or pills may, if desired, be coated with a film of gastric or enteric material (such as sugar, gelatin, hydroxypropyl cellulose, hydroxypropylmethyl cellulose phthalate, etc.).

Capsules include hard capsules and soft capsules.

Liquid compositions for oral administration include solutions, emulsions, suspensions, syrups and elixirs.

These liquid compositions may comprise inert diluents commonly used in the art (purified water, ethanol, etc.).

Besides inert diluents, such compositions may also comprise adjuvants (such as wetting agents, suspending agents, etc.), sweetening agents, flavoring agents and preserving agents.

Other compositions for oral administration include spray compositions which may be prepared by known methods and which comprise one or more of the active compound(s). Spray compositions may comprise additional substances other than inert diluents: e. g. stabilizing agents (sodium sulfate etc.), isotonic stabilizing agents (sodium chloride, sodium citrate, citric acid, etc.). For preparation of such spray compositions, for example, the method described in the U.S. Pat. No. 2,868,691 or 3,095,355 may be used.

Injections for parenteral administration include sterile aqueous or non-aqueous solutions, suspensions and emulsions.

In such compositions, one or more of active compound(s) is or are admixed with at least one of inert aqueous diluent(s) (distilled water for injection, physiological salt solution etc.) or inert non-aqueous diluent(s) (propylene glycol, polyethylene glycol, olive oil, ethanol, POLYSORBATE80 (registered trade mark ) etc.).

Injections may comprise furthermore assisting agents such as preserving agents, wetting agents, emulsifying agents, dispersing agents, stabilizing agents (such as human serum albumine, lactose, etc.) and assisting agents for dissolving (arginine, glutamic acid, asparaginic acid, polyvinylpyrrolidone etc.).

Usually, they may be sterilized by filtration (a bacteria-retaining filter, etc), by incorporation of sterilizing agents in the compositions or by irradiation, or after treated, they may also manufactured in the form of sterile solid compositions, for example, by freeze-drying, and which may be dissolved in sterile water or some other sterile diluent(s) for injection immediately before used, and which may be used.

EXAMPLES

The following Reference Examples and Examples illustrate the present invention.

The solvents in parentheses show the developing or eluting solvents used in chromatographic separations and the solvent ratios used are by volume.

Example 1(A)

Binding Inhibition Against $^3$H-LTB$_4$ on the Human Polymorphonuclear Leukocyte (PMN)

0.049 ml Hanks balanced salt solution (HBSS), 0.001 ml test compound and 0.05 ml $^3$H-LTB$_4$ (4nM) were added to polypropylene tubes and mixed. The reaction was started by addition of a thoroughly mixed PMN cell suspension (1.6× 10$^6$ cells), followed by incubation at 0° C. for 20 min. The reaction was terminated by the addition of ice-cold HBSS (2.5 ml). PMNs were harvested by vacuum filtration through Whatman GF/C glass fiber filters on a Brandel cell harvester (BRANDEL, M-24R). The filters were then washed 2 times to remove free $^3$H-LTB$_4$ with 2.5 ml of the ice-cold PBS (−) solution. The filters were transferred to each vial, and equilibrated after adding 8 ml ACS II cocktail (Amersham). The radioactivity was measured by liquid scintillation counter (Aloka, LSC-5100).

Specific binding of $^3$H-LTB$_4$ to the LTB$_4$ receptor was defined as total binding minus nonspecific binding. Nonspecific binding was the amount of $^3$H-LTB$_4$ binding in the presence of 1.5 μM $LTB_4$ instead of the test compound. The inhibitory effect of test compound was calculated from the following equation.

The percentage of inhibition (%)=100−($B_1$/$B_0$×100)

$B_1$: Specific $^3H$-$LTB_4$ binding in presence of test compound $B_0$: Specific $^3H$-$LTB_4$ binding in absence of test compound Results The results are shown in the following Table 17.

TABLE 17

| Compound No. | European Patent Publication No. 588655 Compound (Example No.) | binding activity (%) |
|---|---|---|
| 1 | 1 (i) | 91.5 |
| 2 | 1 (m) | 76.6 |
| 3 | 1 (p) | 75.0 |
| 4 | 1 (aa) | 63.7 |
| 5 | 1 (ii) | 94.3 |
| 6 | 1 (pp) | 71.6 |
| 7 | 1 (qq) | 78.0 |
| 8 | 1 (hhh) | 82.7 |
| 9 | 1 (lll) | 91.6 |
| 10 | 1 (mmm) | 86.5 |
| 11 | 2 (g) | 76.8 |
| 12 | 2 (p) | 95.2 |
| 13 | 2 (u) | 100.2 |
| 14 | 2 (w) | 96.5 |
| 15 | 2 (cc) | 89.1 |
| 16 | 2 (gg) | 83.6 |
| 17 | 2 (kk) | 93.9 |
| 18 | 3 (f) | 87.0 |
| 19 | 4 | 74.0 |
| 20 | 4 (a) | 83.5 |
| 21 | 5 (r) | 90.8 |
| 22 | 5 (w) | 89.7 |
| 23 | 5 (ff) | 78.0 |
| 24 | European Patent Publication No. 656349 Example 1 (b) | 61.2 |

The structure of compounds used in the present invention are shown below.

Compound No. 1

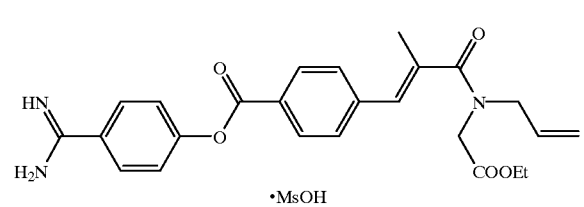

Compound No. 2

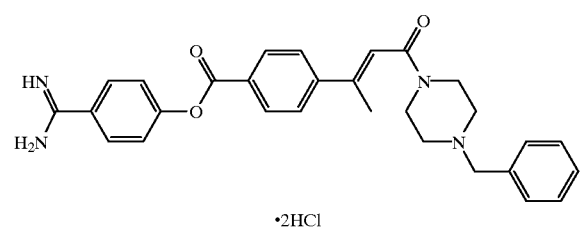

Compound No. 3

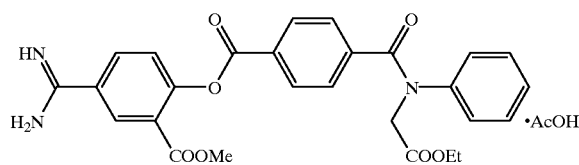

Compound No. 4

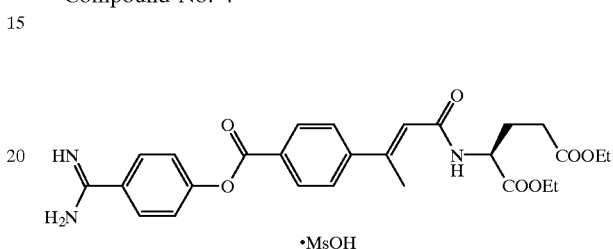

Compound No. 5

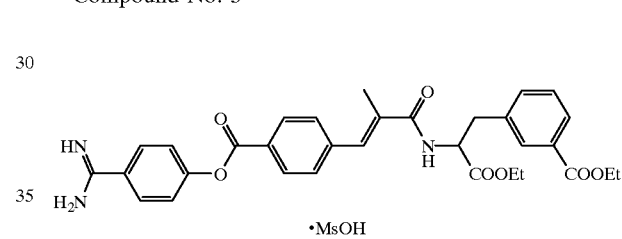

Compound No. 6

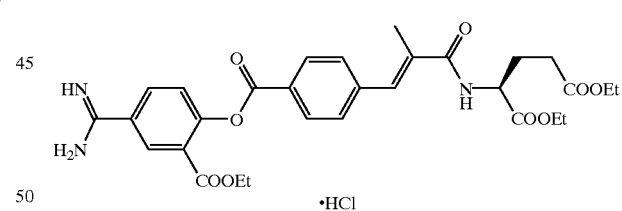

Compound No. 7

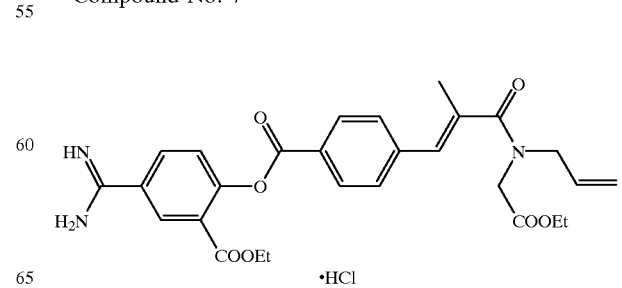

Compound No. 8
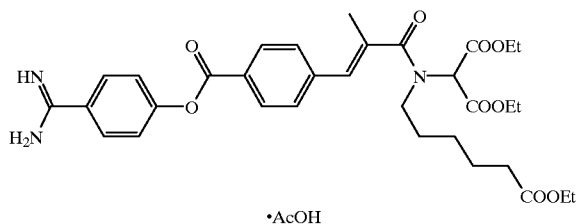
•AcOH
Compound No. 9
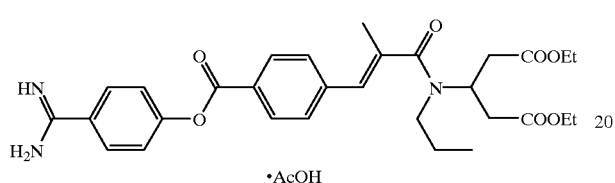
•AcOH
Compound No. 10
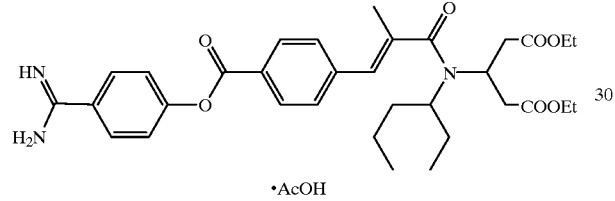
•AcOH
Compound No. 11
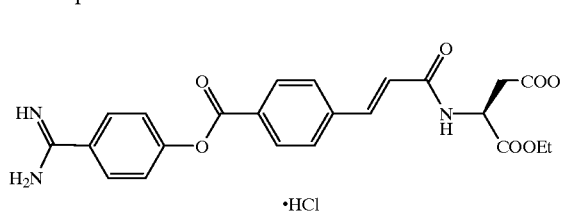
•HCl
Compound No. 12
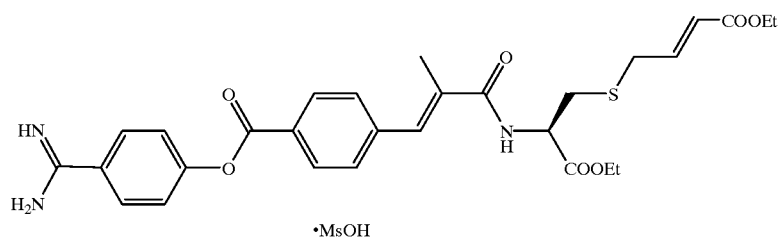
•MsOH
Compound No. 13
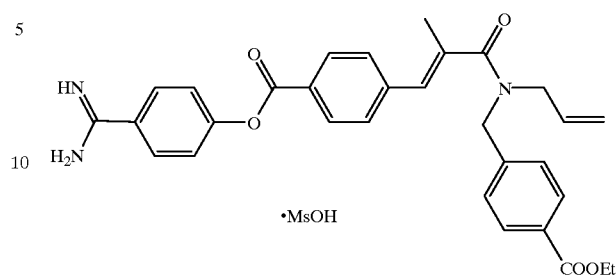
•MsOH
Compound No. 14
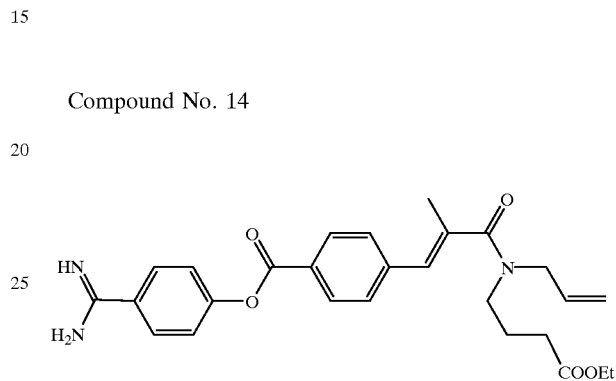
•HCl
Compound No. 15
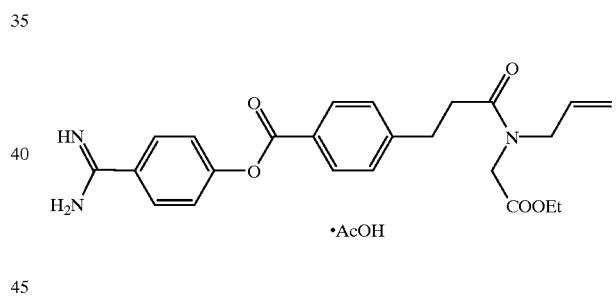
•AcOH Compound No. 16

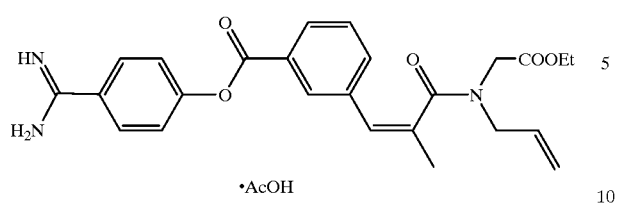

•AcOH

Compound No. 17

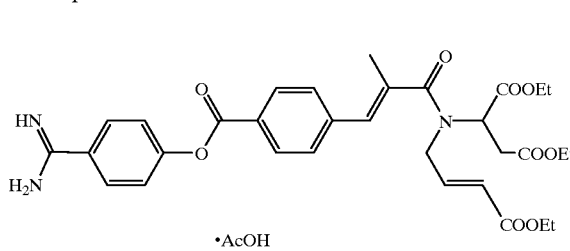

•AcOH

Compound No. 18

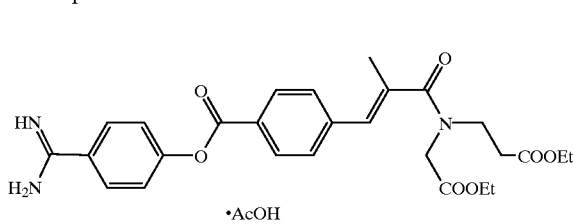

•AcOH

Compound No. 19

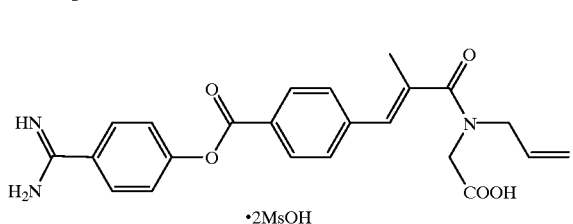

•2MsOH

Compound No. 20

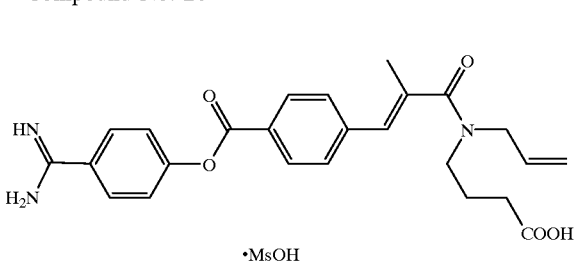

•MsOH

Compound No. 21

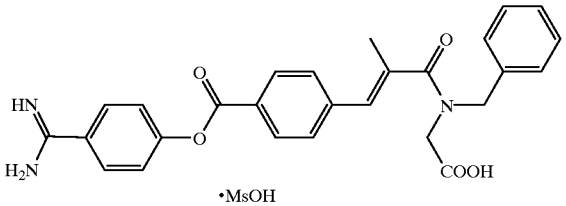

•MsOH

Compound No. 22

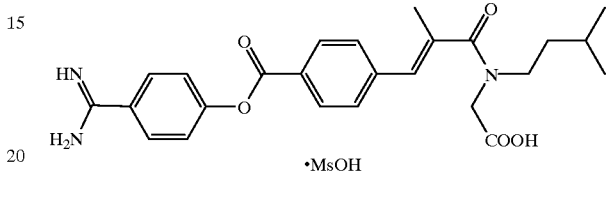

•MsOH

Compound No. 23

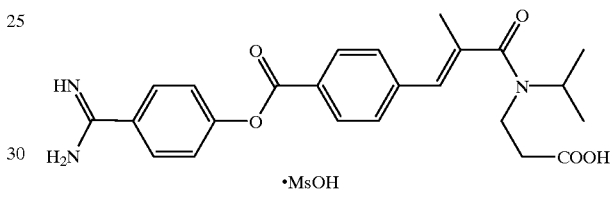

•MsOH

Compound No. 24

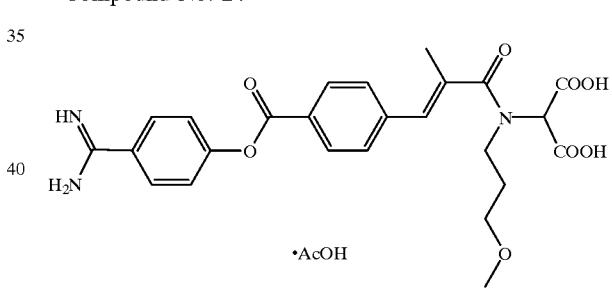

•AcOH

Example 1(B)

The compounds of the formula (IB), of the present invention have an antagonistic activity on $LTB_4$. The results which are measured by method as hereinbefore described in Example 1(A), are shown the following Table 18.

TABLE 18

| Compound (Example No.) | binding activity (%) |
|---|---|
| 2 | 79.7 |
| 2 (a) | 92.0 |
| 2 (b) | 97.9 |
| 2 (c) | 103.2 |
| 2 (d) | 99.3 |
| 2 (e) | 94.5 |
| 2 (f) | 91.8 |
| 2 (g) | 89.6 |
| 2 (h) | 85.4 |
| 2 (i) | 69.6 |

TABLE 18-continued

| Compound (Example No.) | binding activity (%) |
|---|---|
| 2 (j) | 55.4 |
| 2 (k) | 97.7 |
| 2 (l) | 81.0 |
| 2 (m) | 89.2 |
| 2 (n) | 82.8 |
| 2 (o) | 85.8 |
| 2 (p) | 95.2 |
| 2 (q) | 98.0 |
| 2 (r) | 80.1 |
| 2 (s) | 83.0 |
| 2 (t) | 51.5 |
| 2 (u) | 67.6 |
| 2 (v) | 92.0 |
| 2 (w) | 76.7 |
| 2 (x) | 94.1 |
| 2 (y) | 85.5 |
| 2 (z) | 92.8 |
| 2 (aa) | 94.4 |
| 2 (bb) | 87.3 |
| 2 (cc) | 76.7 |
| 2 (dd) | 50.8 |
| 2 (ee) | 65.3 |
| 2 (ff) | 82.4 |
| 3 | 96.8 |
| 4 | 73.1 |
| 4 (a) | 52.0 |
| 5 | 89.7 |
| 5 (a) | 62.5 |
| 5 (b) | 90.2 |
| 6 | 67.8 |

Example 1(C)

Inhibitory Activity on Phospholipase $A_2$ and on Trypsin

It has been confirmed that compounds of formula (IB) of the present invention have inhibitory activities on phospholipase$A_2$ (PLA$_2$) and on trypsin.

For example, in laboratory tests the following results were obtained.

Method (1) Inhibitory Activity on PLA$_2$

A reaction solution including 50 mM tris-HCl buffer (pH7.5, 874 μl; containing 100 mM sodium chloride, 1 mM EDTA), 1M calciumchloride (6 μl), 1% bovine serum albumin (10 μl) and 2.5 mM 10PY-PC (10 μl), was prepared. To the solution were added a test compound in various concentration or water (50 μl), and a solution of 10 mU/ml PLA$_2$ (derived from hog pancreas) (50 μl). The appearance of fluorescence was measured (Ex=345 nm, Em=396 nm). Percentage (%) of the strength of fluorescence in the presence of a test compound was calculated when the strength of that in the absence thereof was regarded as 100%, and therefrom IC$_{50}$ value was calculated. The results are shown in the following Table19.

(2) Inhibitory Activity on Trypsin

To a mixture of a 0.2 M HEPES.sodium hydroxide buffer solution (pH 8.0, 100 μl) and distilled water (640 μl), were added a test compound in various concentration or water (10 μl), and a solution of 80 mU/ml trypsin (derived from bovine pancreas) (50 μl) and then the mixture was preincubated for one minute at 30° C. To the solution thus obtained was added 2.5 mM BAPNA (200 μl) and the mixture was incubated at 30° C. The absorbance at 405 nm was measured. Percentage (%) of the absorbance in the presence of a test compound was calculated when the absorbance in the absence thereof was regarded as 100%, and therefrom IC$_{50}$ value was calculated. The results are shown in the following Table 19.

TABLE 19

| Compound (Example No.) | inhibitory activity on PLA$_2$ IC$_{50}$ (μM) | inhibitory activity on trypsin IC$_{50}$ (μM) |
|---|---|---|
| 2 | — | 0.19 |
| 2 (a) | 2.6 | 0.4 |
| 2 (b) | 3.8 | 0.56 |
| 2 (c) | 8.1 | 0.26 |
| 2 (d) | 8.7 | 0.14 |
| 2 (e) | 8.5 | 0.34 |
| 2 (f) | 70 | 0.10 |
| 2 (g) | 53 | 0.16 |
| 2 (h) | 11 | 0.15 |
| 2 (i) | 59 | 0.14 |
| 2 (j) | — | 0.12 |
| 2 (k) | 20 | 0.10 |
| 2 (l) | 94 | 0.12 |
| 2 (m) | 18 | 0.17 |
| 2 (n) | 10 | 0.16 |
| 2 (o) | 12 | 0.14 |
| 2 (p) | 29 | 0.13 |
| 2 (q) | 34 | 0.16 |
| 2 (r) | 46 | 0.16 |
| 2 (s) | 44 | 0.16 |
| 3 | 4.7 | 0.12 |
| 4 | 41 | 0.16 |
| 4 (a) | — | 0.14 |
| 5 | — | 0.13 |
| 5 (a) | — | 0.15 |
| 6 | 4.5 | 0.17 |

In the methods hereinbefore described,

10PY-PC represents 3'-palmitoyl-2-(1-pyrenedecanoyl)-L-α-phosphatidylcholine,

HEPES represents 4-2-hydroxyethyl)-1-piperazineethanesulfonic acid, and

BAPNA represents α-N-benzoyl-DL-arginine-p-nitroanilide hydrochloride.

Preparation of New Compounds

The following Reference Examples and Examples illustrate the preparation of new compounds of formula (IB).

Reference Examples 1

N-(2-Propenyl)-N-ethoxycarbonylmethyl-4-benzyloxycarbonylphenoxyacetamide

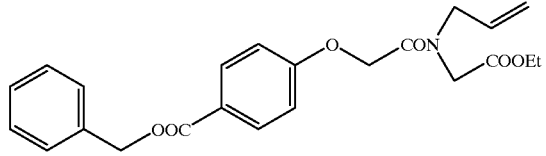

A solution of 4-benzyloxycarbonylphenoxyacetic acid (4.29 g) in thionyl chloride (10 ml) was refluxed for 15 min. After an excess amount of solvent was distilled off, product was dissolved in dichloromethane. And this solution was added dropwise to a solution of N-(2-propenyl)-N-ethoxycarbonylmethylamine (2.14 g) in pyridine under cooling with ice. After the solution was stirred for 30 min at room temperature, the solution was poured into ice water. The mixture was extracted with ethyl acetate. The extract was washed with a solution of 1N hydrochloric acid, water and a saturated aqueous solution of sodium chloride, successively, and then evaporated. The residue was then purified by silica gel column chromatograhy to obtain the title compound (5.96 g) having the following physical data:

TLC: Rf 0.43 (hexane:ethyl acetate=3:2)

Reference Example 2

N-(2-Propenyl)-N-ethoxycarbonylmethyl-4-carboxyphenoxyacetamide

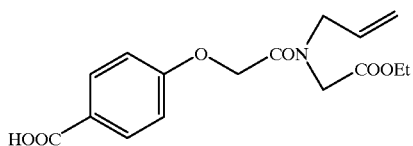

Methanesulfonic acid (28 ml) was added to the compound prepared in Reference Example 1 (5.69 g) under cooling at 0° C. After reaction, the solution was stirred for one hour at room temperature, poured into ice water and extracted with ethyl acetate. The organic layer was washed with water, and a saturated aqueous solution of sodium chloride, successively, and then evaporated. The residue was purified by silica gel column chromatography to obtain the title compound (4.31 g) having the following physical data.

TLC: Rf 0.35 (hexane:ethyl acetate=1:1)

Example 2

N-(2-propenyl)-N-ethoxycarbonylmethyl-4-(4-amidinophenoxycarbonyl)phenoxyacetamide acetate

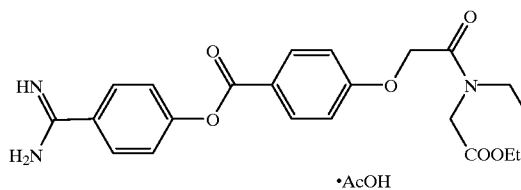

To a pyridine solution of amidinophenol (1.72 g) and the compound prepared in Reference Example 2 (3.21 g) was added DCC (3.09 g) and stirred overnight at room temperature. The reaction solution was filtered and the filtrate was evaporated. The residue was purified by silica gel column chromatography and was formed into acetate by a conventional manner to obtain the title compound having the following physical data.

TLC: Rf 0.41 (chloroform:methanol:acetic acid=10:2:1),

NMR (CD$_3$OD): δ8.14(2H, d, J=9.0 Hz), 7.90(2H, d, J=9.0 Hz), 7.49(2H, d, J=9.0 Hz), 7.08(2H, d, J=9.0 Hz), 5.68–6.07(1H, m), 5.17–5.37(2H, m), 4.93 and 5.02(2H, s, ratio=7:10), 4.03–4.28(6H, m), 1.26 and 1.29(3H, t, J=7.0 Hz).

Example 2(a)~2(ff)

By the same procedure as Reference Examples 1–2 and Example 2, the compound having the following physical data was obtained.

Example 2(a)

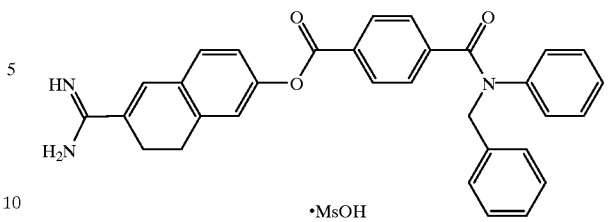

TLC: Rf 0.57 (chloroform:methanol:acetic acid=10:2:1),

NMR (CD$_3$OD): δ2.60(2H, t, J=8.0 Hz), 2.98(2H, t, J=8.0 Hz), 5.17(2H, s), 6.99–7.02(2H, m), 7.09–7.16(5H, m), 7.30(5H, s), 7.38(1H, d, J=9.0 Hz), 7.43(1H, s), 7.48(2H, d, J=8.0 Hz), 7.98(2H, d, J=8.0 Hz).

Example 2(b)

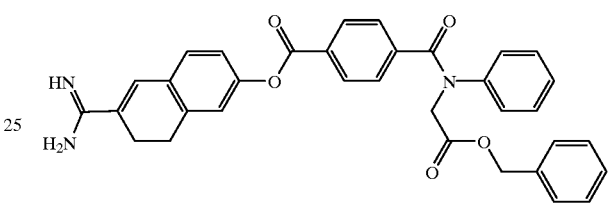

TLC: Rf 0.60 (chloroform:methanol:acetic acid=10:2:1),

NMR (CD$_3$OD): δ2.41(2H, t, J=7.0 Hz), 3.00(2H, t, J=7.0 Hz), 4.69(2H, s), 5.23(2H, s), 7.09–7.42(14H, m), 7.43(2H, d, J=8.0 Hz), 7.98(2H, d, J=8.0 Hz).

Example 2(c)

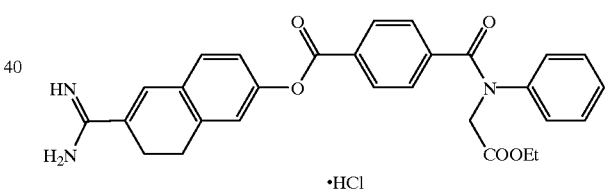

TLC: Rf 0.53 (chloroform:methanol:acetic acid=10:2:1),

NMR (CD$_3$OD): δ8.0(2H, d, J=8.0 Hz), 7.50(2H, d, J=8.0 Hz), 7.46(1H, s), 7.40(1H, d, J=8.0 Hz), 7.24(5H, s), 7.12(1H, s), 7.10(1H, d, J=8.0 Hz), 4.61(2H, s), 4.22(2H, q, J=8.0 Hz), 3.00(2H, t, J=9.0 Hz), 2.61(2H, t, J=9.0 Hz), 1.30(3H, t, J=8.0 Hz).

Example 2(d)

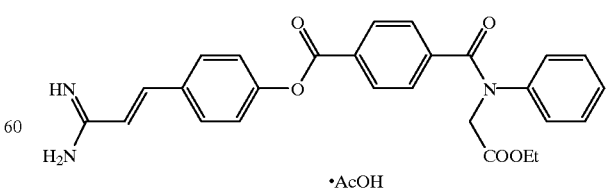

TLC: Rf 0.45 (chloroform:methanol:acetic acid=10:2:1),

NMR (CD$_3$OD): δ8.00(2H, d, J=8 Hz), 7.80(1H, d, J=16 Hz), 7.75(2H, d, J=8 Hz), 7.50(2H, d, J=8 Hz), 7.35(2H, d,

J=8 Hz), 7.30–7.20(5H, m), 6.70(1H, d, J=16 Hz), 4.65(2H, s), 4.25(2H, q, J=7 Hz), 1.30(3H, t, J=7 Hz).

Example 2(e)

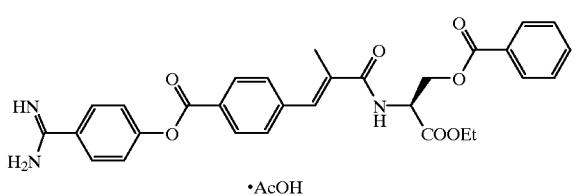

TLC: Rf 0.45 (chloroform:methanol:acetic acid=10:2:1),

NMR (CD$_3$OD): δ1.30(3H, t, J=7.0 Hz), 2.18(3H, s), 4.31(2H, q, J=7.0 Hz), 4.77(2H, m), 5.02(1H, t, J=4.0 Hz), 7.39–7.61(8H, m), 7.89(2H, d, J=9.0 Hz), 8.02(2H, d, J=9.0 Hz), 8.22(2H, d, J=9.0 Hz).

Example 2(f)

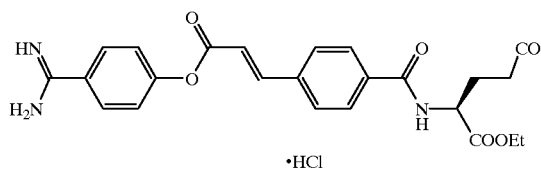

TLC: Rf 0.43 (chloroform:methanol:acetic acid=10:2:1),

NMR (CD$_3$OD): δ8.00–7.80(7H, m), 7.50(2H, d, J=8.5 Hz), 6.90(1H, d, J=16 Hz), 4.60(1H, dd, J=4.5, 4.5 Hz), 4.20(2H, q, J=6.5 Hz), 4.15(2H, q, J=6.5 Hz), 2.50(2H, t, J=7.5 Hz), 2.30(1H, m), 2.10(1H, m), 1.30(3H, t, J=6.5 Hz), 1.25(3H, t, J=6.5 Hz).

Example 2(g)

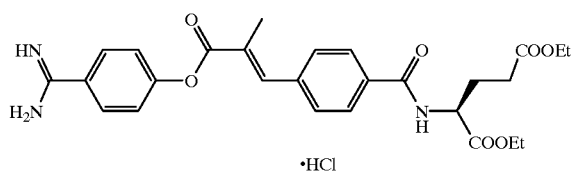

TLC: Rf 0.46 (chloroform:methanol:acetic acid=10:2:1),

NMR (CD$_3$OD): δ8.00–7.90(5H, m), 7.65(2H, d, J=8 Hz), 7.50(2H, d, J=8 Hz), 4.65(1H, dd, J=4.5, 4.5 Hz), 4.20(2H, q, J=6.5 Hz), 4.15(2H, q, J=6.5 Hz), 2.50(2H, t, J=7.5 Hz), 2.30(1H, m), 2.25(3H, m), 2.10(1H, m), 1.30(3H, t, J=6.5 Hz), 1.25(3H, t, J=6.5 Hz).

Example 2(h)

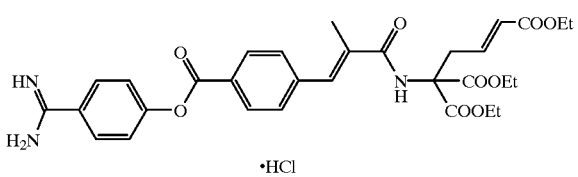

TLC: Rf 0.48 (chloroform:methanol:acetic acid=15:2:1),

NMR (CD$_3$OD): δ8.24(2H, d, J=8.5 Hz), 7.95(2H, d, J=8.5 Hz), 7.62(2H, d, J=8.0 Hz), 7.55(2H, d, J=8.0 Hz), 7.35(1H, s), 6.85(1H, dt, J=7.5, 15.0 Hz), 5.93(1H, d, J=15.0 Hz), 4.28(4H, q, J=7.5 Hz), 4.18(2H, d, J=7.5 Hz), 3.23(2H, d, J=7.5 Hz), 2.14(3H, s), 1.26(6H, t, J=7.5 Hz), 1.23(3H, t, J=7.5 Hz).

Example 2(i)

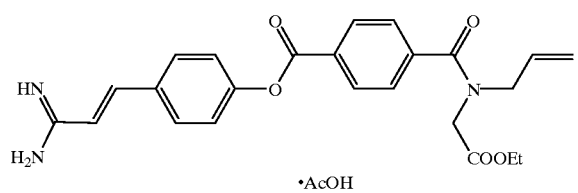

TLC: Rf 0.43 (chloroform:methanol:acetic acid=10:2:1),

NMR (CD$_3$OD): δ8.24 and 8.26(2H, d, J=9.0 Hz), 7.81 (1H, d, J=18.0 Hz), 7.75(2H, d, J=9.0 Hz), 7.58 and 7.66(2H, d, J=9.0 Hz), 7.37(2H, d, J=9.0 Hz), 6.73(1H, d, J=18.0 Hz), 5.77–5.96(1H, m), 5.22–5.34(2H, m), 4.12–4.28(4H, m), 3.96–4.00(2H, m), 1.20 and 1.30(3H, t, J=7.0 Hz).

Example 2(j)

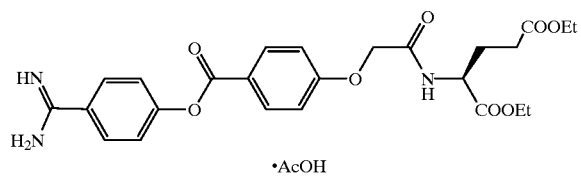

TLC: Rf 0.44 (chloroform:methanol:acetic acid=10:2:1),

NMR (CD$_3$OD): δ8.18(2H, d, J=9.0 Hz), 7.90(2H, d, J=9.0 Hz), 7.50(2H, d, J=9.0 Hz), 7.17(2H, d, J=9.0 Hz), 4.70(2H, s), 4.55(1H, dd, J=9.5, 5.0 Hz), 4.18(2H, q, J=7.0 Hz), 4.11(2H, q, J=7.0 Hz), 2.40(2H, t, J=7.0 Hz), 1.97–2.32 (2H, m), 1.27(3H, t, J=7.0 Hz), 1.23(3H, t, J=7.0 Hz).

Example 2(k)

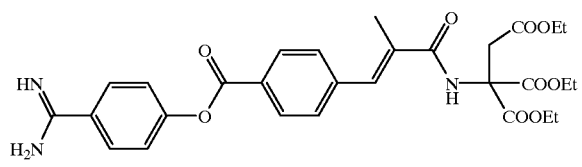

TLC: Rf 0.48 (chloroform:methanol:acetic acid=15:2:1),

NMR (CD$_3$OD): δ8.22(2H, d, J=8.0 Hz), 7.92(2H, d, J=8.0 Hz), 7.60(2H, d, J=8.0 Hz), 7.56(2H, d, J=8.0 Hz), 7.37(1H, brs), 4.27(4H, q, J=7.5 Hz), 4.13(2H, q, J=7.5 Hz), 3.47(2H, s), 2.16(3H, s), 1.25(6H, t, J=7.5 Hz), 1.22(3H, t, J=7.5 Hz).

Example 2(l)

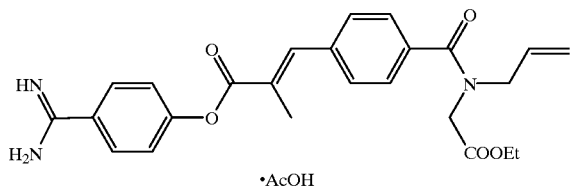

TLC: Rf 0.49 (chloroform:methanol:acetic acid=10:2:1),

NMR (CD$_3$OD): δ7.98(1H, s), 7.90(2H, d, J=9.0 Hz), 7.58(4H, m), 7.48(2H, d, J=9.0 Hz), 5.78–5.96(1H, m), 5.23–5.32(2H, m), 4.22(2H, q, J=7.0 Hz), 4.20(2H, s), 3.98–4.03(2H, m), 2.24(3H, s), 1.30(3H, t, J=7.0 Hz).

Example 2(m)

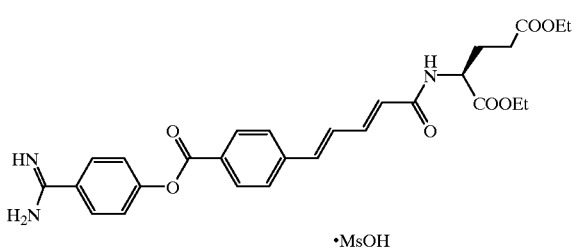

TLC: Rf 0.38 (chloroform:methanol:acetic acid=10:1:1),

NMR (CD$_3$OD): δ8.20(2H, d, J=8.4 Hz), 7.92(2H, d, J=8.8 Hz), 7.74(2H, d, J=8.4 Hz), 7.55(2H, d, J=8.8 Hz), 7.25(3H, m), 6.32(1H, d, J=14.6 Hz), 4.55(1H, m), 4.20(2H, q, J=7.2 Hz), 4.14(2H, q, J=7.0 Hz), 2.72(3H, s), 2.45(2H, t, J=7.4 Hz), 2.36–1.90(2H, m), 1.29(3H, t, J=7.2 Hz), 1.25(3H, t, J=7.0 Hz).

Example 2(n)

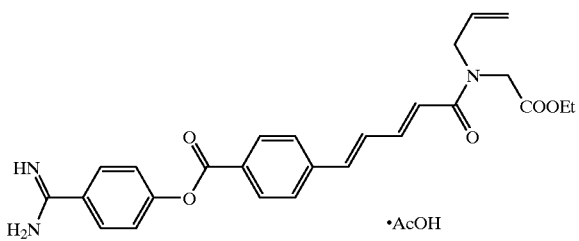

TLC: Rf 0.39 (chloroform:methanol:acetic acid=10:1:1),

NMR (CD$_3$OD): δ8.18(2H, d, J=8.4 Hz), 7.92(2H, d, J=8.8 Hz), 7.73(2H, d, J=8.4 Hz), 7.53(2H, d, J=8.8 Hz), 7.50–7.15(2H, m), 7.05(1H, d, J=14.5 Hz), 6.75–6.55(1H, m), 6.03–5.81(1H, m), 5.32–5.14(2H, m), 4.20(2H, q, J=7.2 Hz), 4.30–4.10(4H, m), 1.94(3H, s), 1.28(3H, t, J=7.2 Hz).

Example 2(o)

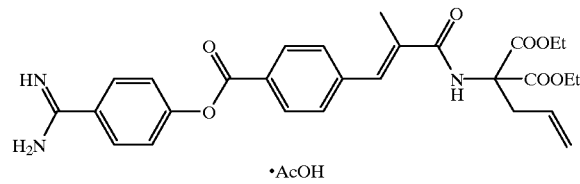

TLC: Rf 0.50 (chloroform:methanol:acetic acid=10:2:1),

NMR (CD$_3$OD): δ8.20(2H, d, J=8.5 Hz), 7.90(2H, d, J=11.5 Hz), 7.60(2H, d, J=8.5 Hz), 7.55(2H, d, J=11.5 Hz), 7.35(1H, br.s), 5.70(1H, m), 5.15(2H, m), 4.25(4H, q, J=7 Hz), 3.10(2H, d, J=7 Hz), 2.15(3H, s), 1.95(3H, s), 1.25(6H, t, J=7 Hz).

Example 2(p)

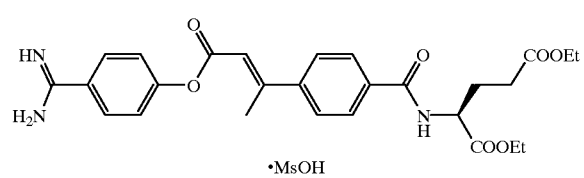

TLC: Rf 0.50 (chloroform:methanol:acetic acid=10:1:1),

NMR (CD$_3$OD): δ7.94(2H, d, J=8.0 Hz), 7.89(2H, d, J=8.5 Hz), 7.72(2H, d, J=8.5 Hz), 7.44(2H, d, J=8.0 Hz), 6.49(1H, s), 4.64(1H, m), 4.23(2H, q, J=7.5 Hz), 4.14(2H, q, J=7.0 Hz), 2.74(3H, s), 2.66(3H, s), 2.52(2H, t, J=7.0 Hz), 2.32(2H, m), 2.14(2H, m), 1.30(3H, t, J=7.0 Hz), 1.25(3H, t, J=7.5 Hz).

Example 2(q)

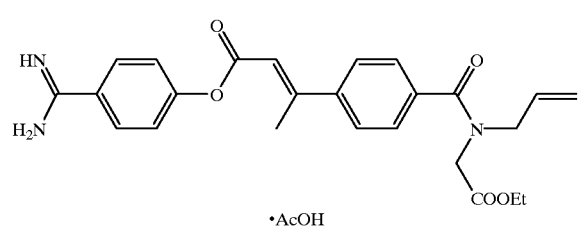

TLC: Rf 0.50 (chloroform:methanol:acetic acid=10:1:1),

NMR (CD$_3$OD): δ7.89(2H, d, J=8.8 Hz), 7.73(2H, d, J=8.4 Hz), 7.56(2H, d, J=8.4 Hz), 7.44(2H, d, J=8.8 Hz), 6.49(1H, s), 5.88(1H, m), 5.35–5.20(2H, m), 4.30–4.10(4H, m), 4.00(2H, m), 2.65(3H, s), 1.93(3H, s), 1.31(3H, t, J=7.2 Hz).

Example 2(r)

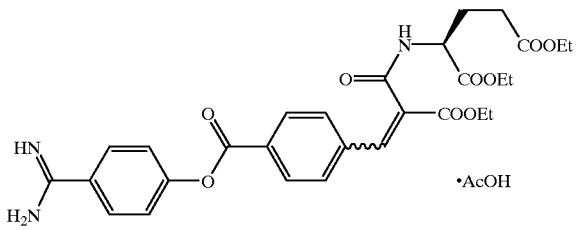

TLC: Rf 0.46 (chloroform:methanol:acetic acid=10:2:1),

NMR (CD$_3$OD): δ8.18(2H, d, J=9.0 Hz), 7.93(2H, d, J=9.0 Hz), 7.82(2H, d, J=9.0 Hz), 7.80(1H, s), 7.52(2H, d, J=9.0 Hz), 4.66(1H, dd, J=8.5 Hz, 4.0 Hz), 4.33(2H, q, J=7.0 Hz), 4.20(2H, q, J=7.0 Hz), 4.12(2H, q, J=7.0 Hz), 2.39(2H, t, J=7.0 Hz), 2.11–2.31(1H, m), 1.82–2.00(1H, m), 1.36(3H, t, J=7.0 Hz), 1.24(3H, t, J=7.0 Hz), 1.21(3H, t, J=7.0 Hz).

Example 2(s)

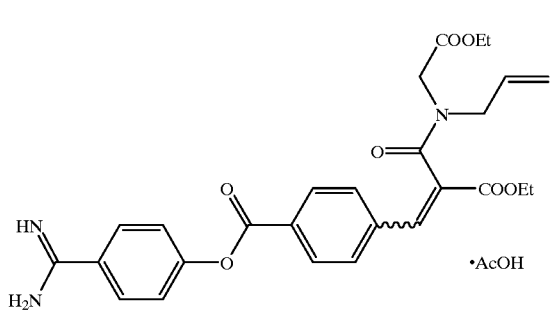

TLC: Rf 0.43 (chloroform:methanol:acetic acid=10:2:1),

NMR (CD$_3$OD): δ8.20 and 8.22(2H, d, J=8.0 Hz), 7.92 (2H, d, J=9.0 Hz), 7.75–7.90(1.6H, m), 7.64(1H, d, J=8.0 Hz), 7.54(2H, d, J=9.0 Hz), 7.18 and 7.26(0.4H, m), 5.54–5.72(0.4H, m), 5.10–5.31(2H, m), 4.17–4.40(6H, m), 3.98(2H, br), 1.08–1.38(6H, m).

Example 2(t)

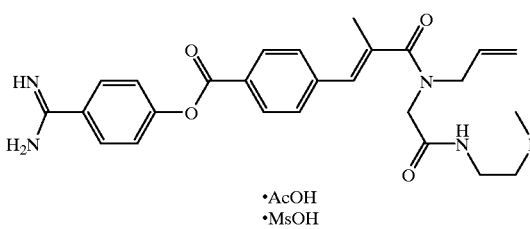

TLC:Rf 0.15 (chloroform:acetic acid: H$_2$O=3:1:1),

NMR (CD$_3$OD): δ8.23(2H, d, J=8 Hz), 7.93(2H, d, J=8 Hz), 7.58(2H, d, J=8 Hz), 7.53(2H, d, J=8 Hz), 6.80(1H, bs), 6.10–5.90(1H, b), 5.35–5.20(2H, m), 4.25–4.00(4H, m), 3.68–3.45(2H, m), 3.25–3.00(2H, m), 2.88(6H, s), 2.69(3H, s), 2.15(3H, s), 1.96(3H, s).

Example 2(u)

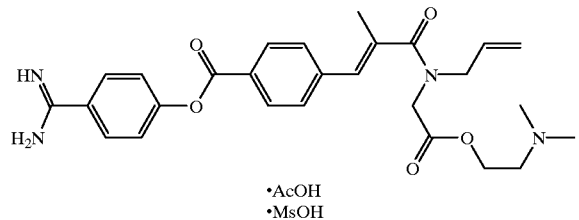

TLC: Rf 0.46 (chloroform:methanol:acetic acid=10:2:1),

NMR (CD$_3$OD): δ8.18(2H, d, J=9.0 Hz), 7.93(2H, d, J=9.0 Hz), 7.82(2H, d, J=9.0 Hz), 7.80(1H, s), 7.52(2H, d, J=9.0 Hz), 4.66(1H, dd, J=8.5 Hz, 4.0 Hz), 4.33(2H, q, J=7.0 Hz), 4.20(2H, q, J=7.0 Hz), 4.12(2H, q, J=7.0 Hz), 2.39(2H, t, J=7.0 Hz), 2.11–2.31(1H, m), 1.82–2.00(1H, m), 1.36(3H, t, J=7.0 Hz), 1.24(3H, t, J=7.0 Hz), 1.21(3H, t, J=7.0 Hz).

Example 2(v)

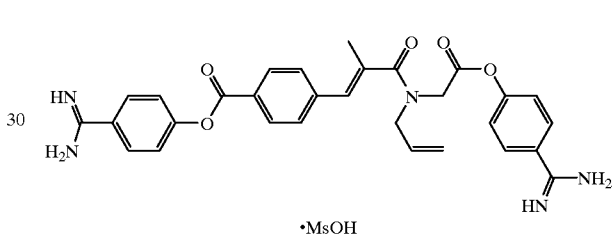

TLC: Rf 0.22 (chloroform:methanol:acetic acid=10:2:1),

NMR (CD$_3$OD): δ8.21(2H, d, J=8.0 Hz), 7.95(2H, d, J=8.0 Hz), 7.89(2H, d, J=8.0 Hz), 7.59(2H, d, J=8.0 Hz), 7.55(2H, d, J=8.0 Hz), 7.43(2H, d, J=8.0 Hz), 6.78(1H, s), 6.15–5.80(1H, m), 5.47–5.28(2H, m), 4.42(2H, s), 4.25(2H, d, J=5.0 Hz), 2.68(3H, s, CH$_3$SO$_3$H), 2.18(3H, s).

Example 2(w)

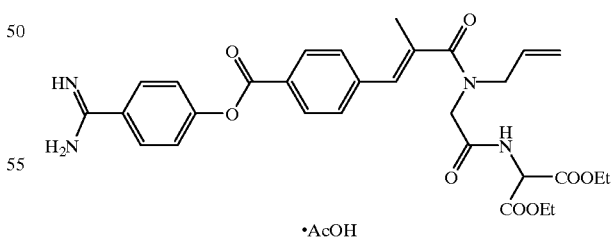

TLC: Rf 0.27 (chloroform:methanol:acetic acid=10:2:1),

NMR (CD$_3$OD): δ8.20(2H, d, J=8 Hz), 7.91 (2H, d, J=8 Hz), 7.57(2H, d, J=8 Hz), 7.53(2H, d, J=8 Hz), 6.73(1H, s), 5,8–6.0(1H, br), 5.2–5.35(2H, m), 4.8–4.9(1H, m), 4.0–4.3 (8H, m), 2.12(3H, s), 1.91(3H, s)1.27(6H, t, J=7 Hz).

Example 2(x)

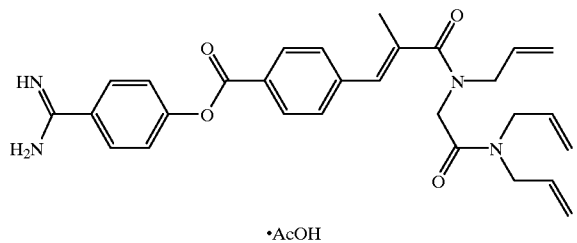

•AcOH

TLC: Rf 0.25 (chloroform:methanol:acetic acid=10:2:1),

NMR (CD$_3$OD): δ8.22(2H, d, J=8 Hz), 7.91 (2H, d, J=8 Hz), 7.52 and 7.67(4H, d, J=8 Hz, rotamer), 6.65 and 6.78(1H, s, rotamer), 5.6–6.0(3H, br), 5.0–5.3(6H, m), 3.9–4.4(8H, m), 2.11 and 2.16(3H, s, rotamer), 1.92(3H, s).

Example 2(y)

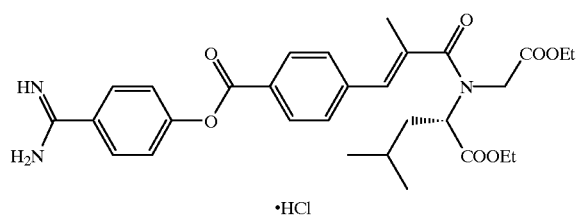

•HCl

TLC: Rf 0.41 (chloroform:methanol:acetic acid=20:2:1),

NMR (CD$_3$OD): δ8.22(2H, d, J=8.0 Hz), 7.94(2H, d, J=8.0 Hz), 7.55(4H, t, J=7.5 Hz), 6.71(1H, brs), 5.20–4.90 (1H, m), 4.40–4.00(6H, m), 2.20–2.00(3H, m), 1.95–1.50 (3H, m), 1.30(6H, t, J=7.5 Hz), 1.10–0.80(6H, m).

Example 2(z)

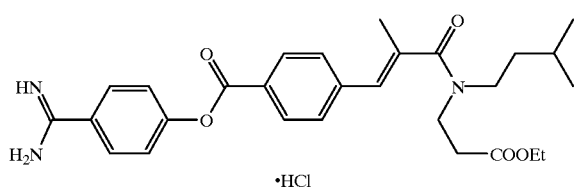

•HCl

TLC: Rf 0.40 (chloroform:methanol:acetic acid=20:2:1),

NMR (CD$_3$OD): δ8.21(2H, d, J=8.5 Hz), 7.95(2H, d, J=8.5 Hz), 7.57(4H, t, J=8.0 Hz), 6.62(1H, s), 4.15(2H, q, J=7.0 Hz), 3.80–3.60(2H, m), 3.55–3.38(2H, m), 2.68(2H, t, J=7.5 Hz), 2.12(3H, s), 1.70–1.40(3H, m), 1.27(3H, t, J=7.5 Hz), 1.10–0.70(6H, m).

Example 2(aa)

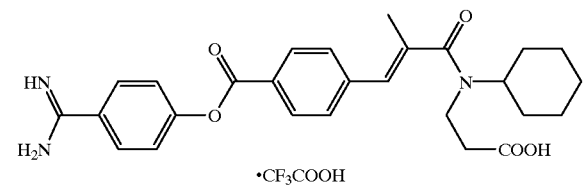

•CF$_3$COOH

TLC: Rf 0.55 (chloroform:methanol:acetic acid=10:2:1),

NMR (CD$_3$OD): δ8.23(2H, d, J=8 Hz), 7.93(2H, d, J=8 Hz), 7.57(2H, d, J=8 Hz), 7.54(2H, d, J=8 Hz), 6.60(1H, s), 3.92–3.50(3H, m), 2.70–2.55(2H, m), 2.13 and 2.11(3H, s), 1.93–1.00(10H, m).

Example 2(bb)

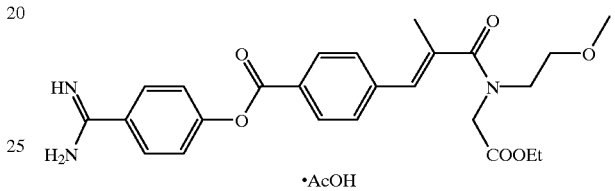

•AcOH

TLC: Rf 0.41 (chloroform:methanol:acetic acid=10:2:1),

NMR (CD$_3$OD): δ8.21 (2H, d, J=8 Hz), 7.92(2H, d, J=8 Hz), 7.65–7.50(4H, m), 6.72 and 6.65(1H, s, rotamer), 4.2–4.1(4H, m), 3.8–3.6(2H, br), 3.6–3.5(2H, br), 3.34(3H, s), 2.17(3H, s), 1.91(AcOH), 1.35–1.15(3H, br).

Example 2(cc)

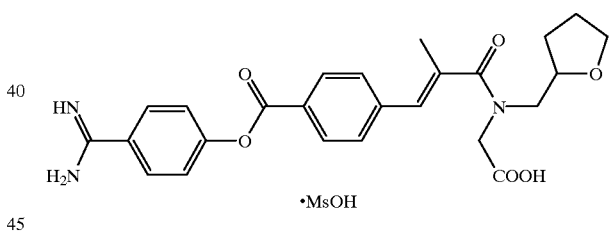

•MsOH

TLC: Rf 0.30 (chloroform:methanol:acetic acid=10:2:1),

NMR (CD$_3$OD): δ8.21 (2H, d, J=8 Hz), 7.92(2H, d, J=8 Hz), 7.60–7.45(4H, m), 6.73 and 6.65(1H, s, rotamer), 4.5–4.3(1H, m), 4.3–4.0(2H, br), 4.0–3.7(3H, m), 3.7–3.5 (1H, br), 2.70(3H, s), 2.17 and 2.10(3H, s, rotamer), 2.2–1.8 (3H, m), 1.8–1.4(1H, m).

Example 2(dd)

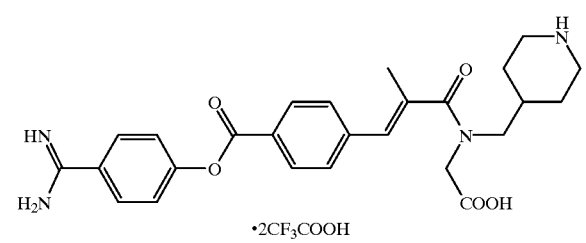

•2CF$_3$COOH

TLC: Rf 0.10 (ethyl acetate:acetic acid: H₂O=3:1:1),

NMR (CD₃OD): δ8.22(2H, d, J=8 Hz), 7.92(2H, d, J=8 Hz), 7.7–7.4(4H, m), 6.70(1H, s), 4.5–4.0(3H, br), 3.6–3.4 (2H, m), 3.2–3.0(2H, m), 2.3–1.9(7H, br).

Example 2(ee)

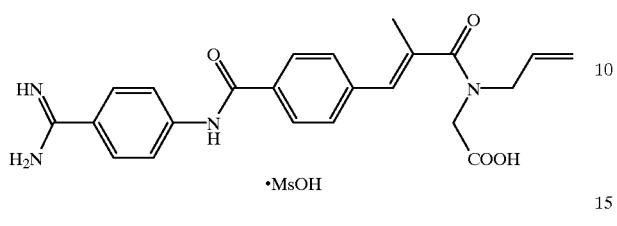

•MsOH

TLC: Rf 0.43 (chloroform:methanol:acetic acid=3:1:1),

NMR (CD₃OD): δ9.20(1H, br. s), 8.70(1H, br. s), 8.05–7.95(4H, m), 7.85(2H, d, J=9 Hz), 7.75(2H, J=8 Hz), 6.75(1H,m), 5.95(1H, m), 5,30(2H, m), 4.20(4H, m), 2.75 (3H, s, CH₃SO₃H), 2.20(3H, s).

Example 2(ff)

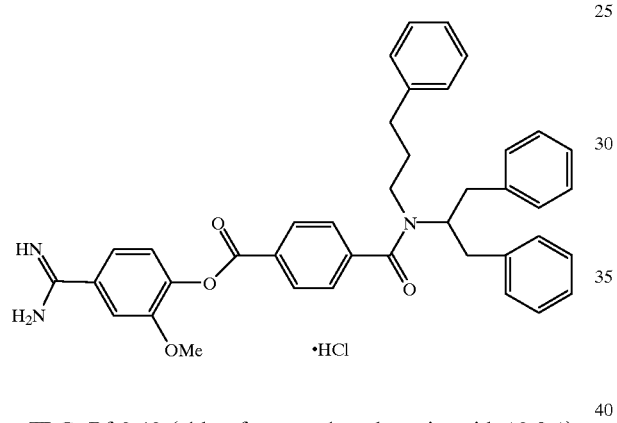

•HCl

TLC: Rf 0.40 (chloroform:methanol:acetic acid=10:2:1),

NMR (CDCl₃): δ8.02(1H, d, J=9 Hz), 7.90(1H, d, J=9 Hz), 7.64(1H, s), 7.50(1H, d, J=9 Hz), 7.40–7.00(14H, m), 6.95–6.80(2H, m), 6.80–6.72(1H, m), 6.48(1H, d, J=9 Hz), 4.00–3.80(1H, m), 3.88(3H, s), 3.70–3.30,(2H, m), 3.10–2.90(1H, m), 2.90–2.70(2H, m), 2.70–2.30(2H, m), 2.30–2.00(2H, m), 1.00–1.24(1H, m).

Reference Example 3

2-(N-Benzyl-N-methylamino)-2-(4-t-butoxycarbonylphenylmethylimino)acetic acid ethyl ester

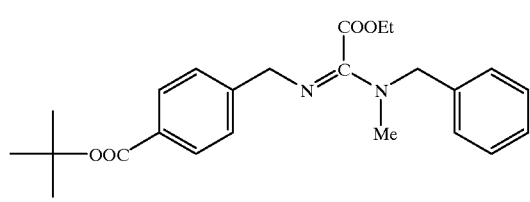

To a solution of 2-(N-benzyl-N-methylamino)-2-thioxoacetic acid ethyl ester (4.98 g) in dichloromethane under cooling with ice, was added dropwise BF₄.Et₃O (72 ml). The reaction solution was stirred for 30 min at room temperature and extracted with dichloromethane. The extract was evaporated. The resulting residue was purified by silica gel column chromatography to obtain the title compound having the following the physical data.

TLC: Rf 0.45 (hexane:ethyl acetate=3:1).

Reference Example 4

2-(N-Benzyl-N-methylamino)-2-(4-carboxyphenylmethylimino)acetic acid ethyl ester

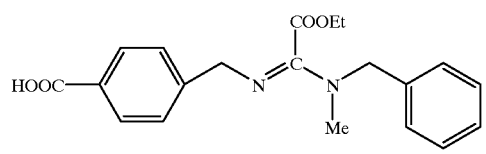

To a solution of the compound prepared in Reference Example 3 (3.77 g) in anisole (10 ml) under cooling with ice bath, was added trifluoroacetic acid (20 ml) and stirred for two hours at room temperature. The reaction solution was evaporated, neutralizied by adding 1N aqueous solution of sodium hydroxide, and extracted with ethyl acetate. The extract was evaporated. The resulting residue was purified by silica gel column chromatography to obtain the title compound (1.87 g) having the following physical data.

TLC: Rf 0.36 (hexane:ethyl acetate=1:2).

Example 3

2-[4-(4-Amidinophenoxycarbonyl) phenylmethylimino]-2-(N-benzyl-N-methylamino) acetic acid ethyl ester hydrochroride

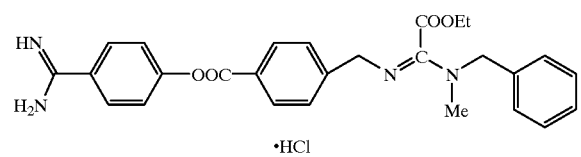

•HCl

By the same procedure as Example 2, the title compound having the following physical data was obtained.

TLC: Rf 0.34 (chloroform:methanol:acetic acid=10:2:1),

NMR (CD₃OD): δ1.26(3H, t, J=7.0 Hz), 2.88(3H, s), 4.36(2H, q, J=7.0 Hz), 4.49(2H, s), 4.50(2H, s), 7.27–7.35 (5H, m), 7.48(2H, d, J=9.0 Hz), 7.52(2H, d, J=9.0 Hz), 7.92(2H, d, J=9.0 Hz), 8.12(2H, d, J=9.0 Hz).

Reference Example 5

Ethyl 1-(3-phenylpropyl)-1-(4-benzyloxycarbonylphenylmethyl)phosphinate

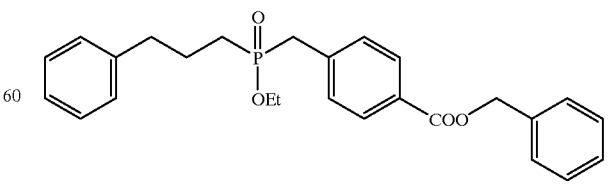

A solution of ethyl phenylpropylphosphinate (1.2 g) and triethylamine (2.4 ml) in chloroform (30 ml) was cooled to 0° C., and a solution of trimethylsilylchloride (1.46 ml) and 4-bromomethylbenzoic acid benzyl ester (1.75 g) in chloroform (10 ml) was added thereof, and stirred at room temperature for 1.5 day. To the reaction mixture was added ice water and extracted with ethyl acetate. Organic layer was washed with water and a saturated aqueous solution of sodium chloride, successively evaporated. The residue was purified by silica gel column chromatography to give the title compound (900 mg).

Reference Example 6

Ethyl 1-(3-phenylpropyl)-1-(4-carboxyphenylmethyl)phosphinate

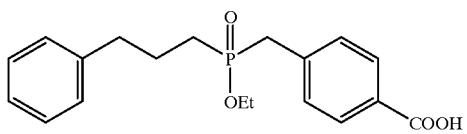

A mixture of the compound prepared in Reference Example 5 (900 mg), palladium carbon (180 mg, 10%) and ethanol (20 ml) was stirred for two hours under an atmosphere of hydrogen at room temperature. The reaction mixture was filtered. The filtrate was evaporated and the title compound (815 mg) was obtained.

Example 4

Ethyl 1-(4-amidinophenoxycarbonylphenylmethyl)-1-(3-phenylpropyl)phosphinate acetate

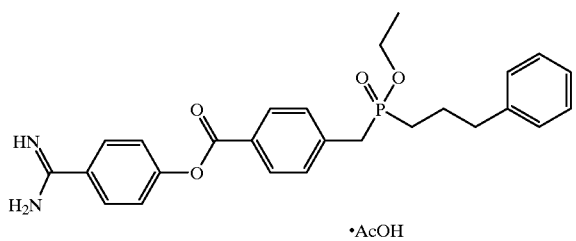

By the same procedure as Reference Example 5,6 and Example 2, the title compound (805 mg) having the following physical data was obtained.

TLC: Rf 0.62 (chloroform:methanol:acetic acid=10:2:1),
NMR (CD$_3$OD): δ8.10(2H, d, J=8 Hz), 7.95(2H, d, J=9 Hz), 7.55(2H, d, J=9 Hz), 7.60–7.40(2H, m), 7.30–7.10(3H, m), 7.20(2H, d, J=8 Hz), 4.00(2H, m), 3.40(2H, d, J=24 Hz), 2.70(2H, t, J=6.5 Hz), 2.00–1.60(4H, m), 1.30(3H, t,J=7.5 Hz).

Example 4(a)

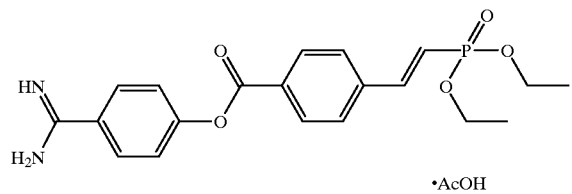

By the same procedure as Example 4, the compound having the following physical data was obtained.

TLC: Rf 0.60 (chloroform:methanol:acetic acid=10:2:1),

NMR (CD$_3$OD): δ1.36(6H, t, J=7.0 Hz), 4.15(4H, quin, J=7.0 Hz), 6.68(1H, t, J=18.0 Hz), 7.54(2H, d, J=9.0 Hz), 7.56(1H, dd, J=23.0 Hz,18.0 Hz), 7.82(2H, d, J=9.0 Hz), 7.93(2H, d, J=9.0 Hz), 8.22(2H, d, J=9.0 Hz).

Reference Example 7

4-Phenylpiperidine-1-ylmethylbenzoic Acid Methyl Ester

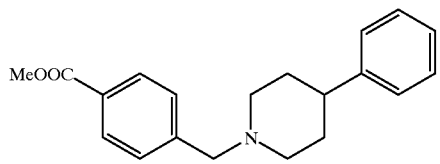

A solution of 4-formylbenzoic acid (3.5 g) and 4-phenylpiperidine (6.9 g) in methanol (35 ml) was stirred for one hour at room temperature. After the solution was cooled with ice bath, sodium borohydride (1.63 g) was added and the reaction solution was stirred. After the reaction finished, the reaction solution was poured into ice water and extracted with ethyl acetate. The organic layer was washed with water and a saturated aqueous solution of sodium chloride, successively, dried over and evaporated. The residue was washed with methanol to obtain the title compound (4.70 g).

Reference Example 8

4-(4-Phenylpiperidine-1-ylmethyl)benzoic Acid

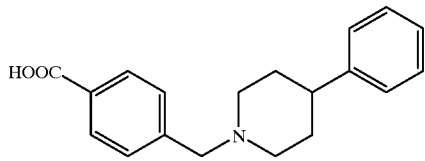

A solution of the compound prepared in Reference Example 7 (4.8 g) in dioxane (50 ml) was cooled with ice bath and 2N aqueous solution of sodium hydroxide (10 ml) was added thereof and stirred at 60° C. for two hours. The reaction mixture was cooled with ice bath and neutralized by adding 2N hydrochloric acid. Depositing solid was fittered and washed with water, ether successively, dried over. The title compound (4.29 g) was obtained.

Example 5

4-(4-Phenylpiperidine-1-ylmethyl)benzoic acid amidinophenol ester 2 hydrochloride

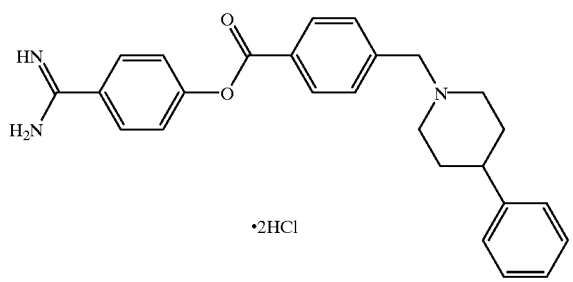

By the same procedure as Example 2, the title compound having the following physical data was obtained.

TLC: Rf 0.33 (chloroform:methanol:acetic acid=5:1:1),

NMR (CD$_3$OD): δ8.32(2H, d, J=8.0 Hz), 7.95(2H, d, J=8.8 Hz), 7.88(2H, d, J=8.0 Hz), 7.55(2H, d, J=8.8 Hz), 7.28(5H, m), 4.52(2H, s), 3.62(2H, br.d), 3.25(2H, br.d), 2.94(1H, m), 2.12(4H, m).

Example 5(a)–5(b)

By the same procedure as Reference Example 7,8 and Example 5, the compounds having the following physical data were obtained.

Example 5(a)

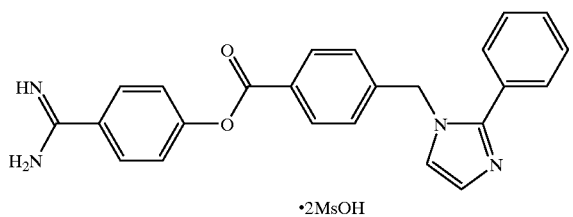

TLC: Rf 0.3 (chloroform:methanol:acetic acid=50:10:1),

NMR (CD$_3$OD): δ8.20(2H, d, J=8.0 Hz), 7.95(2H, d, J=8.0 Hz), 7.81(1H, d, J=2.0 Hz), 7.79(1H, d, J=2.0 Hz), 7.69(5H, brs), 7.55(2H, d, J=8.5 Hz), 7.39(2H, d, J=8.5 Hz), 5.63(2H, s), 2.72(6H, s).

Example 5(b)

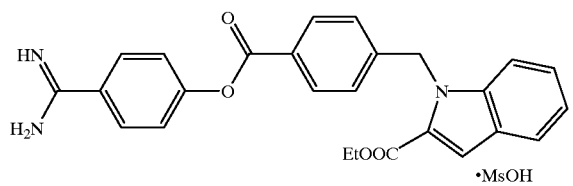

TLC: Rf 0.48 (chloroform:methanol:acetic acid=10:1:1),

NMR (CD$_3$OD+CDCl$_3$): δ8.05(2H, d, J=8.4 Hz), 7.89 (2H, d, J=8.8 Hz), 7.71(1H, d, J=8.0 Hz), 7.46(2H, d, J=8.8 Hz), 7.40(1H, s), 7.37–7.30(2H, m), 7.17(1H, d, J=8.0 Hz), 7.16(2H, d, J=8.4 Hz), 5.95(2H, s), 4.30(2H, q, J=7.4 Hz), 2.73(3H, s), 1.33(3H, t, J=7.4 Hz).

Reference Example 9

4-(N-Benzyl-N-ethoxycarbonylaminomethyl) benzoic Acid Benzyl Ester

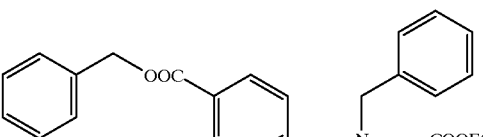

A solution of 4-(N-benzylaminomethyl)benzoic acid benzyl ester (5.21 g) and bromoacetic acid benzyl ester (1.7 ml) in DMF (10 ml) was stirred for two hours at 80° C. and ice water was added thereto. The reaction solution was extracted with ethyl acetate. The organic layer was washed with a saturated aqueous solution of sodium hydrogen carbonate, water and a saturated aqueous solution of sodium chloride, successively. The organic layer was dried over and evaporated. The residue was purified by silica gel column chromatography to obtain the title compound (2.26 g).

Reference Example 10

4-(N-Benzyl-N-ethoxycarbonylaminomethyl) benzoic Acid Hydrochloride

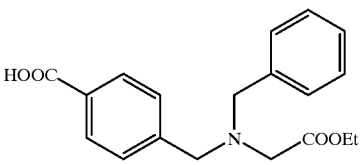

A mixture solution of the compound prepared in Reference Example 9 (2.26 g), methanesufonic acid (10.5 ml), and anisole (25 ml) was stirred for one hour at room temperature. To the reaction solution was added ice water and extracted with chloroform. The organic layer was washed with water, a saturated aqueous solution of sodium chloride, dried over and evaporated. The residue was purified by silica gel column chromatography to obtain amine. 4N hydrochloric acid-dioxane was added to the amine and the mixture was evaporated to obtain the title compound (1.76 g).

Example 6

N-(4-((4-Amidino-phenoxycarbonyl)phenylmethyl)-N-benzylaminoacetic acid Ethyl Ester 2 Hydrochroride

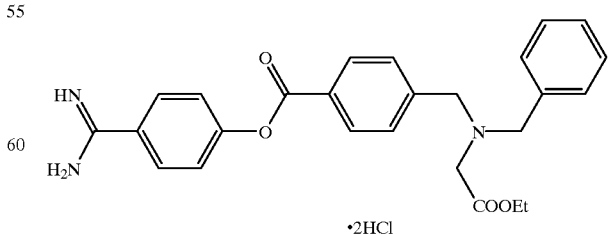

By the same prodedure as Example 2, the title compound having the following physical data was obtained.

TLC: Rf 0.42 (chloroform:methanol:acetic acid=10:2:1),

NMR (CD$_3$OD): δ8.25(2H, d, J=8 Hz), 7.90(2H, d, J=8 Hz), 7.60(2H, d, J=8 Hz), 7.50(2H, d, J=8 Hz), 7.40–7.20 (5H, m), 4.15(2H, q, J=7 Hz), 3.90(2H, s), 3.80(2H, s), 3.30(2H, s), 1.25(3H, t, J=7 Hz).

Formulation Example 1

The following components were admixed in a conventional manner and punched out to obtain 100 tables, each containing 100 mg of active ingredient.

| Compound number 1 | 10 g |
|---|---|
| Cellulose calcium glycolate (disintegrating agent) | 0.2 g |
| Magnesium stearate (Lubricating agent) | 0.1 g |
| Microcrystaline cellulose | 1.7 g |

Formulation Example 2

The following components were admixed conventional method and punched out to obtain 100 tables each containing 100 mg of active ingredient.

| Compound number 2 | 10 g |
|---|---|
| Cellulose calcium glycolate (disintegrating agent) | 0.2 g |
| Magnesium stearate (Lubricating agent) | 0.1 g |
| Microcrystaline cellulose | 1.7 g |

Formulation Example 3

The following components were admixed in conventional manner. The solution was sterilized conventional manner, placed 5 ml portions into 10 ml ampoules and obtained 100 ampoules each containing 10 mg of the active ingredient.

| Compound number 1 | 1 g |
|---|---|
| Citric acid | 0.2 g |
| distilled water | 500 ml |

Formulation Example 4

The following components were admixed in conventional manner. The solution was sterilized in conventional manner, placed 5 ml portions into 10 ml ampules to obtain 100 ampoules, each containing 10 mg of the active ingredient.

| Compound number 2 | 1 g |
|---|---|
| Citric acid | 0.2 g |
| distilled water | 500 ml |

What we claim is:

1. A new amidinophenol derivative of formula (1B):

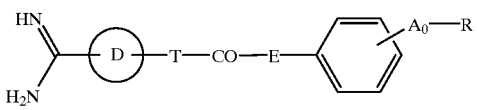
(1B)

wherein:

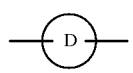

is a group of the formula:

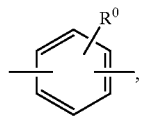
(i)

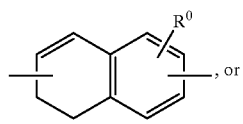
(ii)

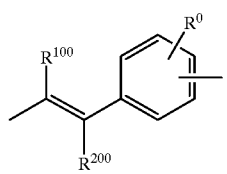
(iii)

wherein $R^0$ is hydrogen, or C1–4 alkyl, or C1–4 alkoxy, and $R^{100}$ and $R^{200}$ each independently is hydrogen or C1–4 alkyl;

T is oxygen;

E is a group of the formula:

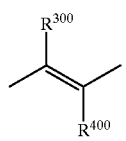

wherein $R^{300}$ and $R^{400}$ each independently, is hydrogen or C1–4 alkyl, $A_0$ is a single bond, C1–4 alkylene, -oxy-(C1–4) alkylene-, -thio-(C1–4)alkylene-, C2–8 alkenylene, or C2–8 alkenylene substituted by or carboxy or by C1–4 alkoxycarbonyl;

R is a group of the formula:

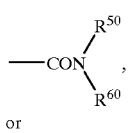
(i)

or (ii)

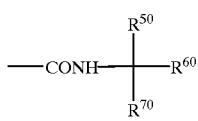

$R^{50}$, $R^{60}$ and $R^{70}$ each independently, is,
(i) hydrogen,
(ii) C1–8 alkyl,
(iii) C2–8 alkenyl
(iv) —COOR$^{110}$ (in which R$^{110}$ is hydrogen or C1–4 alkyl optionally substituted by phenyl),
(v) —(C1–8 alkylene)-COOR$^{110}$ (in which R$^{110}$ has the same meaning as hereinbefore defined),
(vi)—(C2–8 alkenylene)-COOR$^{110}$ (in which R$^{110}$ is the same meaning as hereinbefore defined),
(vii) C4–7 cycloalkyl,
(viii)—(C1–4 alkylene)-(4–7 membered hetero ring containing one oxygen),
(ix) —(C1–4 alkylene)-(4–7 membered hetero ring containing one nitrogen),
(x) phenyl,
(xi) C1–8 alkyl substituted by one or two phenyl,
(xii) —(C1–4 alkylene)-O-benzoyl,
(xiii) —(C1–4 alkylene)-CONH—(C1–4 alkylene)-NR$^{120}$R$^{130}$,
(xiv) —(C1–4 alkylene)-COO—(C1–4 alkylene)-NR$^{120}$R$^{130}$,
(xv) —(C1–4 alkylene)-COO-amidinophenyl,
(xvi) —(C1–4 alkylene)-CONH—(C1–4 alkyl substituted by one or two COOR$^{110}$) (in which R$^{110}$ has the same meaning as hereinbefore defined),
(xvii) —(C1–4 alkylene)-CONR$^{120}$R$^{130}$, or
(xviii) (C1–4) alkoxy (C1–4) alkyl,
R$^{120}$ and R$^{130}$ each independently, is hydrogen, C1–4 alkyl, or C2–8 alkenyl, with the provisos that:
(1) R$^{50}$ and R$^{60}$ in the formulae (i) R$^{50}$, R$^{60}$ and R$^{70}$ in the formulae (ii) and are not hydrogen at the same time,
(2) when at least one substituent in R$^{50}$, R$^{60}$, R$^{70}$ and A$_0$ is a substituent containing —COO-t-Bu, the other groups are not groups containing carboxy,
(3) R$^{120}$ and R$^{130}$ are not hydrogen at the same time.

2. A compound according to claim 1, wherein R$^{50}$, R$^{60}$ and R$^{70}$ each independently, is
(i) hydrogen,
(ii) C1–8 alkyl,
(iii) C2–8 alkenyl
(iv) —COOR$^{110}$,
(v) —(C1–8 alkylene)-COOR$^{110}$,
(vi) —(C2–8 alkenylene)-COOR$^{110}$,
(vii) C4–7 cycloalkyl,
(x) phenyl,
(xi) C1–8 alkyl substituted by one or two phenyl,
(xii) —(C1–4 alkylene)-O-benzoyl,
(xiii) —(C1–4 alkylene)-CONH—(C1–4 alkylene)-NR$^{120}$R$^{130}$,
(xiv) —(C1–4 alkylene)-COO—(C1–4 alkylene)-NR$^{120}$R$^{130}$,
(xv) —(C1–4 alkylene)-OCO-amidinophenyl,
(xvi) —(C1–4 alkylene)-CONH—(C1–4 alkyl substituted by one or two COOR$^{110}$),
(xvii) —(C1–4 alkylene)-CONR$^{120}$R$^{130}$, or
(xviii) (C1–4) alkoxy (C1–4) alkyl
in which the various symbols are defined in claim 1.

3. A compound according to claim 1, wherein R$^{50}$, R$^{60}$ and R$^{70}$ each independently, is
(viii) —(C1–4 alkylene)-(4–7 membered hetero ring containing one oxygen).

4. A compound according to claim 1, wherein R$^{50}$, R$^{60}$ and R$^{70}$ each independently, is
(ix) —(C1–4 alkylene)-(4–7 membered hetero ring containing one nitrogen).

5. A compound according to claim 1, which is bis(ethoxycarbonyl)prpopylamide,
4-[2-(4-amindinophenoxycarbonyl)-1-propenyl]benzoic acid N-1-(S), 3-bis(ethoxycarbonyl)propylamide,
4-(4-amindinophenoxycarbonyl)-α-methylcinnamic acid N-[1,1,4- ethoxycarbonylmethyl-N-allylamide,
5-[4-(4-amidinophenoxycarbonyl)phenyl]-2, 4-pentadienoic acid N-1-(S),
3-5-[4-(4-amidinophenoxycarbonyl)phenyl]-2, 4-pentadienoic acid N-ethoxycarbonylmethyl-N-allylamide,
4-(4-amidinophenoxycarbonyl)-α-methylcinnamic acid N-[1,1-bis(ethoxycarbonyl)-3-butenyl]amide,
4-[2-(4-amidinophenoxycarbonyl)-1-methylethenyl] benzoic acid N-1-(S), 3-
4-[2-(4-amidinophenoxycarbonyl)-1-methylethenyl] benzoic acid N-ethoxycarbonylmethyl-N-allylamide, or
3-[4-(4-amidinophenoxycarbonyl)phenyl]-2-ethoxycarbonyl-2-propenoic acid N-1-(S), 3-bis (ethoxycarbonyl)propylamide,
3-[4-(4-amidinophenoxycarbonyl)phenyl]-2-ethoxycarbonyl-2-propenoic acid N-ethoxycarbonylmethyl-N-allylamide,
4-(4-amidinophenoxycarbonyl)-α-methylcinnamic acid N-2-dimethylaminoethylcarbamoylmethyl-N-allylamide,
4-(4-amidinophenoxycarbonyl)-α-methylcinnamic acid N-2-dimethylaminoethoxycarbonylmethyl-N-allylamide,
4-(4-amidinophenoxycarbonyl)-α-methylcinnamic acid N-4-amidinophenoxycarbonylmethyl-N-allylamide,
4-(4-amidinophenoxycarbonyl)-α-methylcinnamic acid N-1,1-bis(ethoxycarbonyl)methylcarbamoylmethyl-N-allylamide,
4-(4-amidinophenoxycarbonyl)-α-methylcinnamic acid N-(diallylcarbamoyl)methyl-N-allylamide,
4-(4-amidinophenylcarbamoyl)-α-methylcinnamic acid N-allyl-N-carboxymethylamide, or
4-(4-amidino-1-methoxyphenoxycarbonyl)benzoic acid N-1,1-bis(phenylmethyl)methyl-N-3-phenylpropylamide.

6. A compound according to claim 1 wherein a compound of the formula (IB) is in the form of a non-toxic acid addition salt.

7. A process for the preparation of a compound of formula (IB):

(IB)

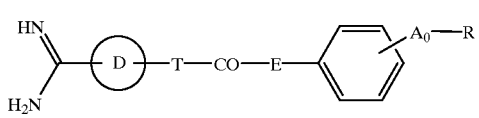

which comprises forming an ester or amide bond between a compound of the formula:

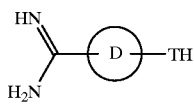

(wherein the various symbols are as defined in claim 1) and a compound of the formula:

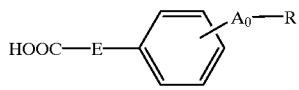

(wherein the various symbols are as defined in claim 1); and optionally converting the amidinophenol derivative thus obtained into a salt or acid addition salt thereof.

8. A method for the treatment of diseases induced by leukotriene $B_4$, phospholipase$A_2$, or trypsin, which comprises administering to a patient an effective amount of a compound of the formula (IB) depicted in claim 1, a non-toxic salt thereof, or a non-toxic acid addition salt thereof.

9. A method for the treatment of diseases induced by leukotriene $B_4$, which comprises administering to a patient an effective amount of a compound of the formula (IB) depicted in claim 1, a non-toxic salt thereof, or a non-toxic acid addition salt thereof.

10. A method for the treatment of diseases induced by phospholipase$A_2$ or trypsin, which comprises administering to a patient an effective amount of a compound of the formula (IB) depicted in claim 1, a non-toxic salt thereof, or a non-toxic acid addition salt thereof.

11. A method for the treatment of diseases of inflammation or allergy induced by leukotriene $B_4$, which comprises administering to a patient an effective amount of a compound of the formula (IB) depicted in claim 1, a non-toxic salt thereof, or a non-toxic acid addition salt thereof.

12. A pharmaceutical composition which comprises, as active ingredient, an effective amount of a compound of the formula (IB) depicted in claim 1, a non-toxic salt thereof, or a non-toxic acid addition salt thereof, with a carrier or coating.

13. The amidinophenyl derivative of claim 1, wherein the derivative is 4-[2-(4-amidinophenoxycarbonyl)-1-methylethenyl]benzoic acid N-ethoxycarbonylmethyl-N-allylamide having the structure:

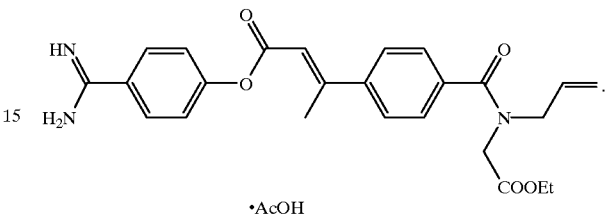

14. The amidinophenyl derivative of claim 1, wherein the derivatives is 4-[2-(4-amidinophenoxycarbonyl)-1-propenyl]benzoic acid N-ethoxycarbonylmethyl-N-allylamide.

15. The amidinophenyl derivative of claim 1, wherein the derivative is 4-[2-(4-amidinophenoxycarbonyl)-1-methylethenyl]benzoic acid N-i-(S),3-bis(ethoxycarbonyl)-propylamide.

16. The amidinophenyl derivative of claim 1, wherein the derivative is 4-[2-(4-amidinophenoxycarbonyl)-1-propenyl]benzoic acid N-1-(S),3-bis(ethoxycarbonyl)-propyl amide.

17. The amidinophenyl derivative of claim 1, wherein the derivative is 4-[2-(4-amidinophenoxycarbonyl)ethenyl]benzoic acid N-1-(S),3-bis(ethoxycarbonyl)-propyl amide.

* * * * *

UNITED STATES PATENT AND TRADEMARK OFFICE
CERTIFICATE OF CORRECTION

PATENT NO.    : 6,262,114 B1
DATED         : July 17, 2001
INVENTOR(S)   : Hisao Nakai et al.

It is certified that error appears in the above-identified patent and that said Letters Patent is hereby corrected as shown below:

Column 95,
Line 45, following the last line and before the period after "time" the following was omitted: "or non-toxic addition salt thereof or a non-toxic acid addition salt thereof."

Column 96,
Line 14, Claim 5 should read as follows:
    5.    A compound according to claim 1, which is
    4-[2-(4-amidinophenoxycarbonyl)ethenyl]benzoic acid N-1-(S), 3-bis(ethoxycarbonyl)propylamide,
    4-[2-(4-amidinophenoxycarbonyl)-1-propenyl]benzoic acid N-1-(S), 3-bis(ethoxycarbonyl)propylamide,
    4-[2-(4-amidinophenoxycarbonyl)-1-propenyl]benzoic acid N-ethoxycarbonylmethyl-N-allylamide,
    4-[2-(4-amidinophenoxycarbonyl)-1-methylethenyl]benzoic acid N-1-(S), 3 bis(ethoxycarbonyl)propylamide, or
    4-[2-(4-amidinophenoxycarbonyl)-1-methylethenyl]benzoic acid N-ethoxycarbonylmethyl-N-allylamide.

Signed and Sealed this

Third Day of December, 2002

JAMES E. ROGAN
*Director of the United States Patent and Trademark Office*